United States Patent
Lam et al.

(10) Patent No.: US 6,576,753 B1
(45) Date of Patent: Jun. 10, 2003

(54) DNA ENCODING HUMAN LEUKOTRIENE $C_4$ SYNTHASE

(75) Inventors: Bing K. Lam, Roslindale, MA (US); John F. Penrose, Norwood, MA (US); K. Frank Austen, Wellesley, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/809,592

(22) Filed: Mar. 15, 2001

Related U.S. Application Data

(62) Division of application No. 08/845,230, filed on Apr. 18, 1997, now abandoned, which is a continuation-in-part of application No. 08/683,117, filed on Jul. 16, 1996, now abandoned, which is a continuation of application No. 08/246,991, filed on May 20, 1994, now abandoned.
(60) Provisional application No. 60/015,645, filed on Apr. 19, 1996.

(51) Int. Cl.[7] .......................... C07H 21/02; C07H 21/04
(52) U.S. Cl. .................... 536/23.2; 536/23.5; 536/24.1; 536/24.3; 536/24.31; 536/24.33
(58) Field of Search ............................. 536/23.1, 23.2, 536/23.5, 24.3, 24.1, 24.31, 24.33

(56) References Cited

U.S. PATENT DOCUMENTS 5,952,210 A 9/1999 Creely et al. ................ 435/193

FOREIGN PATENT DOCUMENTS

WO  WO 95/33839  12/1995

OTHER PUBLICATIONS

Bach, et al., "Solubilization and Characterization of the Leukotriene $C_4$ Synthetase of Rat Basophil Leukemia Cells: A Novel, Particulate Glutathione S–Transferase", *Archives of Biochemistry and Biophysics*, 230(2): 455–465, 1984.
Hayashi, K., "PCR–SSCP: A Method for Detection of Mutations", *GATA*, 9(3): 73–79, 1992.
Izumi, et al., "Solubilization and Partial Purification of Leukotriene $C_4$ Synthase from Guinea–Pig Lung: A Microsomal Enzyme with High Specificity Towards 5,6–Epoxide Leukotriene A", *Biochimica et Biophysica Acta*, 959: 305–315, 1988.
Lam, et al., "Expression Cloning of a cDNA for Human Leukotriene $C_4$ Synthase, a Novel Integral Membrane Protein Conjugating Reduced Glutatione to Leukotriene $A_4$" *PNAS*, 91:7663–7667, 1994.

Lathe, R., "Synthetic Oligonucleotide Probes Deduced from Amino Acid Sequence Data Theoretical and Practical Considerations", *J. Mol. Biol.* 183: 1–12, 1985.
Leukotrienes and Other Products of the 5–Lipoxygenase Pathway, *The New England Journal of Medicine*,323(10): 645–652, 1990.
Lewis, et al., "The Biologically Active Leukotrienes", *The Journal of Clinical Investigations*, 73: 889–897, 1984.
McPherson, et al., "PCR with Highly Degenerate Primers", 171–186.
Nicholson, et al., "Purification of Human Leukotriene $C_4$ Synthase from Dimethylsulfoxide–Differentiated U937 Cells", *Eur. J. Biochem*. 209: 725–734, 1992.
Nicholson, et al., "Purification to Homogeneity and the N–Terminal Sequence of Human Leukotriene $C_4$ Synthase: A Homodimeric Glutathione S–Transferase Composed of 18–kDa Subunits", *Proc. Natl. Acad Sci. USA.*, 90: 2015–2019, 1993.
Penrose, et al., "Purification of Human Leukotriene $C_4$ Synthase", *Proc. Natl. Sci.*, 89: 11603–11606, 1992.
Sambrook, et al., "Molecular Cloning", Cold Spring Harbor Laboratory Press, 11.3–11.19.
Söderström, et al., "Leukotriene C Synthase in Mouse Mastocytoma Cells", *Biochem., J.* 250: 713–718, 1988.
Welsch, et al., "Molecular Cloning and Expression of Human Leukotriene–$C_4$ Synthase", *Proc. Nat. Aca. Sci., USA*, 91: 9745–9749, 1994.
Yoshimoto, et al., "Isolation and Characterization of Leukotriene $C_4$ Synthetase of Rat Basophilic Leukemia Cells" *Proc. Natl. Acad. Sci. USA*, 82: 8399–8403, 1985.
Yoshimoto, et al., "Properties of Highly Purified Leukotriene $C_4$ Synthase of Guinea Pig Lung" *J. Clin. Invest*. 81: 866–871, 1988.

*Primary Examiner*—Carla J. Myers
(74) *Attorney, Agent, or Firm*—Brenda Herschbach Jarrell; Choate, Hall & Stewart

(57) ABSTRACT

The present invention provides nucleotide sequences encoding human $LTC_4$ synthase or variants thereof, which nucleotide sequences include a human $LTC_4$ synthase genomic clone, and unique fragments thereof. The present invention also provides recombinant plasmids, and cells transformed therewith, including the $LTC_4$ synthase gene sequences. The present invention further provides the chromosomal localization of the human $LTC_4$ synthase gene, and also provides methods for identifying $LTC_4$ synthase gene mutations that correlate with susceptibility to bronchial asthma. Diagnostic methods are also provided, as are methods for identifying $LTC_4$ synthase modulators (i.e., compounds that alter the expression and/or activity of $LTC_4$ synthase). The presents invention also provides functional equivalents of the $LTC_4$ synthases, protein, and also methods of identifying $LTC_4$ synthase inhibitors.

5 Claims, 15 Drawing Sheets

```
                                    AGCGTTCCCCAGCTCGCCTTCACACAGCCCGTGCCACCACACC   45
GAC GGT ACC ATG AAG GAC GAG GTA GCT CTA CTG GCT GCT GTC ACC                       90
CTC CTG GGA GTC CTG CTG CAA GCC TAC TTC TCC CTG CAG GTG ATC                      135
TCG GCG CGC AGG GCC TTC CGC GTG TCG CCG CTC ACC ACC GGC                          180
CCA CCC GAG TTC GAG CGC GTC TAC CGA GCC CAG GTG AAC TGC AGC                      225
GAG TAC TTC CCG CTG TTC CTC GCC ACG CTC TGG GTC GCC GGC ATC                      270
TTC TTT CAT GAA GGG GCG GCC CTG TGC GGC CTG GTC TAC CTG                          315
TTC GCG CGC CTC CGC TAC TTC CAG GGC TAC GCG CGC TCC GCG CAG                      360
CTC AGG CTG GCA CCG CTG GCT GCG CTC CTC GCC GCC CTC TGG CTG                      405
CTG GTG GCG CTG GCG CTG CTC CTC GGA CGG CTC CGG ACG CTG CTG                      450
GCC GCG CTG CGC GCC GCG CTC CTC GGA CGG CTC CGG ACG CTG CTG                      495
CCG TGG GCC TGA GACCAAGGCCCCCGGGCCGACGGAGCCGGGAAAGAAGAGCCGG                      550
AGCCTCCAGCTGCCCCGGGGAGGGGCGCTCGCTTCCGCATCCTAGTCTCTATCATTAAA                      609
GTTCTAGTGACCG(polyA)  622
```

```
  1 MKDEVALLAAVT                                                    12
 13 LLQLAYAFSPPRAVYRATNGTIVI                                        27
 28 SARPFREPLFAATLCGYALVRCSI                                        42
 43 GPPEHFFHEGARLPLAAQWAVLRSI                                       57
 58 EYFFARLAPYLAAFQYLARSTGIL                                        72
 73 FFARLAPYLAAFQYLAR                                               87
 88 LAPLAALARALLGASLRAHWFLPQL                                      102
103 RLAVAAALLFRLLLGLLLFHRTLPL                                      117
118 LLAAPWA                                                        132
133                                                                147
148 AAA                                                            150
```

(Sequence as displayed in FIG. 2; letters arranged in 11 columns with position markers 12, 27, 42, 57, 72, 87, 102, 117, 132, 147, 150.)

```
       gagctcacagagcccccagctgggggcatatctggtttccggggcaggggcgataccc agag    -1446
       gaggaagggattctgagagaccaggcccaacaggcagagccccaggcctcaggctggagagctt    -1385
       gggcagccaaggaaggacccaggtgcgagggcagaaccatgcgcccgaccctgcagcacg        -1263
       gcctgtggcctccccgaccagctcctgcctgctcttctgggtcagtctggactctgccactt ct   -1141
       gaccaaaaagccaccgcaaaacccgcaaacccactcaaggccactcaggaggaggggcgag...    -1019
       ggaaggctgcggcccaggggcaggggcactccaggcaggagcgagggcgccgggggcctccag
       gcggggcgagggagagacaccagaactccaggcaggagtcctgggtgcacctt cctctc
       cacctggcctgccctgcgtgggctctgtcctcaggtgcccgccgtag[tccccc]cactct       -897
                                                   AP-2
       gagtttcctgtcccaaagtcctaaggaagttccagaactacatctccaccatctg[tgagtca     -775
                                                              AP-1
       g]ccttggctcagtgtccatctccacaggtgaaggcctgaaggagtcagcactgtcctgtcc agacc
       acagggcctgagtgagtgtgcggggcagcagcacagacagtggccagcaggcaggtttgttacct tga    -653
       gcaagagggagaggggctgaggggatggccacaagcaggggcctgtgtggaggcccaagagag
       gcctgggagaggggctgcctcctggcagggtggcaccacaacgactaaggctggcagg          -531
       gtttcctcctgaaggtttcctgaaggagagagcttgtgggggcttccgcagagtggggggctggg
       catgaggtttcctgaacagcctggatgggaacagagtccccagtgtgcagaggagggtttggcagggg t    -409
       actccattctgccaggaacagctggctgcctccagcatgtgggagctgaccagaagcttgggctgcc ac   -287
       tgccaggggctggctgcctcccgtgcaagccagacaaggggcacgaaggaaggcagaagttaggcggg
       agcctgggggctagggcagggggactaggcaaggaaggggcacgaaggaaggttgggctctgccac
       gcgggactaggcaaggaaggggcacgagagcaaggaagttggcttgaggcggttctccagctag        -165
       ctgctctccccgccccagacactccccctgccctgccgtgttcctcctgctggccctgcctggctc
       tgtgtggtatggtcacacatgtgcacacccccgtgcacgtgcaccctgccccctcactgagatg[ggcggg]ggagagcaccg    -43
                                                                    SP-1
       aggctgc[tCTTCCTCTCCTCCTGGGCCGTCCTCTGAGCAGCAGACGGGCTAAGCGTTCCCAG      80
Ex. I   CTCGCCTTCACACAGCCCGTGCCACCACACCGACGGTACCATGAAGGACGAGGTAGCTC
                                             -11
        TACTGGCTGCTGTCACCTCCCTGGGAGTCCTGCTGCTGCTGCTGCAAGgtgggctggttcctatctagga
```

```
                                                                                       1910
ggcaggggcgcacgcgctggacccccgggacccgcgcaggcgctcaccaggcccgtgcgt
acctctcgcag GGGCGCGGCTCCGCGCGCTACCTGTTCGCGCCTCCGCTAC
          TTCCAGGGCTACGCGCGCTCCGCGCAGCTCAG gtgagggccggcggggagcggggcgggg   2032
cggggaaagatcgcgggcggggcgggcgcctttggggattcgggagcgcctggcggccagagg           2154
gacgggccgagccgagcccagcgcggctttggggattcgggagcgcctggcggccagagg
aagtccccgtggggcccgcaggttgcggggaagaagcggggcggcctcctcgcgccactcccc
gctgaccgcgccgcgcag GCTGGCACCGCTGTACGCTTCCTCCCCACTTCCTGGCTGCTG   2276
                  GTGGCGCTGGCTGCTGTCGGCCGACGCTCCGGACGCTCCGGACGCG
                  TCCTCGGACGCGGCTCCGGACGCTCCGGACGCCCCGGCCGACGG
                  AGCCGGGAAAGAGAAGAGCCGGAGCCCTCAGCCCTCGCTTCCGCATC
                  CTAGTCTCTTATC ATTAAA GTTCTAGTGACCG agacccggcgttctctggtccgcgg   2398
Ex. V                        PolyA Signal gggtggcgcaccgcggctacggagcctggagggccccgagtccggcagcccggg           2520
gcgggcttcctagtggtgcggcgtgagagtggctgcgaggagcccccctgggcg
ggactggatccggttccacggttcaccctcagctcagggggtcacaaggcc              2642
gcccagtcctgcgggttccctcgactctcagcgccgcagtcccctgcctcacagctg
tcagggcgcttccctcgactctcagcgccgcagtcccctgcctcacagctg              2764
acactagatagagccctgtgtggctctctcccaggtgaggggcaggtttcttttggtcag
cactggatccccctcgttaactgtaggtcaggtgttcaggtcagttccgcagagctg         2886
cgggcaccatgggagggggaacagcctcagggcaccttgggtctgggtctgcgcagacc
ttgggggatccaggggaggcccacacagaaacaaagaagtgactttagccaagtatgcaggag   3008
aaacggaggag 3019
```

FIG. 3C

Exon I

FLAP   ...agtgcaagctctc|ACTTCCCCTTCCTGATACAGGGCAGGTTGTGCAGCTGGAGGCAGAGAGCAGTCTCTCTGGAGCCTGAAGCAAA
LTC4S  ...tgctctt|CCTCTCCTGGGCCGTCCCTCTCTGAGCGACAGCAGAGACGGGCTAAGCGTTCCCCAGCCTTCACACAGCCCGTGCCACCA
                  MetAspGlnGluThrValGlyLeuAsnValValLeuLeuAlaIleValThrLeuIleSerValValGlnAsnG
                  CATGGATCAAGAAACTGTAGGCAATGTTGTCCTGTTGGCCATCGTCACCCTCATCAGCGTGGTCCAGAATG|gtaaggaaagcccttc....
                  CACCGAGGTACCATGAAGGACGAGGTAGCTCTACTGGCTGTGTGCTGCTGGCTGCTGCTGCAGCCTGCTGCAAG|gtgggctggtgttgccct....
                  MetLysAspGluValAlaLeuLeuAlaLeuAlaValThrLeuLeuLeuGlyValLeuLeuGlnA Exon II FLAP   ...cttggcag|GATTCTTTGCCCATAAAGTGGAGCACGAAAGCAGGACCCAGAATGGGAGGAGTTCCAGAGGACCGGAACACTTGCCTT
LTC4S  ...tccccag|CCTACTTCTCCTGCAGGTGATCTCGGCGCAGGGCCTTCCGCGCCGTCCGCGCGCCTTCCGCCATCCACCAGCCCA|CGAGCCGTCTACCGAGCCCA
                  lyPheSerLeuGlnValIleSerAlaArgSerPheGlnArgThrGlnAsnGlyArgSerPheGlnArgThrGlyThrLeuAlaPh
                              GluArgValTyrThrAlaAs
                              TGAGCGGGTCTACACTGCCAA|gtgagtccaaccctg...
                              CGAGCCGTCTACCGAGCCCA|gtgaggcgcggcggg...
                              eGluArgValTyrArgAlaGl Exon III FLAP   ...ctgcag|CCAGAACTGTGTAGATGCGTACCCACTTCCCGCTACTTCCCGTTCTCCGCTGTCTTGTGCTGCGTCCAGCTCTGGTCTGCGGGCTACTTTGCAGCCAAG|gtaactcagacttccctt...
LTC4S  ...ccgcag|GGTGAACTGCAGCGAGTACTTCCCGTGTTCCTCCGCACGCTCGGGTCGCCGCCATCTTCTTTCATGAAG|gtcgggtgtggggcaggg...
                  nGlnAsnCysValAspAlaTyrProThrPheLeuAlaValLeuTrpSerAlaGlyLeuLeuCysSerGlnV
                  nValAsnCysSerGluTyrPheProLeuPheLeuLeuAlaThrLeuTrpLeuValAlaGlyIleIlePhePheHisGluG

FIG. 4A

```
C4-SYN       ----MKDE VALLAAVTLLGVLLQAYFSL QVISARRAFRVSPPLTTGPP EF    46
HUMAN FLAP   MDQETVGN-V---I---IS-VQ-GF-AHK-EHES-TQNGRSFQR--TLA-       50

C4-SYN       ERVYRAQVNCSE YFPLFLATLWVAGIFFHEGAAAL CGLVYLFA RLRYFQG         96
HUMAN FLAP   ---T-NQ--VDAY-T---V--S--LLCSQVP--FA--M--V-QK--V-            100

C4-SYN       YARSAQLRLAPLYASARA LWLLVALAALGLLAHFLPAAL RAALLGRLRTL         146
HUMAN FLAP   -LGERTQSTPGYIFGK-IILF-FLMSVA-IFNYY-IFFFGS DFENYIK-I         150

C4-SYN       LPWA-------                                                  150
HUMAN FLAP   STTISPLLIP                                                   161
```

FIG. 8

A.
```
----MKDEVALLAAVTLLGVLLQAYFSLQVISARRAFRVSPPLTTGPPEF   46
ERVYRAQVNCSEYFPLFLATLWVAGIFFHEGAAALCGLVYLFARLRYFQG   96
YARSAQLRLAPLYASARIILFLFLMSVAGIFNYYLIFFFGSDFENYIKTI  146
STTISPLLLIP 157
```

B.
```
----MKDEVALLAAVTLLGVLLQAYFSLQVISARRAFRVSPPLTTGPPEF   46
ERVYRAQVNCSEAYPTFLAVLWSAGLLCSQVPAAFAGLMYLFVRLRYFQG   96
YARSAQLRLAPLYASARALWLLVALAALGLLAHFLPAALRAALLGRLRTL  146
LPWA 150
```

C.
```
----MKDEVALLAAVTLLGVLLQAYFSLQVISARRAFRVSPPLTTGPPEF   46
ERVYRAQVNCSEAVLWSAGLLCSQVLAAFCGLVYLFARLRYFQG        96
YARSAQLRLAPLYASARALWLLVALAALGLLAHFLPAALRAALLGRLRTL  146
LPWA 150
```

DNA ENCODING HUMAN LEUKOTRIENE C₄ SYNTHASE

PRIORITY CLAIM

The present application is a divisional application of U.S. patent application Ser. No. 08/845,230 filed Apr. 18, 1997 now abandoned, which is a continuation-in-part of U.S. application Ser. No. 08/683,117 filed Jul. 16, 1996 now abandoned, which is a continuation of Ser. No. 08/246,991 filed May 20, 1994 now abandoned, and claims benefit to U.S. Ser. No. 60/015,645 filed Apr. 19, 1996. The entire contents of each of these prior applications are incorporated herein by reference.

This invention was made with U.S. Government support under NIH Grant HL36110, HL03208, AI22531, AI31599, AR36308, RR05950, and ES06105. The U.S. Government has certain rights to this invention.

BACKGROUND OF THE INVENTION

Leukotrienes are lipid-derived cell mediators that are released in response to a variety of immunologic and inflammatory stimuli. They are products of arachidonic acid metabolism derived through the 5-lipoxygenase pathway. Briefly, the initial step in leukotriene production involves oxygenation of arachidonic acid to produce 5S-hydroperoxy-6,8-trans-11,14 cis-eicosatetraenoic acid (5-HPETE), a subsequent dehydrase step producing the epoxide intermediate, 5,6-trans-oxido-7,9-trans-11,14-cis-eicosatetraenoic acid ($LTA_4$). Two routes of metabolism from $LTA_4$ lead to the production of biologically active products. One of these pathways involves conjugation of $LTA_4$ with glutathione (GSH) via $LTC_4$ synthase to produce the sulfur-containing leukotriene 5S-hydroxy-6R-S-glutathionyl-7,9-trans-11,14 cis-eicosatetraenoic acid ($LTC_4$). It is generally believed that $LTC_4$ synthase is a member of the glutathione S-transferase enzyme family.

$LTC_4$ has been implicated in a wide variety of diseases and pathologic conditions. $LTC_4$ has been identified in fluids from psoriatic lesions and bronchial secretions associated with adult respiratory distress syndrome and neonatal pulmonary hypertension (for review, see Lewis et al., *New Engl. J. Med.*, 323: 645, 1990, incorporated herein by reference).

Although the other enzymatic members of the 5-lipoxygenase pathway have been cloned, the cloning of $LTC_4$ synthase has been problematic. This is partly because the synthase is very labile in partially purified form and because the endogenous production of $LTC_4$ synthase in normal human cells is extremely small. $LTC_4$ synthase is present only in limited types of normal human cells, namely granulocytes derived from bone marrow. Moreover, oligonucleotides developed from the N-terminal region of the $LTC_4$ synthase polypeptide have not been specific enough to develop an effective screen because the N-terminal region is highly degenerate. In addition, an effective immunoassay for $LTC_4$ which relies on incubation of substrate, has also been problematic since breakdown products of the substrate have been shown to cross-react with antibodies used in the assay.

It has already been established that inhibitors of 5-lipoxygenase and of the cell receptors for leukotrienes are of substantial efficacy in the management of patients with bronchial asthma. Given that are only three points at which the leukotriene metabolic system can be disrupted: the activation and function of 5-lipoxygenase; the receptor for the leukotriene; or the function of $LTC_4$ synthase; characterization of $LTC_4$ synthase would be important, notwithstanding the problems associated with its cloning.

SUMMARY OF THE INVENTION

Human leukotriene $C_4$ synthase (also referred to herein as "$LTC_4$ synthase") has been cloned in an expression cloning system using a highly sensitive assay for $LTC_4$, the product of the reaction catalyzed by $LTC_4$ synthase. According to one aspect of the invention, an isolated nucleotide sequence encoding an $LTC_4$ synthase polypeptide or unique fragments of human $LTC_4$ synthase polypeptide, is provided. One embodiment is an isolated DNA sequence encoding a human $LTC_4$ synthase polypeptide that has three hydrophobic transmembrane domains. Additionally, the invention relates to mammalian $LTC_4$ synthase nucleotide sequences isolated from murine, porcine, ovine, bovine, feline, equine, or canine, as well as primate (e.g., simian) sources. Another embodiment is a human $LTC_4$ synthase genomic clone, or unique fragments thereof.

Also provided are recombinant cells and plasmids containing the foregoing isolated DNA, preferably linked to a promoter. Portions of the foregoing nucleotide sequences are also included in the invention. One such portion is contained in a vector within a host cell.

According to another aspect of the invention, isolated human $LTC_4$ synthase polypeptide is provided, having three hydrophobic transmembrane domains. Portions of the foregoing isolated human $LTC_4$ synthase polypeptides are also included in the invention. Antibodies with selective binding specificity for the polypeptides of the invention also are provided.

Another aspect of the invention is a method for producing human $LTC_4$ synthase polypeptide. The method includes providing an expression vector to a host, the vector containing a DNA sequence of the invention encoding for human $LTC_4$ synthase polypeptide, allowing the host to express the human $LTC_4$ synthase polypeptide, and isolating the expressed polypeptide.

A further aspect of the invention is an isolated nucleotide sequence capable of hybridizing to a target nucleotide sequence encoding human $LTC_4$ synthase polypeptide. The target includes a nucleotide sequence encoding a human $LTC_4$ synthase polypeptide with three transmembrane domains. The nucleotide sequence also can encode a human $LTC_4$ synthase polypeptide having amino acid sequences unique to the polypeptide.

The novel molecules of the invention can be employed in experimental or therapeutic protocols. For example, a method for interfering with the activity of a human $LTC_4$ synthase gene is provided, in which a construct is arranged to include a human $LTC_4$ synthase nucleotide sequence that, when inserted into the genome of a cell, either inactivates transcription of messenger RNA for human $LTC_4$ synthase polypeptide and/or inactivates translation of messenger RNA into human $LTC_4$ synthase polypeptide in that cell. This construct further has a promotor operatively linked to the $LTC_4$ synthase sequence. Next, the construct is introduced into a cell, and the construct is allowed to recombine with complementary sequences of the cell genome. Finally, cells lacking the ability to express human $LTC_4$ synthase polypeptide are selected.

A further aspect of the invention is an assay method for identifying a modulator of a human $LTC_4$ synthase polypeptide. One embodiment of the method includes providing a target cell containing an isolated nucleotide sequence which encodes for a human $LTC_4$ synthase polypeptide. The target cell is maintained under conditions and for a time sufficient for the synthase to be expressed in the target cell. The target cell is then exposed to a compound suspected of modulating human LTC$_4$ synthase polypeptide activity and a property of the target cell is measured in the presence of the modulator. This property is also measured in an identical target cell in the absence of the modulator. An altered property of the target cell exposed to the modulator is indicative of a modulating effect of the compound.

An alternative embodiment of the method of identifying LTC$_4$ synthase modulators involves fusing LTC$_4$ synthase gene promoter sequences (from the LTC$_4$ synthase genomic clone) to a reporter gene, altering at least a portion of the promoter sequences, and detecting the effects of the alterations on expression of the reporter gene so that transcriptional regulatory sequences are identified. Yet another embodiment involves incubating fragments of the LTC$_4$ synthase genomic clone with extracts of cells in which the LTC$_4$ synthase gene is expressed and thereby identifying within those extracts factors that bind to LTC$_4$ synthase genomic sequences and regulate LTC$_4$ synthase gene expression.

A highly sensitive assay for LTC$_4$, the product of the reaction catalyzed by LTC$_4$ synthase, is also described herein. The assay includes steps of contacting a carrier having bound to it an amount of an LTC$_4$ analogue (e.g., LTC$_2$) and incubating the carrier in the presence of a solution containing an unknown amount of LTC$_4$ synthase. Next, the carrier and solution are contacted with an amount of anti-LTC$_4$ antibody under conditions and for a time sufficient for the anti-LTC$_4$ antibody to bind with LTC$_4$ in solution and with analogue (LTC$_2$) on the carrier. Unbound anti-LTC$_4$ antibody is separated from the carrier and then the carrier is contacted with a second antibody linked to a fluorescent label under conditions and for a time sufficient for the second antibody to bind with anti-LTC$_4$ antibody associated with the carrier. The unbound second antibody is separated from the carrier and cell surface fluorescence of the carrier is analyzed by flow cytometry.

The present invention also provides the genomic location of the human LTC$_4$ synthase gene, as well as methods of identifying LTC$_4$ synthase gene polymorphisms that correlate with bronchial asthma. Methods of diagnosing susceptibility to bronchial asthma by detecting asthma-associated polymorphisms in LTC$_4$ synthase genomic sequences are also provided.

BRIEF DESCRIPTION OF THE FIGURES

FIG. 1 is the nucleotide sequence of a human LTC$_4$ synthase cDNA clone;

FIG. 2 is the deduced amino acid sequence of human LTC$_4$ synthase based upon the sequence of FIG. 1.

Figure 3B:
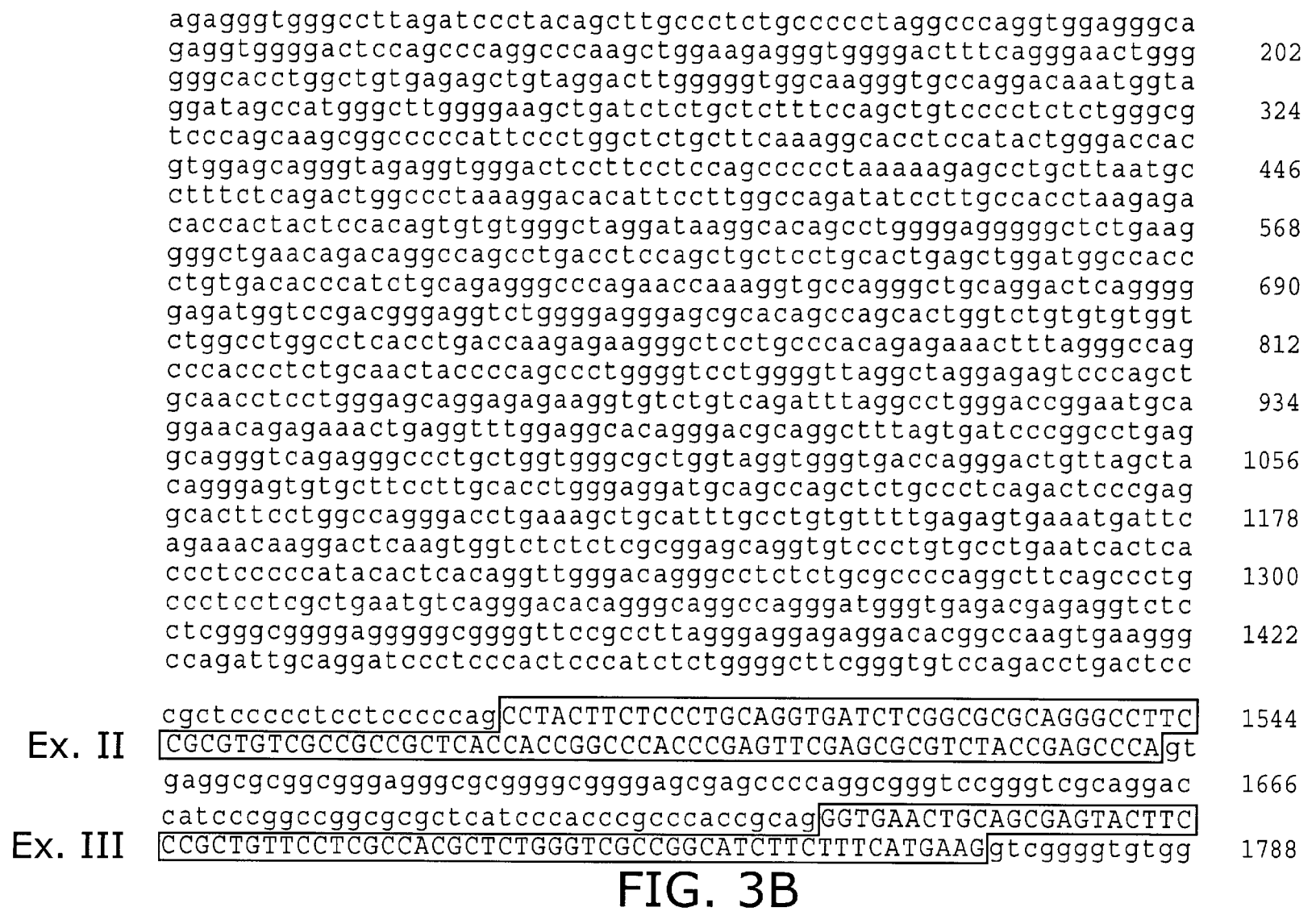

FIG. 3 is the nucleotide sequence of a LTC$_4$ synthase genomic clone. The introns, 1.25 kbp of 5' flanking sequence, and 0.44 kbp of 3' flanking sequence are shown in lower case symbols. The exons are depicted in upper case symbols. The putative SP-1 site and AP-1 and AP-2 enhancer elements are shown in small boxes; the predominant transcription start sites are circled; and the ATG translation initiation site is underlined.

FIG. 8 shows mutations made in the human LTC$_4$ synthase protein, as compared with FLAP.

FIG. 11 presents amino acid sequences of LTC$_4$ synthase/FLAP hybrid molecules. Panel A shows hybrid A, in which the third hydrophobic domain and the carboxyl terminus. Panel B shows hybrid B, in which the second hydrophobic domain has been substituted. Panel C shows hybrid C in which amino acid residues 66–81 of the second hydrophobic domain have been substituted with an additional point mutation, P78L. Substituted amino acid residues are printed in bold-faced type; numbers to the right indicate amino acid residues.

BRIEF DESCRIPTION OF THE SEQUENCES

Figure 4B:
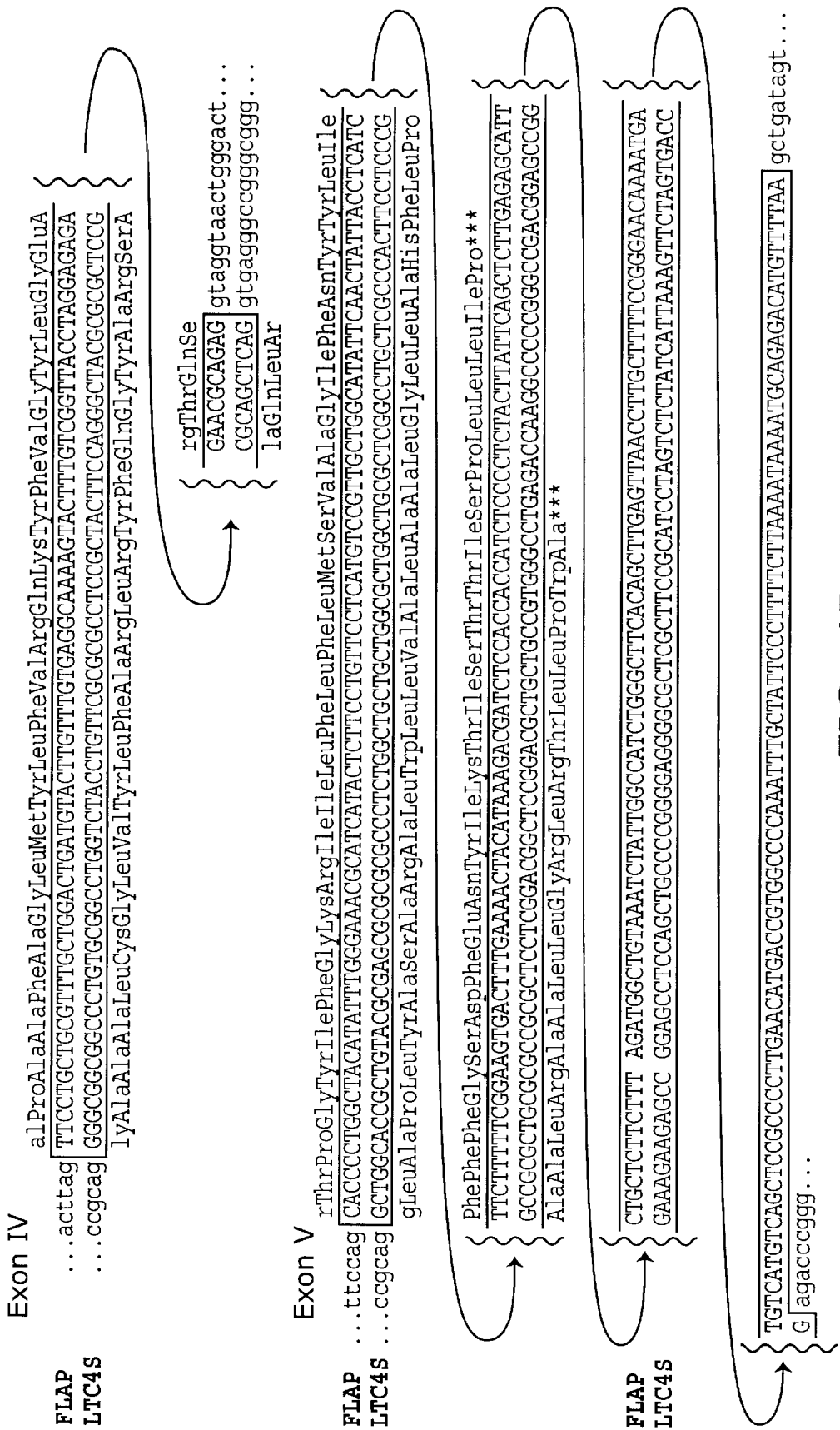
FIG. 4 is a comparison of the intron/exon junctions of the coding regions of the human FLAP and LTC$_4$ genes. The exons are in upper case letters and are within boxed regions, with deduced protein sequences provided in three-letter code above or below the respective nucleotide sequences.

SEQ ID NO.:1 is the isolated cDNA sequence of human LTC$_4$ synthase (GenBank accession number U09353);

SEQ ID NO.:2 is the deduced amino acid sequence of human LTC$_4$ synthase based upon SEQ ID NO.:1;

SEQ ID NO.:3 (VSPPLTTGPPEFER) is a 14 amino acid sequence that is an internal tryptic fragment of native LTC$_4$ synthase;

SEQ ID NO.:4 (AGCGTTCCCCAGCTCGCCTTC) and SEQ ID NO.:5 (CGGTCACTAGAACTTTAATGATAGAG) are a pair of oligonucleotide primers for PCR amplification of the human LTC$_4$ synthase gene;

SEQ ID NOs.: 6, 7 and 8 are the three extramembrane ("loop") amino acid sequences of SEQ ID NO.:2;

SEQ IN NO.:9 (MKDEVALLAAVTLLGVLLQAYF) is the N-terminal 22 amino acid sequence of LTC$_4$ synthase purified from native KG-1 cells;

SEQ ID NO.:10 is the genomic DNA sequence of human LTC$_4$ synthase (GenBank accession number U50136).

DETAILED DESCRIPTION OF PREFERRED EMBODIMENTS OF THE INVENTION

The present invention encompasses human leukotriene C$_4$ (LTC$_4$) synthase nucleic acids and polypeptides. The LTC$_4$ protein described herein is a 150-amino acid residue integral membrane protein with three hydrophobic transmembrane domains. The human LTC$_4$ synthase complementary DNA (cDNA) is a 694 base pair sequence that encodes the functional LTC$_4$ synthase enzyme. The genomic clone includes five exons and four introns, as well as various regulatory sequences.

The nucleotide and amino acid sequences provided herein, the configuration and number of transmembrane hydrophobic domains, and the lack of homology to known sequences, define unique nucleotide and polypeptide structures. In this regard, the terms "homology" or "homologous" are necessarily defined relative to a comparison between two sequences. Given the known pattern of codon degeneracy, any identity between two nucleotide sequences above the codon degeneracy "noise", is considered to be a "signal" of homology. Preferably, at least 50% identity of nucleotide sequence is indicative of a "homologous" sequence.

In one embodiment, the present invention provides an isolated nucleic acid molecule that encodes human LTC$_4$ synthase. The term "isolated", when applied to the nucleotide molecules of the present invention refers to an RNA or DNA polymer, portion of genomic nucleic acid, cDNA, or synthetic nucleic acid which, by virtue of its origin or manipulation: (i) is not associated with all of a nucleic acid with which it is associated in nature (e.g., is present in a host cell as a portion of an expression vector); (ii) is linked to a nucleic acid or other chemical moiety other than that to which it is linked in nature; (iii) does not occur in nature; (iv) has been amplified in vitro by, for example, the polymerase chain reaction (PCR); (v) has been synthesized by, for example, chemical synthesis; (vi) has been recombinantly produced by cloning; and/or (vii) has been purified, as by cleavage and gel separation.

FIG. 1 presents a 694 base pair cDNA sequence (SEQ ID NO.:1) coding for LTC$_4$ synthase that has been isolated from human myelocytic cells. An open reading frame of 450 base pairs is identified from nucleotides 55 to 505 (TGA stop codon) of SEQ ID NO.:1 (FIG. 1) and predicts an amino acid sequence of 150 amino acids (SEQ ID NO.:2 and FIG. 2). Numbering of nucleotides follows the convention of starting with the first base pair (A) of SEQ ID NO.:1 as base number 1; amino acid residues begin with the start codon (ATG-bases 55–57) as residue number 1.

The cDNA contains a 54 nucleotide 5' non-translated region; 450 nucleotides of translated sequence; a 193 nucleotide 3' untranslated region that includes an ATTAAA polyadenylation signal (in bold lettering in FIG. 1), and a polyA+ tail (72 base pairs long—not shown in FIG. 1), indicating its full length.

The cDNA sequence of SEQ ID NO.:1 shows no significant homology with nucleotide sequences in GENBANK or EMBL databanks (using Molecular Biology Computer Research Resources [MBCRR] software) for known cytosolic or microsomal GSH S-transferases. SEQ ID NO.:1 does show homology with the gene for 5-lipoxygenase activating protein (FLAP; see Dixon et al., Nature 343:282, 1990). Alignment of the coding nucleotide sequence according to regions of amino acid homology (see below) reveals 52 percent homology between FLAP and LTC$_4$ synthase in the N-terminal region. There is no nucleotide homology at the 3' end of the transcript for LTC$_4$ and the corresponding region of FLAP. FLAP then extends for an additional 300 base pairs.

Three different clones having the nucleotide sequence set forth in SEQ ID NO.:1 were isolated in our assay (see Example 1). SEQ ID NO.:1 was deposited with GENBANK and has been given GENBANK Accession Number U09353.

The information provided by SEQ ID NO.:1 was used to assay the expression of the gene to which SEQ ID NO.:1 corresponds. Specifically, Northern blot analysis was employed to study steady state transcription of LTC$_4$ synthase and its distribution in human eosinophils and the KG-1 cell line. A 0.7 kb mRNA transcript was observed in these cells, both of which are known to contain LTC$_4$ synthase (see Example 1). The size of the mRNA (0.7 kb) is similar to that of SEQ ID NO.:1, consistent with SEQ ID NO.:1 being full length.

FIG. 3 and SEQ ID NO.:10 present 4465 nucleotides of genomic LTC$_4$ synthase gene sequence. SEQ ID NO.:10 includes 5 exons and 4 introns. The exons show 100% identity with the LTC$_4$ synthase cDNA sequence of SEQ ID NO.:1. The exons are small, ranging in size from 71 to 257 nucleotides, and are interrupted by small introns (see FIG. 3). The intron/exon junctions of LTC$_4$ synthase align identically with those of FLAP; however, the small size of the LTC$_4$ synthase gene (2.51 kilobasepairs) contrasts with the >31 kbp size reported for FLAP.

Primer extension analysis on poly-A+ RNA isolated either from culture-derived human eosinophilic granulocytes or from the KG-1 myelogenous cell line has revealed that the genomic gene represented by SEQ ID NO.:10 has multiple transcriptional start sites, with prominent signals at 66, 69, and 96 base pairs (bp) 5' of the ATG translation start site (see FIG. 3). Analysis of the 5' flanking region present in SEQ ID NO.:10 revealed a GC-rich promoter sequence consistent with an SP-1 site as well as consensus sequences for AP-1 and AP-2 enhancer elements at positions 24, 807, and 877 bp 3', respectively, from the first transcription start site (see FIG. 3).

Genes for other proteins in the pathways of lipid mediator biosynthesis, such as 5-, 12-, and 15-lipoxygenases also have upstream SP-1 sites, positioned similarly (see Funk et al., Proc. Natl. Acad. Sci. USA 86:2587, 1989; Funk et al., Proc. Natl. Acad. Sci. USA 89:3962, 1992). The presence of AP-1 and AP-2 sites, which are responsive to the activation of protein kinase C by phorbol 12-myristate 13-acetate (PMA) is consistent with the observation that LTC$_4$ synthase activity is induced in HL-60 cells (Nicholson et al., J. Biol. Chem., 267:17849, 1992) and in human erythroleukemia cells after treatment with PMA (Soderstrom et al., Biochem. Biophys. Res. Comm. 189:1043, 1992).

Southern blot analysis showed that the gene corresponding to SEQ ID NO.:10 is present in single copy in the human genome; fluorescent in-situ hybridization mapped this gene to chromosomal location 5q35, in close proximity to a cluster of genes that encode cytokines and receptors that are involved in the regulation of cells central to allergic inflammation and implicated in bronchial asthma. These clustered genes include genes for IL-3, IL-4, IL-5, granulocyte-macrophage colony stimulating factor (GM-CSF), IL-9, IL-13, and fibroblast growth factor-acidic, which are all localized within a gene cluster at 5q23–5q31 (van Leeuwn et al, *Blood* 73:1142, 1989; Wasmuth et al., *Cytogenet. Cell Genet.* 58:261, 1991). Receptors that have been localized more distally in the 5q31–q32 region include the 2 adrenergic receptor and the lymphocyte specific corticosteriod receptor; and colony-stimulating-factor (CSF) receptor-1, monocyte-CSF receptor, and platelet-derived growth factor receptor are in the 5q33–q35 region (Wasmuth et al., supra; Kobilka et al., *Proc. Natl. Acad. Sci. USA* 84:46, 1987). The most distal genes located in the 5q34–q35 region include dopamine receptor 1 and -butyric acid A receptor (Wasmuth et al., supra). The FLAP gene and the 5-LO gene are not located on chromosome 5, but rather on chromosomes 13 and 10, respectively (Ford-Hutchinson et al., *Ann. Rev. Bioch.* 63:383, 1994; Funk et al., *Proc. Natl. Acad. Sci. USA* 89:3962, 1992).

As discussed thus far, the present invention provides nucleic acids encoding human $LTC_4$ synthase. In addition, the invention provides the amino acid sequence of human $LTC_4$ synthase, deduced from SEQ ID NO.:1. The sequence of the isolated polypeptide is given in SEQ ID NO.:2. The term "isolated", when applied to the polypeptides of the present invention means polypeptides: (i) encoded by nucleic acids produced using recombinant DNA methods; (ii); synthesized by, for example, chemical synthetic methods; (iii) separated from at least some of the naturally-occurring biological materials with which they are associated in nature (e.g., purified using protein analytical procedures); (iv) associated with chemical moieties (e.g., polypeptides, carbohydrates, fatty acids, and the like) other than those associated with the polypeptide in its naturally-occurring state; and/or (v) that do not occur in nature.

SEQ ID NO.:2 represents a 150 amino acid residue protein with a calculated molecular weight and isoelectric point (pI) of 16,567 and 11.05, respectively. This protein contains 2 cysteine residues (residues 56 and 82), and two putative protein kinase phosphorylation sites (residues 28–30 and 111–113). A search of protein sequence databases (SWISSPROT and PIR using BLAST™ and MBCRR software), reveals that the $LTC_4$ synthase protein of SEQ ID NO.:2 shares 31 percent overall homology with FLAP. This homology increases to 44 percent between the N-terminal two thirds of SEQ ID NO.:2 (residues 4–97) and the N-terminal end of FLAP (amino acids 9–101). Within this N-terminal region, there are portions of near identity at residues 7–13 of $LTC_4$ synthase (6 of 8 residues identical) and residues 46–52 of $LTC_4$ synthase (6 of 7 residues identical).

A hydropathy analysis (see Kyte et al., *Molec. Biol.,* 157:105, 1982) of the $LTC_4$ synthase of SEQ ID NO.:2 was performed using a window of 6 amino acids. Briefly, a hydropathy analysis progressively evaluates the hydrophilic and hydrophobic properties of a protein as a scan along its amino acid sequence. There is a singular correspondence between interior portions of soluble, globular proteins and hydrophobicity, and a correspondence between exterior portions and hydrophilicity.

The hydropathy analysis revealed three potential transmembrane domains. Potential membrane spanning (hydrophobic) regions extend between amino acid residues 5–24, 59–89, and 114–135. The terms "hydrophilic" and "hydrophobic" in this context are primarily a function of the size of the amino acid "window" used in the hydropathy analysis. For the present purposes, "hydrophilic" refers to a stretch of amino acid sequences at least 20 residues long and scoring less than 0 on a Kyte-Doolittle plot; the scores are derived using a window of preferably at least 6 amino acids.

Native $LTC_4$ synthase protein from myelocytic KG-1 cells was solubilized, purified and sequenced (see Example 1). In addition, recombinant $LTC_4$ synthase protein derived from transfected COS-7 cells was purified and analyzed using SDS-PAGE electrophoresis (see Example 1). The predicted molecular weight of 16,567 for the protein of SEQ ID NO.:2 is in agreement with the observed mobility (18 kDa) of a native integral membrane protein. Furthermore, recombinant $LTC_4$ synthase purified from transfected cells also shows a molecular weight of approximately 18 kDa on SDS-PAGE. Furthermore, SEQ ID NO.:2 matched the N-terminal 22 amino acids of the $LTC_4$ synthase protein isolated and sequenced from KG-1 cells (SEQ ID NO.:9) and 14 of 14 internal amino acids (SEQ ID NO.:3) from tryptic fragments of the native protein. These 14 amino acids were identical to amino acid residues 35–48 of SEQ ID NO.:2. SEQ ID NO.:2 also matched 34 of 35 N-terminal amino acids purified from human leukemic THP-1 cell line (see Nicholson et al., *Proc. Nat. Acad. Sci. USA* 90:2015, 1993).

As one of ordinary skill in the art will readily appreciate, the nucleotide sequence information provided by the present invention allows construction of cell lines expressing the polypeptide of SEQ ID NO.:2 (see, for example, Example 3). The present invention therefore provides human $LTC_4$ synthase nucleic acid and protein sequences, as well as tools for expressing such protein sequences and for identifying related sequences encoding gene and protein homologs of human $LTC_4$ synthase, using techniques of molecular biology and genetic engineering techniques are well known in the art (see, for example, Sambrook et al., *Molecular Cloning: A Laboratory Manual,* 2nd ed., Cold Spring Harbor Laboratory Press, Cold Spring Harbor, N.Y., 1989). Particular protocols for isolating such sequences, and for using such sequences in other embodiments of the invention, are presented below:

A. Cloning Human Leukotriene $C_4$ Synthase Genes

1. Isolating a Human $LTC_4$ Synthase cDNA

A cDNA encoding $LTC_4$ synthase can be cloned by expressing an $LTC_4$ synthase from a cDNA expression library in mammalian COS-7 cells (see Example 1). Briefly, mRNA is isolated from cells containing $LTC_4$ synthase. Next, mRNA is used to prepare a cDNA library using an in vitro expression vector system. cDNA is synthesized, separated by gel electrophoresis and ligated into an expression vector. This synthetic cDNA library is used to transform a bacterial host and bacteria are then subjected to extraction of their plasmid cDNA. Plasmids are used to transfect mammalian cells. Such a cDNA library was screened for expression of $LTC_4$ synthase in transfectants by a highly sensitive, fluorescence-linked competitive immunoassay. Full-length $LTC_4$ synthase cDNA clones were obtained (see Example 1).

For sequencing, plasmid cDNA from the clones is extracted, then cloned into a vector for DNA sequencing, using standard methods (see for example, Sambrook, J. et al., supra; see also Example 1).

2. Isolating a Human LTC$_4$ Synthase Genomic Clone

We identified the LTC$_4$ synthase genomic clone presented as SEQ ID NO.:10 by having a P1 genomic library screened with a PCR product amplified from the cDNA clone of SEQ ID NO.:1 (see Example 6). As one of ordinary skill in the art will readily recognize, any unique fragment of SEQ ID NO.:1, prepared using any available technique, can be used as the probe. We probed the library with a PCR product that spanned nucleotides 496–622 of SEQ ID NO.:1, and identified a positive clone.

We confirmed that our positive genomic clone contained full-length sequence by showing that it hybridized with full-length LTC$_4$ synthase cDNA and with oligonucleotide primers from the 5' and 3' ends of the cDNA. We used overlapping PCR reactions to further demonstrate that our genomic clone contained full-length sequence. We also showed that the cDNA and genomic clones gave identical hybridization patterns when used to probe a DNA blot prepared from human genomic DNA or from P1 plasmid DNA.

B. Cloning Other Human Homologues of Human LTC$_4$ Synthase

One of ordinary skill in the art will readily recognize that sequence information provided by the above-discussed cloning of the human LTC$_4$ synthase cDNA and genomic clones enables ready identification of other human homologues of the LTC$_4$ synthase gene using any of a variety of known approaches. One approach is to screen a DNA library for the presence of a human LTC$_4$ synthase nucleotide coding sequence corresponding to a human homologue by generating preferred probes using the polymerase chain reaction. The probes are produced by using, for example, a human granulocyte or myelocytic cell line (i.e., KG-1, THP-1) cDNA library as a template for polymerase chain reaction (PCR). Based on the degree of codon degeneracy of the predicted amino acid sequence, PCR primers are derived from the human LTC$_4$ synthase nucleotide sequence of SEQ ID NO.:1. Examples of suitable PCR primer pairs include SEQ ID NO.:4 (AGCGTTCCCCAGCTCGCCTTC) and SEQ ID NO.:5 (CGGTCACTAGAACTTTAATGATAGAG) (see Example 2).

The product of the PCR reaction is cloned and the human cDNA library is rescreened using the PCR product as the probe(s). This preferred method, however, requires identifying tissue that expresses LTC$_4$ synthase as a source of RNA.

Tissues suspected of expressing the human homologue can be identified by RNA analysis, i.e., Northern blot analysis under low stringency conditions. Confirmation of a human tissue as an RNA source and identification of additional sources of tissue can be accomplished by preparing RNA from the selected tissue and performing Northern blot analysis under low stringency conditions using PCR product as the probe(s). A suitable range of such stringency conditions is described in Krause et al., *Met. in Enzymol.* 200:546, 1991. Additionally, genomic libraries can be screened for the presence of the human homolog coding sequence using a PCR generated probe(s).

C. Cloning Non-Human Homologues of the LTC$_4$ Gene

The sequence information provided herein allows identification of LTC$_4$ synthases from other non-human organisms, preferably mammals. Basically, gene-specific probes can be designed by identifying unique fragments of SEQ ID NO.:1 and/or SEQ ID NO.:10, and can be produced by any available technique, such as PCR or chemical synthesis. Such unique fragments can be employed to probe genomic and/or cDNA libraries from any desired cell such as, for example, murine, porcine, ovine, bovine, feline, equine, canine, or primate cells. Preferably, the library being probed is made from mammalian myelocytic cells.

In one specific embodiment, total mRNA can be isolated from mammalian tissues or from cell lines likely to express a LTC$_4$ synthase polypeptide homolog. In general, total RNA from the selected tissue or cell culture is isolated using conventional methods. Subsequent isolation of mRNA is typically accomplished by oligo (dT) chromatography. Messenger RNA for Northern analysis is size-fractionated by electrophoresis and the RNA transcripts are transferred to nitrocellulose according to conventional protocols (Sambrook et al., *Molecular Cloning: A Laboratory Manual*, 2nd. ed., Cold Spring Harbor Press, N.Y., 1989).

A labeled probe, for example PCR-generated, that is capable of hybridizing with the human LTC$_4$ synthase cDNA (SEQ ID NO.:1) can serve to identify RNA transcripts complementary to at least a portion of the LTC$_4$ synthase gene homolog. For example, if Northern analysis indicates that RNA isolated from murine lung tissue hybridizes with the labeled probe, then a murine lung cDNA library is a likely candidate for screening and identification of a clone containing the coding sequence for a murine homolog of human LTC$_4$ synthase polypeptide.

Northern analysis is often used to confirm the presence of mRNA fragments which hybridize to a probe corresponding to all or part of the human LTC$_4$ synthase gene. Northern analysis indicates the presence and size of the transcript, allowing one to determine whether a given cDNA clone is long enough to encompass the entire transcript or whether it is necessary to obtain further cDNA clones, for example, if the length of the cDNA clone is less than the length of RNA transcripts as seen by Northern analysis. If the cDNA is not long enough and full-length clones are desired, they can be identified by performing several steps such as: (i) rescreening the same library with the longest probes available to identify a longer cDNA; (ii) screening a different cDNA library with the longest probe; and (iii) preparing a primer-extended cDNA library using a specific nucleotide primer corresponding to a region close to, but not at, the most 5' available region—the primer is used to prime reverse transcription and then the primer extended library is screened with the probe corresponding to available sequences located at 5' to the primer (see, for example, Rupp et al., *Neuron* 6:811, 1991).

The preferred LTC$_4$ synthase homolog clone has a complete coding sequence, i.e., one that begins with methionine, ends with a stop codon, and preferably has another in-frame stop codon 5' to the first methionine. It is also desirable to have a cDNA that is "full length", i.e,. includes all of the 5' and 3' untranslated sequences. To assemble a long clone from short fragments, the full-length sequence is determined by aligning the fragments based upon overlapping sequences. Thereafter, the full-length clone is prepared by ligating the fragments together using the appropriate restriction enzymes.

As discussed above, PCR-generated probes may be used in the protocol for isolating mammalian homologues to human LTC$_4$ synthase gene. Moreover, probes to be used in the general method for isolating mammalian LTC$_4$ synthase can now include oligonucleotides, all of which encode at least part of the sequence shown in SEQ ID NO.:1. Unlike the PCR approach to generating a probe, the above-identified probes do not require prior isolation of RNA from a tissue expressing the vertebrate homolog.

An oligodeoxyribonucleotide probe typically has a sequence somewhat longer than that used for the PCR primers. A longer sequence is preferable for the probe, and it is "probe" refers to a strand of nucleic acid having a base sequence complementary to a target sequence. Preferred nucleotide sequences may hybridize if they contain sequences that have at least 50% identity to a target sequence. A preferred probe that can distinguish between a human LTC$_4$ synthase sequence and other sequences refers to a probe that includes SEQ ID NOs.:1 and/or 10, functional variants thereof, and/or fragments thereof.

Because the nucleic acid sequence of LTC$_4$ synthase gene is now known, those of ordinary skill in the art can readily determine nucleic acid sequences of the human LTC$_4$ synthase gene that are not homologous to any other nucleic acid sequence, including other human LTC$_4$ synthase sequences. These non-homologous sequences, and peptides encoded by them, are referred to as "unique" fragments and are meant to be included within the scope of the present invention.

Moreover, due to the degeneracy of nucleotide coding sequences, other nucleic acid sequences may be used in the practice of the present invention. These include, but are not limited to, sequences comprising all or portions of the human LTC$_4$ synthase sequences depicted in SEQ ID NO.:1 or SEQ ID NO.:10 which are altered by the substitution of different codons that encode the same amino acid residue within the sequence, thus producing a silent change. Such altered sequences are regarded as equivalents of the specifically claimed sequences.

Human LTC$_4$ synthase polypeptide or fragments or other derivatives thereof include, but are not limited to, those containing as a primary amino acid sequence all, or unique parts of the amino acid residues substantially as depicted in SEQ ID NO.:2, including altered sequences in which functionally equivalent amino acid residues are substituted for residues within the sequence, resulting in a silent change. According to the invention, an amino acid important that codon degeneracy be minimized. A representative protocol for the preparation of an oligonucleotide probe for screening a cDNA library is described in-Sambrook, et al., *Molecular Cloning: A Laboratory Manual,* 2nd ed., Cold Spring Harbor Press, New York, 1989. In general, the probe is labelled, e.g., with $^{32}$P, and used to screen clones of a cDNA or genomic library.

Alternately, an expression library can be screened using conventional immunization techniques, such as those described in Harlowe et al, *Antibodies,* Cold Spring Harbor Press, New York, 1988. Antibodies prepared using purified LTC$_4$ synthase as an immunogen are preferably first tested for cross reactivity with the homolog of LTC$_4$ synthase from other species. Other approaches to preparing antibodies for use in screening DNA libraries, as well as for use in diagnostic and research applications, are described below (see Example 3).

D. Nucleic Acid and Protein Sequences

The nucleic acid sequence of the human LTC$_4$ synthase cDNA is depicted in SEQ ID NO.:1; that of the genomic clone is presented in SEQ ID NO.:10. These sequences, their functional equivalents, or their fragments may be used in accordance with the invention. The term "fragments" refers to portions of the human LTC$_4$ synthase nucleic acid sequence (i.e., SEQ ID NO.:1 or SEQ ID NO.:10) that may find no counterpart in the known sequences of nucleic acids encoding other polypeptides. Subsequences comprising hybridizable portions of the LTC$_4$ synthase sequence have use, e.g., in nucleic acid hybridization assays, Southern and Northern blot analyses, etc.

Exemplary nucleotide subsequences of SEQ ID NO.:1 are those encoding extramembrane, "loop" portions of LTC$_4$ synthase, such as nucleotide sequences or portions of nucleotide sequences encoding (with reference to the residues of SEQ ID NO.:2) amino acid residues 25 to 58 (SEQ ID NO.:6); amino acid residues 90 to 113 (SEQ ID NO.:7); and amino acid residues 136 to 150 (SEQ ID NO.:8).

Exemplary nucleotide sequences of SEQ ID NO.:10 are each of the individual exons, each intron, and the region upstream of the transcriptional start site. Nucleic acids whose nucleotide sequence includes any one of these sequences, or any combination thereof, are encompassed by the present invention. Smaller unique sequences can readily be identified using computer programs. Preferred unique fragments are at least about 12 nucleotides or basepairs in length.

In addition to the LTC$_4$ synthase gene sequences of SEQ ID NOs.:1 and 10, and unique fragments thereof, the present invention encompasses altered nucleotide sequences. Specifically, the nucleic acid sequences depicted in SEQ ID NOs.:1 and/or 10 can be altered by mutations such a substitutions, additions or deletions that provide for functionally equivalent nucleic acid sequences. According to the present invention, a nucleic acid sequence is "functionally equivalent" compared with the nucleic acid sequence from which it was derived (e.g., from SEQ ID NO.:1 or SEQ ID NO.:10), if it satisfies at least one of the following conditions: (i) the nucleic acid sequence has the ability to hybridize to a human LTC$_4$ synthase nucleotide sequence, but it does not necessarily hybridize to that sequence with an affinity that is the same as that of the naturally occurring human LTC$_4$ synthase nucleic acid sequence; and/or (ii) the nucleic acid can serve as a probe to distinguish between the present human LTC$_4$ synthase sequences from other nucleotide sequences.

The term "probe", as used herein, refers to a ligand of known qualities that can bind selectively to a target. As applied to the nucleic acid sequences of the invention, the term sequence is "functionally equivalent" compared with a sequence depicted in SEQ ID NO.:2 if the amino acid sequence contains one or more amino acid residues within the sequence which can be substituted by another amino acid of a similar polarity which acts as a conservative substitution (i.e., a functional equivalent). For example, at least one of the tyrosine residues at positions 50, 97 and 109 of SEQ ID NO.:2 may be substituted by a phenylalanine, yielding a total of $2^3$ or 8 separate-functional equivalents of SEQ ID NO.:2.

In addition, substitutes for an amino acid within the sequence may also be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

As described in Example 9, we have identified several mutants of the LTC$_4$ synthase protein that are functionally equivalent to the protein whose sequence is presented as SEQ ID NO.:2. For example, the C56S and C82V mutants (in which cysteines at positions 56 and 82 are substituted with serine and valine, respectively) are functional equivalents of the wild-type protein; the mutations do not affect conjugation function of transfected COS cell membranes. Similarly, the E45Q, E47Q, E58Q, and R48S mutants are also functional equivalents of wild type LTC$_4$ synthase, as are the R51L and R51H mutants and various of the hydrophilic loop mutants (e.g., L39F, E45Q, F46Y, E47Q, R48S, Y50F, Q53N, V54Q, F60Y, L62T, T66V, V69S, H75Q, E76Q, Q25K, R92S, R99S, S100V, R104S, Y109I, S111V, and A52S). By contrast, the R51I and R51T mutations are not functional equivalents according to the present invention, as these mutants do not show conjugation activity. Accordingly, it can be concluded that mutations at R51 produce functional equivalents of the $LTC_4$ synthase protein when they preserve the charge at that position, but not when they disrupt it.

Preferred functional equivalents of the present invention are those that show at least about 60%, more preferably about 85%, and most preferably 100% of the activity of wild type $LTC_4$ synthase when assayed in the COS cell microsome assay described in Example 9. Those of ordinary skill in the art will recognize that particular functional equivalents are desirably created by altering the $LTC_4$ synthase amino acid sequence in a way that is unlikely to interfere with the protein's catalytic activity. For example, the analysis described in Example 9 identifies particular amino acids residues as likely contributing to the GSH binding site, indicates that Y93 plays a role in promoting the formation of the thiolate anion of GSH, and shows that R51, or other amino acid with similar charge, is required for catalytic activity. Without wishing to be bound by any particular theory, we propose that R51 is responsible for opening the epoxide ring of $LTA_4$ for conjugation with the thiolate anion of the reduced GSH (see FIG. 13). Consistent with this idea, we note that the recently-identified microsomal GST II, which possesses some ability to conjugate $LTA_4$ with GSH, also contains an R51 residue (Jakobsson et al., *J. Biol. Chem.* 271:22203, 1996). Mutational studies directed at identifying $LTC_4$ synthase functional equivalents should preferably be designed to avoid disrupting this activity.

The analysis described in Example 9 also shows that $LTC_4$ synthase derivatives that bear mutations within the putative FLAP inhibitor domain-like region are functional equivalents according to the present invention. Observations that the FLAP inhibitor MK-886 could also inhibit $LTC_4$ synthase activity when administered at high doses (see Lam et al., *Proc. Natl. Acad. Sci. USA* 91:7663, 1994; Lam et al., *Eur. J. Biochem.* 238:606, 1996) suggested that the active site of $LTC_4$ synthase might be related to that of FLAP. Mutations of FLAP residue D62 had established a role for this negatively-charged residue in binding to the inhibitor, which suggests that D62 forms part of the FLAP catalytic site. Surprisingly, a corresponding change in $LTC_4$ synthase (mutation of E48) has no effect on $LTC_4$ synthase activity (see Example 9). Other mutations in this region also do not interfere with conjugation by $LTC_4$ synthase. The present invention therefore provides the unexpected finding that $LTC_4$ synthase functional equivalents include those bearing mutations in the $LTC_4$ synthase region that corresponds to the FLAP inhibitor binding domain.

Substantial changes in functional or, for example, immunological properties may be made by selecting substitutes that differ from the original amino acid residue. More significantly, the substitutions are chosen for their effect on: (i) maintaining the structure of the peptide backbone in the area of the substitution, for example, as a sheet or helical conformation; (ii) maintaining the charge or hydrophobicity of the molecule at the target side; or (iii) maintaining the bulk of the side chain.

The substitutions that in general are expected to induce greater changes in the functional properties of $LTC_4$ synthase are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

In particular, any change in the number of arginine residues will have an effect on the isoelectric point (pI) of the $LTC_4$ synthase. Arginine has the highest pI (10.76) of all the standard amino acids. Fewer arginine residues would be expected to result in an $LTC_4$ synthase with a lower pI and may be expected to result in an enzyme with reduced activity. Substitution of an arginine residue of SEQ ID NO.:2 with an aspartic acid (pI=2.77) is a particularly effective substitution for lowering the $LTC_4$ synthase isoelectric point. For example, SEQ ID NO.:2 has 13 arginine residues at positions 30, 31, 34, 48, 51, 90, 92, 99, 104, 113, 136, 142, and 144. Substitution of at least one aspartic acid for at least one of these arginines would yield a total of $2^{13}$ or 8192 separate modifications of SEQ ID NO.:2.

In addition, substitution of at least one arginine residue with at least one glutamic acid (pI=3.22) is another substitution likely to lower the $LTC_4$ synthase isoelectric point. Substitution of at least one glutamic acid for at least one of these arginines would also yield a total of $2^{13}$ or 8192 separate modifications of SEQ ID NO.:2. Synthesis of all of these sequences is well within the present level of skill in the art.

Most deletions and insertions in the human $LTC_4$ synthase polypeptide, and substitutions in particular, are not expected to produce radical changes in the characteristics of the polypeptide. Nevertheless, when it is difficult to predict the exact effect of the substitution, deletion, or insertion in advance of doing so, one skilled in the art will appreciate that the effect will be evaluated using routine screening assays as described below. For example, a change in the immunological character of the human $LTC_4$ synthase polypeptide, such as binding to a given antibody, is measured by an immunoassay such as a competitive type immunoassay.

Certain deletion mutants of $LTC_4$ synthase are also shown herein to constitute functional equivalents of the protein of SEQ ID NO.:2 (see Example 9). For example, mutants lacking the K2 or D3 residues, or the carboxy terminal tail of the protein are functional equivalents. Also, various substitution mutants, in which portions of the second or third hydrophobic domain of $LTC_4$ synthase are substituted, for example with analogous sequences from FLAP, are functionally equivalent to wild-type $LTC_4$ synthase. The results of these studies indicate that hydrophobicity is more important that sequence in the third hydrophobic domain of $LTC_4$ synthase, so that functional equivalents can be produced by preserving hydrophobicity even though amino acid sequence is changed. By contrast, the particular amino acid sequence is more important than hydrophobicity in the second hydrophobic domain. Also, $LTC_4$ synthase functional equivalents include dimers with one non-functional monomer. Those of ordinary skill in the art will recognize that these are mere examples of functional equivalents of the present invention; the invention is not limited to these embodiments.

Also included within the scope of the invention are human $LTC_4$ synthase polypeptides or unique fragments or derivatives thereof which are differentially modified during or after translation, e.g., by phosphorylation, glycosylation, crosslinking, acylation, proteolytic cleavage, linkage to an antibody molecule, membrane. molecule or other ligand, (Ferguson et al., *Ann. Rev. Biochem.* 57:285, 1988).

In addition, the recombinant human $LTC_4$ synthase polypeptide-encoding nucleic acid sequences of the invention may be engineered so as to modify processing or expression of the human $LTC_4$ synthase polypeptide. For example, and not by way of limitation, the human $LTC_4$ synthase nucleotide sequence(s) may be combined with a promoter sequence and/or a ribosome binding site using well characterized methods, and thereby facilitate harvesting or bioavailability.

Now that the cDNA of human $LTC_4$ synthase has been identified, it will be readily appreciated that the human $LTC_4$ synthase nucleotide sequence can be mutated in vitro or in vivo, to create variations in coding regions and/or form new restriction endonuclease sites or destroy preexisting ones, to facilitate further in vitro modification. Any technique for mutagenesis known in the art can be used including, but not limited to, in vitro site-directed mutagenesis (Hutchinson et al., *J. Biol. Chem.* 253:6551, 1978), use of TAB® linkers (Pharmacia), PCR-directed mutagenesis, and the like.

In addition to generating fragments of $LTC_4$ synthase from expression of cloned partial sequences of human $LTC_4$ synthase polypeptide DNA, fragments of human $LTC_4$ synthase polypeptide can be generated directly from the intact polypeptide. Proteins are specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the $\epsilon$-amino groups of lysine with ethyltrifluorothioacetate in mildly basic solution yields a blocked amino acid residue whose adjacent peptide bond is no longer susceptible to hydrolysis by trypsin (Goldberger et al. *Biochem.* 1:401, 1962). Treatment of such a polypeptide with trypsin thus cleaves only at the arginyl residues.

Polypeptides also can be modified to create peptide linkages that are susceptible to proteolytic enzyme catalyzed hydrolysis. For example, alkylation of cysteine residues with $\delta$-halo ethylamines yields peptide linkages that are hydrolyzed by trypsin (Lindley, *Nature* 178:647, 1956). In addition, chemical reagents that cleave polypeptide chains at specific residues can be used (Withcop, *Adv. Protein Chem.* 16:221, 1961). For example, cyanogen bromide cleaves polypeptides at methionine residues (Gross et al., *J. Am Chem Soc.* 83:1510, 1961). Thus, by treating $LTC_4$ synthase or fragments thereof with various combinations of modifiers, proteolytic enzymes and/or chemical reagents, numerous discrete overlapping peptides of varying sizes are generated. These peptide fragments can be isolated and purified from such digests by chromatographic methods.

Alternatively, human $LTC_4$ synthase polypeptides can be synthesized using an appropriate solid state synthetic procedure (Steward et al, *Solid Phase Peptide Synthesis*, Freemantle, San Francisco, Calif., 1968). A preferred method is the Merrifield process (Merrifield, *Recent Progress in Hormone Res.* 23:451, 1967). The activity of these peptide fragments may conveniently be tested using, for example, a COS-7 expression assay as described herein.

The human $LTC_4$ synthase polypeptide sequences of the invention also include non-human homologues of the amino acid sequence of SEQ ID NO.:2. The non-human $LTC_4$ synthases of the invention may be prepared by recombinant nucleic acid expression techniques or by chemical synthesis using standard peptide synthesis techniques.

Also within the scope of the invention are nucleic acid sequences or proteins encoded by nucleic acid sequences derived from the same gene but lacking one or more structural features as a result of alternative splicing of transcripts from a gene that also encodes the complete human $LTC_4$ synthase polypeptide gene, as defined previously.

Nucleic acid sequences complementary to DNA or RNA sequences encoding $LTC_4$ synthase or a functionally active portion(s) thereof are also provided. In animals, particularly transgenic animals, RNA transcripts of a desired gene or genes may be translated into polypeptide products having a host of phenotypic actions.

In a particular aspect of the invention, antisense oligonucleotides and oligonucleotide analogs can be synthesized. Antisense oligonucleotides or analogs specifically bind to the complementary sequence of either pre-mRNA or mature mRNA, as defined by Watson-Crick base pairing, inhibiting the flow of genetic information from DNA to protein. These oligonucleotides may have activity in their own right, such as antisense reagents which block translation or inhibit RNA function. Where $LTC_4$ synthase is to be produced utilizing the nucleotide sequences of this invention, the DNA sequence may also be in an inverted orientation which gives rise to a negative sense RNA on transcription. This RNA is not capable of being translated to the desired human $LTC_4$ synthase polypeptide product, as it is in the wrong orientation and would give a nonsensical product if translated, thus modulating production of $LTC_4$ synthase. In this regard, "oligonucleotide" refers to a polynucleotide formed from naturally occurring bases and cyclofuranasyl groups joined by phosphodiester bonds. "Oligonucleotide analog", refers to moieties which function similarly to anti-sense oligonucleotides but which have non-naturally-occurring portions which are not closely homologous. Thus, oligonucleotides may have altered sugar moieties or inter-sugar linkages. Exemplary are phosphorothioate and other sulfur linkages species known in the art. Such analogs are functional equivalents of the anti-sense oligonucleotides of the invention.

The most direct effect that antisense oligonucleotides have on intact cells that can be easily quantified is specific inhibition of $LTC_4$ synthase activity (see Example 1).

E. Expression of Polypeptide

The present invention also permits the expression, isolation, and purification of the human $LTC_4$ synthase polypeptide. A human $LTC_4$ synthase nucleotide sequence may be cloned or subcloned using any method known in the art. It will be appreciated that some post-translational events such as glycosylation, phosphorylation, and/or subunit assembly may not be carried out in the same manner in all eukaryotic cells. The preferred expression systems utilize mammalian cells and cell lines.

A large number of vector-mammalian host systems known in the art may be used. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant human $LTC_4$ synthase molecules can be introduced into host cells via transformation, transfection, infection, electroporation, etc. Generally, introduction of human $LTC_4$ synthase molecules into a host is accomplished using a vector containing human $LTC_4$ synthase DNA under control of regulatory regions of the DNA that function in the host cell.

In one method of expressing human $LTC_4$ synthase polypeptide, the cDNA that corresponds to the entire coding region (e.g., SEQ ID NO.:1) is moved by way of a eukaryotic expression vector into cells derived from the simian kidney (e.g., COS-7 cells). Expression is monitored after transfection by measuring the production of $LTC_4$ synthase (see Examples 1 and 3). The details of this experimental approach for transfection, selection and characterization of the $LTC_4$ synthase are similar to those that have been used previously for other polypeptides (see, for example, Bimir et al., *Biochim. Biophys. Acta* 1048:100, 1990, the entire contents of which are incorporated herein by reference).

Once the polypeptide is expressed, it may be isolated and purified by standard methods including chromatography (e.g., ion exchange, affinity, and sizing column chromatography), centrifugation, differential solubility, or by any other standard technique for the purification of proteins. In particular, $LTC_4$ synthase may be isolated by binding to an affinity column comprising antibodies to $LTC_4$ synthase bound to a stationary support.

F. Preparation of Antibodies to the Polypeptide

The term "antibodies" is meant to include monoclonal antibodies, polyclonal antibodies and antibodies prepared by recombinant nucleic acid techniques that are selectively reactive with human $LTC_4$ synthase polypeptide. The term "selectively reactive" refers to those antibodies that react with one or more antigenic determinants of human $LTC_4$ synthase polypeptide, and do not react with other transporter polypeptides. Determinants usually consist of chemically active surface groupings of molecules such as amino acids or sugar side chains and have specific three dimensional structural characteristics as well as specific charge characteristics. Antibodies include those raised against the human polypeptide of SEQ ID NO.:2 and intended to cross-react with other human homologs but not with non-human $LTC_4$ synthase. These antibodies may be useful for diagnostic applications. Other antibodies include those raised against non-human (i.e., mouse or goat) $LTC_4$ synthase, which antibodies may be generally used for research purposes. These antibodies include those raised against short, synthetic peptides of the non-human sequence.

Antibodies may be raised against human $LTC_4$ synthase and isolated by standard protein purification methods. Generally, a peptide immunogen is first attached to a carrier to enhance the immunogenic response. Although the peptide immunogen can correspond to any portion of the amino acid sequence of the human $LTC_4$ synthase or to variants of the sequence, such as the amino acid sequences corresponding to the primers and probes described, certain peptides are more likely than others to provoke an immediate response. For example, a peptide including the C-terminal amino acid is more likely to generate an antibody response.

Other alternatives to preparing antibodies reactive with human LTC, synthase include: immunizing an animal with a protein expressed by a procaryotic (e.g., bacterial) or eukaryotic cell, which cell includes the coding sequence for: (i) all or part of human $LTC_4$ synthase; or (ii) the coding sequence for all or part of a non-human (i.e., mouse) $LTC_4$ synthase. Antibodies can also be prepared by immunizing an animal with whole cells that are expressing all or a part of a cDNA encoding the human $LTC_4$ synthase polypeptide. For example, cDNA encoding the $LTC_4$ synthase of the present invention (e.g., SEQ ID NO.:1) may be expressed in a host using standard techniques (see Sambrook et al., *Molecular Cloning: A Laboratory Manual,* 2nd ed., Cold Spring Harbor Press, New York, 1989), or methods described herein, such that preferably 5–20% of the total of protein recovered is human $LTC_4$ synthase polypeptide. Proteins are electrophoresed using PAGE, the appropriate band cut, the protein eluted, and prepared for immunization.

Mice are immunized twice intraperitoneally with 20 micrograms protein immunogen per mouse. Their sera is tested for antibody activity by immunohistology or immunocytology on any $LTC_4$ synthase expressing cell system (e.g., transfected COS-7 cells) and/or by immunoassay with the expressed human $LTC_4$ synthase polypeptide. For immunohistology, a biotin-conjugated anti-mouse immunoglobulin may be used followed by avidin-peroxidase, and a chromogenic peroxidase substrate. Such preparations are commercially available; for example, from Zymad Corp., San Francisco, Calif. Animals with serum antibodies are sacrificed three days later and their spleens taken for fusion and hybridoma production, as above. Positive supernatants are tested as above and by, for example, Western blot analysis.

To further improve the likelihood of producing an anti-human $LTC_4$ synthase immune response, the amino acid sequence of the $LTC_4$ synthase may be analyzed in order to identify portions of the molecule which may be associated with increased immunogenicity. For example, the amino acid sequence may be subjected to computer analysis to identify surface epitopes which present computer-generated plots of antigenic index, an amphophilic helix, amphophilic sheet, hydrophilicity, and the like. Alternatively, the deduced amino acid sequences of $LTC_4$ synthase from different species could be compared, and relatively non-homologous regions identified. These non-homologous regions would be more likely to be immunogenic across various species.

For preparation of monoclonal antibodies directed toward human $LTC_4$ synthase polypeptide, any technique which provides for the production of antibody molecules by continuous cell lines and culture may be used. For example, the hybridoma technique originally developed by Kohler et al. (*Nature* 256:495, 1973), as well as the trioma technique, the human B-cell hybridoma technique (Kozbor et al., *Immunology Today* 4:72), and the EBV-hybridoma technique to produce human monoclonal antibodies, and the like, are within the scope of the present invention (see, generally, Larrick et al., U.S. Pat. No. 5,001,065 and references cited therein. Further, single-chain antibody (SCA) methods are also available to form anti-human $LTC_4$ synthase antibodies (Ladner et al., U.S. Pat. Nos. 4,704,694 and 4,976,778).

Recent developments in production of human monoclonal antibodies, involving insertion of human heavy and light-chain genetic loci into mice in which endogenous production of heavy and light chains is disrupted, has lead to mice that can synthesize human antibodies specific for human antigens, and can be employed to produce hybridomas making human antibodies (see Lonberg et al., *Nature* 368:856, 1994); and Green et al., *Nature Genet.* 7:13, 1994, each of which is incorporated herein by reference).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to anti-human $LTC_4$ synthase polypeptide monoclonal antibodies or other molecules of the invention (see, for example, "Conjugate Vaccines", *Contributions to Microbiology and Immunology*, Cruse et al. (eds), Carger Press, New York, 1989, the entire contents of which are incorporated herein by reference).

Coupling may be accomplished by any chemical reaction that will bind the two molecules so long as the antibody and the other moiety retains their respective activities. This linkage can include many chemical mechanisms, for instance covalent binding, affinity binding, intercalation, coordinate binding and complexation. The preferred binding is, however, covalent binding. The covalent binding can be achieved either by direct condensation of existing side chains or by the incorporation of external bridging molecules. Many bivalent or polyvalent linking agents are useful in coupling protein molecules, such as an anti-human $LTC_4$ synthase monoclonal antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents (see Killen et al., *J. Immun.* 133:1335, 1984; Jansen et al., *Immunol. Rev.* 62:185, 1982; and Vitetta et al., supra).

Preferred linkers are described in the literature (see, for example, Ramakrishnan et al., *Cancer Res.* 44:201, 1984, describing use of MBS (M-maleimidobenzoyl-N-hydroxysuccinimide ester; see also, Umemoto et al. U.S. Pat. No. 5,030,719, describing use of halogenated acetyl hydrazide derivative coupled to an antibody by way of an oligopeptide linker). Particularly preferred linkers include: (i) EDC (1-ethyl-3-(3-dimethylamino-propyl)carbodiimide hydrochloride; (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6[3-(2-pyridyldithio)propionamido]hexanoate (Pierce Chem. Co., Cat #21651G); (iv) Sulfo-LC-SPDP (sulfosuccinimidyl 6[3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In other embodiments, compositions of the invention can be used as reagents in immunoassays to detect antibodies against human $LTC_4$ synthase. Immunoassays can be any of the conventional assay types. For example, a sandwich assay can be performed in which the $LTC_4$ synthase of the invention is affixed to a solid phase. A liquid sample such as bronchial fluid containing, or suspected of containing, antibodies directed against $LTC_4$ synthase is incubated with the solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin.

Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid phase and the label bound to the solid phase is measured, the amount of the label detected serving as a measure of the amount of anti-human $LTC_4$ synthase antibody present in the sample. These and other immunoassays can be easily performed by those of ordinary skill in the art using the present compositions as reagents. Such fragments are typically produced by proteolytic cleavage using enzymes such a papain or pepsin, using methods well known in the art.

Radioactive isotopes can be detected by such means as the use of a gamma counter or assimilation counter or by autoradiography (for example, Work et al., *Laboratory Techniques in Biochemistry and Molecular Biology*, North Holland Publishing Company, New York 1978).

G. Assays/Utilities

1. Identification of $LTC_4$ Synthase Modulators

The present invention allows for identification of factors that modulate $LTC_4$ synthase expression and/or activity. As will be appreciated by those of ordinary skill in the art, $LTC_4$ synthase gene expression can be regulated at any of a variety of levels including, but not limited to, transcription, splicing, mRNA nuclear export, translation, folding, dimerization and/or post-translational modification. As discussed herein, the present invention provides sensitive assays for $LTC_4$ production, and therefore provides assays that can be used to detect effects on $LTC_4$ synthase expression and/or activity. Other assays known in the art, such as Northern blots, Western blots, Differential Display, etc., may also be employed in the detection and analysis of $LTC_4$ synthase modulators. Preferred modulators are those that inhibit $LTC_4$ synthase expression and/or activity. Information provided herein regarding functional regions of the $LTC_4$ synthase protein is useful in the rational development of such inhibitors. Compounds that should preferably be screened to identify $LTC_4$ synthase inhibitors include, for example, glutathione analogs, $LTA_4$ analogs, and FLAP inhibitors; preferred inhibitors reduce $LTC_4$ synthase activity at least 2–10 fold.

Thus, the present invention provides for assay systems in which activity or activities resulting from exposure to a peptide or non-peptide compound may be detected by measuring a physiological response to the compound in a cell or cell line which expresses the molecules of the invention. A "physiological response" may comprise any biological response, including but not limited to transcriptional activation of certain nucleic acid sequences (e.g., promoter/enhancer elements as well as structural genes), translation, or phosphorylation, or the induction of human $LTC_4$ synthesis.

The present invention provides for the development of novel assay systems which may be utilized in the screening of compounds that modulate human $LTC_4$ synthase. Target cells expressing human $LTC_4$ synthase polypeptide, which are modulated (i.e., activated and/or inhibited) by the compounds, may be produced by transfection with human $LTC_4$ synthase polypeptide-encoding nucleic acid.

A convenient assay method for identifying a modulator of a human $LTC_4$ synthase polypeptide includes providing a human $LTC_4$ synthase messenger RNA in a target cell such as a mammalian COS-7 cell (e.g., by transfecting the cell with an $LTC_4$ synthase gene and allowing the transfected gene to be transcribed); incubating the cell in the presence of the modulating compound; and measuring production of $LTC_4$ synthase gene products (i.e., pre-mRNA, mRNA, or protein), for example by Northern analysis, Reverse-Transcription-coupled PCR, and/or by Western Blot analysis). Alternately of additionally, effects on $LTC_4$ production and/or activity can be measured by detecting synthesis of the product of the $LTC_4$ synthase reaction ($LTC_4$), or by using the sensitive $LTC_4$ synthase assay described herein. In particular, one can screen many compounds of interest in a short period of time using this sensitive $LTC_4$ synthase assay.

An exemplary assay method for identifying a modulator of a human $LTC_4$ synthase polypeptide may include providing a target cell containing an isolated nucleotide sequence that encodes a human $LTC_4$ synthase polypeptide; maintaining the target cell under conditions and for a time sufficient for the $LTC_4$ synthase to be expressed in the target cell; exposing the target cell to a compound suspected of modulating $LTC_4$ synthase activity; measuring a property of the target cell in the presence of the modulator; and comparing this property to that of a target cell in the absence of the modulator but containing the isolated nucleotide sequence.

An altered property of the target cell exposed to the modulator is indicative of a modulating effect of the compound. Transfection of mammalian cell lines with eukaryotic DNA is well known and the techniques have been described extensively in the literature (see, for example Sambrook et al., *Molecular Cloning: A Laboratory Manual*, 2nd ed., Cold Spring Harbor Press, New York, 1989, the entire contents of which are incorporated herein by reference).

Once target cell lines are produced or identified, it may be desirable to select for cells which are exceptionally sensitive to a particular compound. Such target cells may express large amounts of human $LTC_4$ synthase polypeptide. Target cells expressing a relative abundance of the polypeptide could be identified by selecting target cells which, when incubated with a $LTA_4$, produce a relatively higher degree of $LTC_4$ synthesis. Alternatively, cell lines which are exceptionally sensitive to a compound may exhibit a relatively strong biological response, such as a sharp increase in immediate early gene products such as c-fos or c-jun, in response to $LTC_4$ synthase expression. By developing assay systems using target cells which are extremely sensitive to a compound, the present invention provides for methods of screening for low levels of human $LTC_4$ synthase activity.

In particular, using recombinant DNA techniques, the present invention provides for human $LTC_4$ synthase target cells which are engineered to be highly sensitive to modulating compounds. For example, the human $LTC_4$ synthase gene, cloned according to the methods set forth above, may be inserted into cells which naturally express $LTC_4$ synthase such that the recombinant human $LTC_4$ synthase gene is expressed at high levels.

The present invention also provides techniques by which $LTC_4$ synthase modulators can be identified in assays that do not rely on production of $LTC_4$ gene products. For example, transcriptional regulatory factors that recognize promoter elements flanking or within the $LTC_4$ gene can be identified in "promoter-bashing" experiments of the sort that are well known in the art (see, for example, Example 8). In such experiments, promoter sequences from the $LTC_4$ gene (for example, sequences found upstream of the $LTC_4$ transcription start site (see FIG. 3) are fused to a reported gene, such as the CAT gene, and the fusion construct is then transfected into an appropriate cell.

Various fusions are made in which the promoter sequences have been altered (e.g., by substitution, deletion, addition, and/or translocation of sequences). A wide variety of procedures for altering DNA sequences are well known in the art including, for example, site-directed mutagenesis, PCR-directed mutagenesis, DNA cleavage, etc. (see, for example, McPherson, *Directed Mutagenesis*, IRL Press at Oxford University Press, 1991; Innis et al., *PCR Protocols: A Guide to Methods and Applications*, Academic Press, San Diego, Calif. 1990; Perbal, *A Practical Guide to Molecular Cloning*, 2nd ed., 1988; Wu, *Recombinant DNA Methodology*, Academic Press, San Diego, Calif., 1989). Effects of the alterations on expression of the fused gene are assayed, and transcriptional regulatory sequences are thereby identified.

As one of ordinary skill in the art are well aware, transcriptional regulatory sites are often, but not necessarily, found upstream of the transcription start site. It is therefore most desirable to include these upstream sequences in the fusion, but internal sequences and/or downstream sequences are desirably also assayed. The region of SEQ ID NO.:10 that includes the putative SP-1, AP-1, and AP-2 sites (see FIG. 3) is most desirable for use in such assays.

Protein factors that regulate transcription can also be identified according to the present invention, for example, by gel shift assays. In such studies, fragments of the $LTC_4$ synthase promoter region are incubated with extracts from cells in which the $LTC_4$ synthase gene is expressed, so that fragments that include protein binding sites bind their appropriate proteins and are subsequently retarded during gel electrophoresis. Such gel shift assays are desirably performed in conjunction with the gene fusion transcriptional assays described above and/or with in vivo or in vitro footprinting assays, crosslinking studies, and the like. Once a DNA fragment has been identified that includes a transcription factor binding site, the site is precisely mapped within the fragment (e.g., by interference, footprinting, and/or crosslinking studies, or the like), and the protein factor is further purified using known techniques such as column chromatography (including affinity chromatography with the relevant DNA site (see, for example, Scopes, *Protein Purification: Principles and Practice*, 2nd ed., Springer-Verlag, New York, N.Y., 1987).

2. Overproduction or Depletion of $LTC_4$ Synthase

The present invention also provides for experimental model systems for studying the physiological role of the native human $LTC_4$ synthase polypeptide. In these model systems, human $LTC_4$ synthase polypeptide, peptide fragment, or a derivation thereof, may be either supplied to the system or produced within the system. Such model systems could be used to study the effects of human $LTC_4$ synthase excess or depletion. The experimental model systems may be used to study the effects of increased or decreased response to ligand in cell or tissue cultures, in whole animals, or in particular cells or tissues within whole animals or tissue culture systems, or over specified time intervals (including during embryogenesis).

In additional embodiments of the invention, a human $LTC_4$ synthase sequence may be used to inactivate the endogenous gene by homologous recombination, and thereby create a human $LTC_4$ synthase-deficient cell, tissue, or animal. For example, and not by way of limitation, a recombinant human $LTC_4$ synthase nucleotide sequence may be engineered to contain an insertional mutation (e.g., the neo gene) which, when inserted, inactivates transcription of human $LTC_4$ synthase polypeptide. Such a construct, under the control of a suitable promoter operatively linked to the human $LTC_4$ synthase nucleotide sequence, may be introduced into a cell by a technique such as transfection, transduction, injection, etc. In particular, stem cells lacking an intact human $LTC_4$ synthase gene may generate transgenic animals deficient in human $LTC_4$ synthase polypeptide. A "transgenic animal" is an animal having cells that contain DNA which has been artificially inserted into a cell, which DNA becomes part of the genome of the animal which develops from that cell. The preferred DNA encodes for $LTC_4$ synthase and may be entirely foreign to the transgenic animal or may be homologous to the natural $LTC_4$ synthase of the transgenic animal, but which is inserted into the animal's genome at a location which differs from that of the natural homolog.

In a specific embodiment of the invention (see Example 5), the endogenous human $LTC_4$ synthase gene of a cell may be inactivated by homologous recombination with a mutant human $LTC_4$ synthase gene to form a transgenic animal lacking the ability to express human $LTC_4$ synthase polypeptide. In another embodiment, a construct can be provided that, upon transcription, produces an "anti-sense" nucleic acid sequence which, upon translation, will not produce the required human $LTC_4$ synthase polypeptide.

In a further embodiment of the invention, $LTC_4$ synthase expression may be reduced by providing human $LTC_4$ synthase polypeptide-expressing cells, preferably in a transgenic animal, with an amount of human $LTC_4$ synthase polypeptide anti-sense RNA or DNA effective to reduce expression of human $LTC_4$ synthase polypeptide.

A transgenic animal (preferably a non-human mammal) can also be provided with a human $LTC_4$ synthase DNA sequence that also encodes a repressor protein that can bind to a specific DNA sequence of human $LTC_4$synthase polypeptide, thereby reducing ("repressing") the level of transcription of human $LTC_4$ synthase DNA.

Transgenic animals of the invention which have attenuated levels of $LTC_4$ synthase expression have general applicability to the field of transgenic animal generation, as they permit control of the level of expression of genes.

3. Analysis of $LTC_4$ Synthase Expression

According to the present invention, human $LTC_4$ synthase probes may be used to identify cells and tissues of transgenic animals which lack the ability to transcribe human $LTC_4$ synthase nucleotide sequences. $LTC_4$ synthase expression may be evidenced by transcription of human $LTC_4$ synthase mRNA or production of human $LTC_4$ synthase polypeptide, determined using probes as described above. One variety of probe which may be used to detect human $LTC_4$ synthase expression is a nucleic acid probe, containing at least a portion of SEQ ID NO.:1. Detection of human $LTC_4$ synthase-encoding mRNA may be easily accomplished by any method known in the art, including, but not limited to, in situ hybridization, Northern blot analysis, or PCR related techniques. Probes of SEQ ID NO.:1 or derived therefrom, may be used to screen tissues of patients with, for example, asthma in order to detect the presence of aberrant $LTC_4$ synthase-encoding mRNA. Another variety of probe which may be used is an anti-human $LTC_4$ synthase antibody to screen patients for abnormal levels of the enzyme.

The above-mentioned probes may be used experimentally to identify cells or tissues which hitherto had not been shown to express human $LTC_4$ synthase polypeptide. Furthermore, these methods may be used to identify the expression of $LTC_4$ synthase by aberrant tissues, such as malignancies.

4. Diagnostic Methods

As discussed above, the present invention encompasses the discovery that the human $LTC_4$ synthase gene is on the long arm of chromosome 5, in a region where many genes related to the asthmatic phenotype are located. The inflammatory changes associated with bronchial asthma implicate these genes. Specifically, biopsies show that bronchial asthma is characterized by degranulation of mast cells and by infiltration of eosinophils and TH2 T cells, all of which express markers of activation (Azzawi et al., *Am. Rev. Respir. Dis.* 142:1407, 1990; Djukanovic et al, *Am. Rev. Respir. Dis.* 142:863, 1990). Interestingly, interleukin-3 (IL-3), IL-5, and GM-CSF, whose genes are located on the long arm of chromosome 5, are involved in regulating eosinophilopoiesis (Boyce et al., *J. Exp. Med.* 182:49, 1995; Dvorak et al., *Lab. Invest.* 61:116, 1989; Saito et al., *Proc. Natl. Acad. Sci. USA* 85:2288, 1988) and also act on mature eosinophils to attenuate steroid-induced apoptosis (Her et al., *J. Clin. Invest.* 88:1982, 1991). Furthermore, these cytokines convert eosinophils to a phenotype similar to that associated with disease in which the cells are primed for ligands initiated generation of $LTC_4$ and target cell cytotoxicity (Rothenberg et al., *J. Clin. Invest.* 81:1986, 1988; Owen, *J. Exp. Med.* 166:129, 1987; Owen et al., *J. Exp. Med.* 170:343, 1989).

IL-4, whose gene is also within the chromosome 5 cluster, mediates immunoglobulin isotype switching in general and IgE biosynthesis in B cells in particular (Lebman et al., *J. Exp. Med.* 168:853, 1988). IgE sensitizes mast cells and basophils through their high-affinity receptors for allergen specific activation, providing an additional mechanism for $LTC_4$ generation. Importantly, IL-4 perpetuates the inflammatory reaction by favoring T cell maturation and differentiation to the TH2 phenotype, which provides IL-4 and the eosinophilopoietic cytokine triad (Mossman et al., *Adv. Immunol.* 46:111, 1989).

Thus, in addition to $LTC_4$ synthase's biological activity, the chromosomal localization of its gene implicates it in the asthmatic response. Substantial clinical evidence supports the linkage of specific allelic oligonucleotide markers from the region of chromosome 5 to which the present invention has localized the $LTC_4$ synthase gene with the atopic/asthmatic state.

Specifically, both atopy, a heritable condition in which specific IgE is synthesized after exposure to specific allergens, and bronchial hyperresponsiveness, a condition that is defined by compromised pulmonary function in response to environmental stimuli or concentrations of defined agonists that are inactive in the unaffected population and that correlates with circulating levels of total IgE in individuals with asthma, demonstrate significant linkage to the IL-4 gene (Postma et al., *N. E. J. Med.* 333:894, 1995). Fibroblast growth factor-acidic (FGFA) and CSF-1-receptor have also been shown by linkage analysis to be disproportionately associated with bronchial hyperresponsiveness in sibling pairs (Levitt et al., *Clin. Exp. Allerg.* 25:119, 1995). Specific polymorphisms (a C to T exchange at position −590 from the ORF) have been identified in the enhancer sequences of IL-4 and correlate with increased IL-4 level activity manifested by higher total serum IGE in atopic asthmatic kindreds (Rosenwasser et al., *Clin. Exp. Allerg.* 25:74, 1995).

Furthermore, the immediate improvement of pulmonary function in individuals with asthma who receive an initial dose of an agent or agents that are devoid of intrinsic bronchodilatory activity but selectively attenuate the formation or action of the cysteinyl leukotrienes indicates that chronic overproduction of the cysteinyl leukotrienes occurs in the natural disease (Israel et al., *Ann. Int. Med.* 119:1059, 1993). As $LTC_4$ synthase catalyzes formation of the parent of these cysteinyl leukotrienes, and the present invention demonstrates that the $LTC_4$ synthase gene is localized to a chromosomal region known to be associated with bronchial asthma, the, present invention provides information relevant to a diagnostic assay for susceptibility to bronchial asthma.

First of all, the present invention allows identification of sequence polymorphisms within the $LTC_4$ synthase gene that correlate with bronchial asthma (see Example 7). For example the genomic localization information provided herein allows the $LTC_4$ synthase gene, or portions thereof, to be cloned and sequenced, according to known techniques, from individuals with asthma and those without. Sequencing alterations that correlate with asthma can therefore be detected. As will be recognized by those of ordinary skill in the art, direct sequence analysis is not required for polymorphism detection; other techniques, such as single-strand conformational polymorphisms analysis and denaturing polyacrylamide gel electrophoresis are available in the art and could readily be employed (see, for example, Hayashi et al., *PCR Met. App.* 1:34, 1992; Grompe et al., *Nature Genetics* 5:111, 1993, each of which is incorporated herein by reference; see also Example 7).

For example, as described in Example 7, a set of $LTC_4$ synthase-specific primer pairs can be designed for use in polymerase chain reaction-single stranded conformational polymorphisms analysis (see Hayashi et al., supra). Preferably, the primer pairs span approximately 100–200 base paris, as product bands of this size are most useful for polymorphism identification. Primer pairs that amplify any region of the $LTC_4$ synthase gene sequence can be utilized, and the most thorough approach to identifying polymorphisms involves designing primer sets for all regions of the gene. One of ordinary skill in the art will recognize that polymorphisms may be found in coding sequences, regulatory sequences, splicing sequences, or other signal sequences, and will also recognize that, in some cases, deletions, additions, or translocations of nucleic acid sequences may have occurred.

Once sequence alterations that correlate with asthma have been identified, any of a variety of techniques can be used to screen individuals for the presence of asthma-associated sequence alterations in the $LTC_4$ synthase gene. For example, probes can be designed that hybridize with asthma-associated but not with normal $LTC_4$ synthase gene sequences; PCR primers can be designed that will hybridize productively to normal but not asthma-associated sequences, so that production of a PCR product band serves as a diagnostic for asthma susceptibility; primer sets can be designed to detect sequences in a ligase chain reaction (LCR) (see, for example, Barany *Proc. Natl. Acad. Sci. USA* 88:189, 1991; Barany *PCR Met. App.* 1:5, 1991), etc. Perhaps the most straightforward diagnostic would employ exactly the PCR-single stranded conformational analysis used to identify the asthma-associated polymorphism in the first place.

H. Pharmaceutical Compositions

Those of ordinary skill in the art will recognize that modulators of human $LTC_4$ synthase may have potential therapeutic applications. The compositions and assays described herein, by modulating synthesis of $LTC_4$, can provide clinicians with strategies for the treatment of patients with inflammatory conditions such as cardiac ischemia, anaphylactic shock, cold-induced asthma, exercise-induced asthma, aspirin-induced asthma, and allergic rhinitis. Therefore, the development of drugs which selectively inhibit human $LTC_4$ synthesis is expected to provide an important advantage. Full-length $LTC_4$ synthase, modulators of the synthase, functional equivalents, modifications, and/or nucleic acids capable of encoding them may be used in pharmaceutical compositions.

An exemplary pharmaceutical composition comprises a therapeutically effective amount of active ingredient(s) (e.g., $LTC_4$ synthase, or modification thereof and/or a nucleic acid capable of encoding them) and optionally includes a pharmaceutically-acceptable and compatible carrier(s). It is contemplated that pharmaceutical compositions comprising nucleic acids that are capable of encoding full-length $LTC_4$ synthase or modification thereof be used in gene therapy procedures.

The term "pharmaceutically-acceptable and compatible carrier" as used herein, and described more fully below, refers to (i) one or more compatible solid or liquid filler diluents or encapsulating substances that are suitable for administration to a human or other animal, and/or (ii) a system, such as a retroviral vector, capable of delivering a nucleic acid to a target cell.

In the present invention, the term "carrier" thus denotes an organic or inorganic ingredient, natural or synthetic, with which the active ingredient is combined to facilitate application. The term "therapeutically-effective amount" is that amount of the present pharmaceutical composition that produces a desired result or exerts a desired influence. In particular, a "therapeutically-effective" amount of the pharmaceutical compositions of the present invention is an amount that detectably inhibits or enhances activity of $LTC_4$ synthase in vivo or in vitro. Those of ordinary skill in the art will recognize that modulators of human $LTC_4$ synthase may have potential therapeutic applications. Any $LTC_4$ synthase assay may be used to detect inhibition or enhancement of $LTC_4$ synthase, including those $LTC_4$ assays described herein (see Example 1).

The term "compatible", as used herein, means that the components of the pharmaceutical compositions are capable of being commingled with the nucleic acid and/or polypeptides of the present invention, and with each other, in a manner such that there is no interaction that would substantially impair the desired pharmaceutical efficacy.

The molecules of the invention may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group.

The pharmaceutical compositions of the invention include those suitable for oral, rectal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. The term "parenteral" includes subcutaneous injections, intravenous, intramuscular, intrasternal injection or infusion techniques.

Pharmaceutical compositions of the present invention may be in a form suitable for oral administration. For example, pharmaceutical compositions of the invention may be presented as capsules, cachets, tablets, troches, lozenges, aqueous or oily suspensions, dispersible powders or granules, emulsions, hard or soft capsules, or syrups or elixirs. Capsules, cachets, tablets, and lozenges may contain the active ingredient in liposomes or as a suspension in an aqueous liquor or non-aqueous liquid such as a syrup, an elixir, or an emulsion.

Aqueous suspensions may contain the active materials in admixture with excipients suitable for the manufacture of aqueous suspensions. Such excipients may be (1) suspending agents such as sodium carboxymethoylcellulose, methylcellulose, hydroxypropylmethylcellulose, sodium alginate, polyvinylpyrrolidone, gum tragacanth and gum acacia; (2) dispersing or wetting agents which may be (a) a naturally-occurring phosphatide such as lecithin, (b) a condensation product of an alykylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

The pharmaceutical compositions of the invention may also be in the form of oil-in-water emulsions. The oily phase may be a vegetable oil such as olive oil or arachis oils, or mineral oil such as liquid paraffin or mixture thereof.

Suitable emulsifying agents may be (1) naturally-occurring gums such as gum acacia and gum tragacanth, (2) naturally-occurring phosphatides such as soy bean and lechithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic monoor diglycerides. In addition, fatty acids such as oleic acid find use in the preparation of injectibles.

The pharmaceutical compositions of the invention may include a sustained release delivery system. Preferred sustained release delivery systems are those that can provide for release of the active compounds in sustained release pellets or capsules. Many types of sustained release delivery systems are available (see, for example, U.S. Pat. No. 5,252,318). These include, but are not limited to, (i) erosional systems in which the active compounds are contained within a matrix (see, for example, U.S. Pat. Nos. 4,452,775; 4,667,014; 4,748,024; and 5,239,660; and (ii) diffusional systems in which the active compounds permeate at a controlled rate through a polymer (see, for example, U.S. Pat. Nos. 3,832,252; and 3,854,480).

Alternatively, the pharmaceutical compositions of the invention may include a delivery system such as, for example, a liposome delivery system. Liposomes are single- or multi-compartmented bodies obtained when lipids are dispersed in aqueous dispension. The walls of the compartments are membranes that are composed of a continuous lipid bi-layer that encloses an inner space. Liposomes can be used, for example, to encapsulate and deliver pharmaceutical agents.

EXAMPLES

Example 1

Cloning and Sequencing of Human $LTC_4$ Synthase cDNA

Materials and Methods

PROTEINS AND CELLS: $LTC_2$ (see Nicholson et al., Eur. J. Biochem., 209:725—FIG. 6B) and $LTA_4$-methyl ester were-synthesized by Dr. Bernd Spur while he was at Harvard University. MK-886, mouse monoclonal $LTC_4$ antibodies and a FLAP cDNA probe (A. Ford-Hutchinson, Merck Frosst) and A79175 (G. Carter, Abbott Laboratories) were generous gifts. Total RNA from human eosinophils developed in vitro from human umbilical cord blood mononuclear leukocytes cultured for 28 days with human recombinant interleukin 3 and interleukin 5 was provided by Joshua Boyce (Harvard Medical School). $LTA_4$ was hydrolyzed as described by Maycock et al., J. Biol. Chem. 257: 13911, 1982. $LTC_2$-LC-Biotin was synthesized by coupling $LTC_2$ with NHS-LC-Biotin (1:10 ratio) at pH 7.4 in Tris-HCl buffer at room temperature for 120 min with a conjugation rate of over 95%. The mixture was purified by high performance liquid chromatography (HPLC) with an isocratic solvent system containing 24.9% $H_2O$, 1% acetic acid, 75% methanol, pH 5.0.

KG-1 cells and Raji cells (American Type Culture Collection) were cultured in RPMI-1640 supplemented with 10% fetal calf serum and 15 $\mu$g/ml gentamicin under a humidified atmosphere of 95% $O_2$/5% $CO_2$ at 37° C. COS-7 cells were cultured in RPMI1640 supplemented with 10% heat-inactivated fetal calf serum and 15 µg/ml gentamycin under identical culture conditions. Human PMN and eosinophils were obtained from normal volunteers and isolated as described by Weller et al., *Proc. Nat. Acad. Sci. USA*, 80:7626, 1983.

mRNA ISOLATION AND pcDNA3 LIBRARY CONSTRUCTION: Messenger RNA (mRNA) was prepared from $2 \times 10^8$ KG-1 cells with a FastTrack mRNA (InVitrogen, San Diego, Calif.) isolation kit according to the manufacturer's instructions. A plasmid cDNA library (pcDNA) was constructed from the mRNA by InVitrogen briefly as follows: The first strand cDNA was synthesized from mRNA using Not oligo T priming. cDNAs were sized by agarose gel electrophoresis, and those greater than 500 base pairs (bp) were ligated with a EcoRI/BstXI adaptor and cloned into the pcDNA3 mammalian expression vector (obtained from InVitrogen, San Diego, Calif.). The pcDNA3 library was used to transform *E. coli* strain Top 10F[1] with a complexity of 1.76 million original clones.

DEVELOPMENT OF cDNA LIBRARY: Exactly 96 pools of 2500 *E. coli* strain Top 10F[1] colonies each were aliquoted from the KG-1 pcDNA3 library and grown in 100 µl SB medium (containing 5 g/l NaCl, 32 g/l tryptone, 20 g/l yeast extract, and 50 mg/l ampicillin) in a 96-well flat-bottom microtiter plate at 37° C. overnight to amplify each pool. Then, 20-µl samples of bacterial culture from each well were transferred separately into a 10-ml conical tube containing 3 ml of SB medium, and the remaining 80 µl were frozen at –20° C. in 15% glycerol for later rounds of screening. Bacterial cultures in the conical tubes were grown at 37° C. for 18 h, and a 1.5-ml sample of each was subjected to alkaline hydrolysis to develop miniature preparations of plasmids (see, Freeman et al., *J. Immunol.*, 143:2714, 1989, incorporated herein by reference). Plasmids were dissolved in 25 µl of Tris-EDTA buffer and a 5-µl sample of each was used for COS cell transfection.

TRANSFECTION AND SCREENING: COS-7 cells were transfected with plasmid DNA from the KG-1 pcDNA3 library using a DEAE-dextran technique as described by Seed et al., *Proc. Nat. Acad. Sci. USA*, 84:3365, 1987. Briefly, COS-7 cells at about 50% confluence are transfected in 1.5 ml of Dulbecco's or Iscove's modified Eagle's medium (DMEM or IMDM) with 10% NuSerum (Collaborative Research, Waltham, Mass.); 400 micrograms DEAE-dextran per ml; 100 micromolar chloroquine diphosphate; and miniprep plasmid DNA.

Seventy-two hours after transfection, the COS cells were harvested by trypsinization. Twenty thousand cells from each plate were resuspended in 500 µl of culture medium and incubated with 25 µM $LTA_4$ substrate for 30 min on ice to allow the synthesis of intracellular leukotriene product ($LTC_4$). Cells were washed and resuspended in 37° C. medium containing 20 mM serine-borate for 10 min to release intracellular $LTC_4$ into the medium. Cells were pelleted, and the $LTC_4$ in the supernatants was measured by immunoassay.

A positive pool was defined as having produced an amount of $LTC_4$ that was 2 standard deviations above the mean value for all plates in that particular transfection experiment. Any pools that met the definition for positive were simultaneously rescreened in duplicate, and the amounts of $LTC_4$ produced were compared to the mean of 10 controls that were transfected with irrelevant plasmid DNA (CD40 plasmid DNA). A positive pool at this stage was defined as producing an amount of $LTC_4$ that was 5 standard deviations above the mean of the control transfectants.

Once a positive pool was identified, its frozen stock from the 96-well microtiter plate was thawed, titered, and subdivided into smaller pools of about 50 colonies each; these pools were distributed to SB-agar plates containing 50 µg/ml ampicillin. After overnight growth, each plate was replicated by overlaying a nitrocellulose membrane and transferring the membrane to an empty plate. Each membrane was then submerged in 10 ml of SB medium and subjected to intermittent agitation for 10 min by pipeting SB medium to elute the bacterial colonies from the nitrocellulose membranes. The replicate eluted colonies were grown at 37° C. overnight for plasmid preparation. The original plates were cultured at 37° C. for an additional 6 h to replenish the bacterial colonies and were held at 4° C. until a final screening by plasmid preparations of individual colonies of a positive plate.

For these later rounds of screening, samples of transfected COS cells ($5 \times 10^5$ cells each) were incubated with 20 µM $LTA_4$-methyl ester (ME) substrate for 10 min at 37° C. in the presence of 20 mM serine-borate. Reactions were terminated by the addition of 3 volumes of methanol containing prostaglandin $B_2$ ($PGB_2$). Total $LTC_4$-ME was quantitated by reverse phase-high performance liquid chromatography (RP-HPLC) to confirm the identity of the product by retention time and UV spectra.

$LTA_4$-ME was used as substrate instead of the free acid because it provides a high $V_{max}$ (Yoshimoto et al., *J. Clin. Invest.*, 81:866, 1988) and because we had devised an automated HPLC system to detect and quantitate $LTC_4$-ME every 18 min. This assay had the additional advantage of confirming that the product released by transfected COS cells after incubation with $LTA_4$-ME was $LTC_4$-ME based upon its retention time and the on-line UV spectra.

DNA SEQUENCING: Plasmids were prepared with a Nucleobond isolation kit (Nest) and were sequenced as described by Sanger et al., *Proc. Nat. Acad. Sci. USA*, 74:5463, 1977 using dye-labeled dideoxy nucleotides as terminators. Samples were analyzed on an Applied Biosystems model 373A automated DNA sequencer at the Molecular Biology Core Facility, Dana Farber Cancer Institute (see also, Smith et al., *Nature* 321:674, 1986). Double strand sequencing was performed on one clone producing $LTC_4$ activity (clone 56-12-8), whereas the other two clones producing $LTC_4$ activity (clones 56-13-25 and 56-16-3) were sequenced on the sense strand only.

REVERSE PHASE-HPLC: HPLC was carried out with a model 126 dual pump system and model 167 scanning UV detector (Beckman Instruments) controlled by an IBM PS2/50 computer using Beckman System Gold software. Samples were applied to a 5-µm 4.6×250-mm C18 Ultrasphere reverse phase column (Beckman Instruments) equilibrated with a solvent of methanol/acetonitrile/water/acetic acid (10:15:100:0.2, v/v), pH 6.0 (solvent A). After injection of the sample, the column was eluted at a flow rate of 1 ml/min with a programmed concave gradient (System Gold curve 6) to 30% solvent A and 70% pure methanol (solvent B) over 0.2 min. After 2.8 min more, solvent B was increased linearly to 90% over 2 min and was maintained at this level for an additional 10 min. UV absorbance at 280 nm and the UV spectra were recorded simultaneously. The retention times for $PGB_2$ and $LTC_4$-ME were 8.5 and 10.1 min, respectively. $LTC_4$-ME was quantitated by calculating the ratio of the peak area to the area of the internal standard $PGB_2$.

NATIVE AND RECOMBINANT PROTEIN PURIFICATION AND SEQUENCING: Subcellular localization of $LTC_4$ synthase followed the procedure of Penrose et al.,

*Proc. Nat. Acad. Sci., USA,* 89:11603, 1992, incorporated herein by reference. Briefly, native KG-1 or COS-7 cells were harvested by centrifugation at 1000×g for 10 min at 4° C. and washed in a small amount of buffer A (50 mM HEPES/5 mM 2-mercaptoethanol/1 mM EDTA (pH 7.6)). The cells were suspended in buffer containing 50 mM HEPES, 0.25 M sucrose, 5 mM 2-mercaptoethanol, 1 mM EDTA and 10% glycerol (pH 7.6) and sonicated on ice. The sonicate was centrifuged and 1000×g for 10 min to sediment cell debris. The supernatant was centrifuged at 10,000×g for 10 min, decanted to new centrifuge tubes, and spun at 100,000×g to obtain pellets containing microsomes and supernatants containing cytosol. Microsomal and cytosolic fractions were then assayed for $LTC_4$ synthase activity (see immunoassay described herein) to determine subcellular localization of $LTC_4$ synthase (i.e., microsome vs. cytosol).

Detergent-solubilized $LTC_4$ synthase from $6 \times 10^{10}$ native KG-1 cells (using 0.4% deoxycholate, 0.4% Triton X-102, 10% glycerol) was purified by S-hexylglutathione-agarose chromatography using procedures adapted from Penrose et al., *Proc. Nat. Acad. Sci., USA,* 89: above, followed by $LTC_2$ affinity chromatography. Active fractions purified from the S-hexylglutathione-agarose column were combined, concentrated (Amicon, Danvers, Mass.) and then loaded onto an $LTC_2$ affinity column equilibrated with buffer A and 0.1% Triton X-102. The column was washed with the same buffer and the enzyme was eluted with buffer A, containing 0.1% Triton X-102, 0.5 M NaCl and 5 mM reduced glutathione.

The $LTC_4$ synthase activity contained a single 18-kDa protein by sodium dodecyl sulfate-polyacrylamide gel electrophoresis ($NaDodSO_4$-PAGE) with silver staining. This fraction did not conjugate GSH to 1-chloro-2,4-dintrobenzene. A sample of the purified protein was concentrated and added to an equal volume of reducing buffer, and the mixture was boiled for 5 min. The reduced protein in this solution was bound to a polyvinylidene membrane by incubation overnight at 4° C. The bound protein was analyzed for N-terminal amino acid sequence by automated Edman degradation or was digested in situ with trypsin (Fernandez et al., *Anal. Biochem.,* 201:255, 1992). The resulting peptide mixture was separated by narrow-bore HPLC, and a prominent peptide was sequenced by automated Edman degradation on an Applied Biosystems 477A protein sequencer at the Harvard Microchemistry Department (see also, Lane et al., *J. Prot. Chem.,* 10:151, 1991).

$LTC_4$ synthase was purified from COS-7 cell transfectants by the identical sequential S-hexylglutathione and $LTC_2$ affinity chromatography procedures described above.

NORTHERN BLOT ANALYSIS: Total RNA (10 micrograms) from human eosinophils were developed in vitro were electrophoresed in formaldehyde/agarose gels, transblotted onto Zetabind and probed under conditions of high stringency (wash temperature 65° C.) with an $LTC_4$ synthase cDNA probe (nucleotides 1–520 of SEQ ID NO.:1). The probe was produced by digesting 10 micrograms of SEQ ID NO.:1 with 10 units each of EcoRI and SmaI at 37° C. overnight and separated on 1 percent agarose gel. The RNA blot was then striped and probed with cDNA derived from FLAP. Autoradiography exposure was 24 hours at –80° C. with two enhancing screens.

FUNCTIONING OF $LTC_4$ SYNTHASE IN COS CELLS: FLUORESCENCE-LINKED COMPETITIVE IMMUNOASSAY FOR $LTC_4$ SYNTHASE: This is a novel assay based, in part, on the discovery of a distinct $LTC_4$ cell transport step following biosynthesis. Release of $LTC_4$ from human eosinophils is time dependent at 37° C. but release of $LTC_4$ formed at this temperature, or even at 0° C., is fully inhibited at zero degrees, resulting in the intracellular retention of accumulated $LTC_4$. Thus, cells can be preloaded with $LTC_4$ at low temperatures (see Lam et al., *J. Biol. Chem.,* 264:12885, 1989, incorporated herein by reference).

COS cells possess a low basal capability to conjugate glutathione to $LTA_4$, perhaps due to a cytosolic glutathione S-transferase. Therefore, screening for enzymatic activity in transfected cells requires an assay that is sensitive enough to distinguish the incremental production of $LTC_4$ by a single clone within a pool. We developed a competitive fluorescence-linked immunoassay for $LTC_4$, with exquisite sensitivity and the high volume efficiency necessary for expression cloning of the $LTC_4$ synthase. In addition, the signal to background ratio for the production and release of $LTC_4$ from transfected cells was optimized by providing substrate $LTA_4$ at 4° C. This step allowed $LTA_4$ uptake and $LTC_4$ biosynthesis without release until the cells had been washed and warmed. The transfected COS-7 cells exhibited the same temperature-dependent $LTC_4$ export step(s) previously observed (see Lam et al., *J. Biol. Chem.,* id). Because of the wash step and the assay sensitivity, a signal to noise ratio was achieved that proved suitable for assaying all pools at the same cell number to minimize the plate-to-plate variation in cell numbers of transfected COS cells per plate.

$LTC_4$ synthase was generated from COS-7 cells transfected with cDNA from a KG-1 pcDNA3 mammalian KG-1 expression library, as described above. Cells were held at 4° C. to ensure intracellular retention of $LTC_4$ generated during the incubation with substrate. The temperature was then raised to 37° C. to allow for the export of $LTC_4$ into the incubation medium.

KG-1 cells were harvested by centrifugation and resuspended in Hanks' balanced salt solution (HBSS) at $10^7$ cells/ml. After warming to 37° C., NHS-LC-Biotin was added to achieve a final concentration of 350 µg/ml, and the mixture was incubated for 30 min to biotinylate the KG-1 cell membranes. The biotinylated cells were washed twice with HBSS containing 2 mg/ml bovine serum albumin (HBSA) to remove excess and un-reacted biotin and were incubated with 2 mg/ml avidin in HBSA. After 30 min, the biotin-avidin-coupled KG-1 cells were washed twice to remove excess avidin and were incubated with 600 ng/ml $LTC_2$-LC-Biotin for 30 min at 37° C. to link the $LTC_2$-biotin complex onto the cell surface via the previously bound avidin.

After washing the KG-1 cells, samples of $10^5$ cells each were then incubated either with (i) 0–200 pg of synthetic $LTC_4$ or (ii) with 5–10 µl portions of the warmed incubation medium from transfected COS cells. The incubation medium contained unknown amounts of released $LTC_4$. After incubation for 3 min, mouse monoclonal anti-$LTC_4$ antibodies were added (final dilution 1:10,000), and the KG-1 cells were incubated for 30 min at room temperature, washed, and incubated with fluorescein isothiocyanate-conjugated goat anti-mouse Fab[1] antiserum (1:30 dilution) for 40 min on ice in the dark. The cells were washed, resuspended in 1 ml of HBSA containing 1 mM EDTA, and analyzed by flow cytometry for cell surface fluorescence intensities.

This immunoassay measures the competition between released $LTC_4$ in solution and membrane bound $LTC_2$ for anti-$LTC_4$ antibodies as analyzed by decrements in binding of fluorescence-linked secondary antibody. Thus, the more $LTC_4$ that is in solution, the less antibody that will be available for binding to the $LTC_2$ on the cell surface. The immunoassay is capable of detecting as little as 2.5 pg of $LTC_4$ with a linear dose response between 10 and 100 pg of $LTC_4$.

It will be appreciated by those having ordinary skill in the art that inert materials may be substituted for KG-1 cells in this assay. That is, an inert carrier such as, for example, agarose beads may be coupled to avidin and used in the method, provided that the beads are of sufficient size to be assayed with flow cytometry. The assay described herein may be used to detect and quantify any product that can be biotinylated and linked to a carrier.

DOSE-RESPONSE ASSAY USING MK886: Cell lysates of the COS-7 cell transfectant containing SEQ ID NO.:1 were incubated with 20 micromolar $LTA_4$-ME, 20 mM GSH, 5 mM $MgCl_2$ in HEPES buffer (pH 7.6), in the presence of 0–10 micromolar MK886 for 10 minutes at room temperature. Reactions were stopped by addition of 2 volumes of methanol containing 200 ng PGB2. Samples were analyzed by RP-HPLC.

Results

EXPRESSION CLONING: Of the plasmids from the 96 pools (2500 colonies each) of the KG-1 pcDNA3 library transfected into COS-7 cells, only a single pool produced an $LTC_4$ value (207 pg/$10^4$ cells) that was 5 standard deviations above the mean (64.2±8 pg/$10^4$ cells).

This pool was divided into smaller pools of about 50 colonies each, colonies plated on SB-agar, and subjected to a second round of screening with $LTA_4$-ME as substrate. Three highly positive plates, numbers 56-12 (4,988 pg/$10^4$ cells), 56-13 (3,419 pb/$10^4$ cells), and 56-16 (3,850 pg/$10^4$ cells), were identified. COS-7 cells transfected with plasmid from other plates did not make detectable amounts of $LTC_4$-ME.

When individual colonies from each plate were grown and their plasmids prepared and transfected into COS-7 cells, only one colony producing $LTC_4$ synthase activity was identified from each plate, namely, clones 56-12-8 (7,485 pg/$10^4$ cells), 56-13-25 (6,391 pg/$10^4$ cells), and 56-16-3 (7,583 pg/$10^4$ cells).

NUCLEOTIDE SEQUENCE OF cDNA: Clone 56-12-8 contained a 694-bp insert with an open reading frame of 450 bp terminated by a TGA stop codon (SEQ ID NO.:1). The nucleotide sequence was identical for the two other clones, 56-13-25 and 56-16-3, producing $LTC_4$ synthase activity at high levels.

CONSENSUS AMINO ACID SEQUENCE OF $LTC_4$ SYNTHASE AND RNA BLOT ANALYSIS: The $LTC_4$ synthase protein obtained by sequential S-hexyl glutathione and $LTC_2$ affinity chromatography of solubilized $LTC_4$ from native KG-1 cells provided a 22 amino acid N-terminal sequence of MKDEVALLAAVTLLGVLLQAYF (SEQ ID NO.:9) that corresponds exactly to the N-terminal amino acid sequence (SEQ ID NO.:2) deduced from the cDNA of SEQ ID NO.:1. An internal peptide fragment of the protein provided a sequence of VSPPLTTGPPEFER (SEQ ID NO.:3) in which all 14 amino acid residues are identical to the deduced amino acid sequence amino acid residues 35–48 of SEQ ID NO.:2.

RNA isolated from human eosinophils developed in vitro demonstrated a 0.7-kilobase pair mRNA transcript (data not shown). The FLAP transcript in these same cells was approximately 1.0 kilobase. The 0.7-kilobase $LTC_4$ synthase mRNA transcript was also detected in total RNA from the KG-1 cells and less abundantly in peripheral blood eosinophils. No transcript was detected in human PMNs and Burkitt's lymphoma Raji cell line, which lack $LTC_4$ synthase function. When compared with FLAP mRNA transcript by autoradiography, $LTC_4$ synthase transcript is less intense than those of FLAP. The FLAP transcript in these same cells was approximately 1.0 kilobase. The 0.7-kilobase $LTC_4$ synthase mRNA transcript was also detected in total RNA from the KG-1 cells and less abundantly in peripheral blood eosinophils. No transcript was detected in human PMNs and Burkitt's lymphoma Raji cell line, which lack $LTC_4$ synthase function. When compared with FLAP mRNA transcript by autoradiography, $LTC_4$ synthase transcript is less intense than those of FLAP.

MICROSOMAL LOCALIZATION, SIZE AND INHIBITION OF FUNCTION OF THE PROTEIN EXPRESSED IN COS CELLS: When examined for subcellular localization, 87–89% (n=3) of the activity of the recombinant protein was in the microsomal fraction.

$LTC_4$ synthase purified from COS cell transfectants by sequential S-hexyl-GSH and $LTC_2$ affinity chromatography migrated as an 18-kDa protein by $NaDodSO_4$-PAGE, identical in size to the native enzyme purified from KG-1 cells (data not shown).

Lysates from transfected COS cells were analyzed for $LTC_4$, the product of conjugating reduced glutathione with 5,6-oxido-7,9-E-11,14-Z-eicosatetraenoic acid. MK-886, a FLAP inhibitor (see Dixon et al., *Nature* 343:6255, 1990 and Gillard et al., *Can. J. Physi ol. Pharmac.*, 67:456, 1989, both of which incorporated herein by reference), dose-dependently inhibited the conversion of 20 $\mu$M $LTA_4$-ME to $LTC_4$-ME by COS cell lysates with an $IC_{50}$ of less than 3 $\mu$M (data not shown ). At 10 $\mu$M, MK-886 inhibits more than 90% of the enzyme activity. In contrast, a 5-lipoxygenase inhibitor, A79175, did not affect $LTC_4$ synthase activity in COS cell lysates at a concentration of 10 $\mu$M.

Discussion $LTC_4$ synthase, an integral membrane protein that conjugates reduced glutathione (GSH) to $LTA_4$ but not to xenobiotics, provides the parent $LTC_4$ for the cysteinyl leukotriene family, and is the only biosynthetic moiety in the 5-lipoxygenase pathway that has not yet been defined by its cDNA, protein structure, or gene family. Recently, a 35-amino-acid N-terminal sequence was obtained for $LTC_4$ synthase extracted and purified from the THP-1 cell line (Nicholson et al., *Proc. Nat. Acad. Sci. USA* 90:2015, 1993). The amino acid N-terminal sequence obtained for the KG-1 cell line described herein (SEQ ID NO.:9) differed from that of the THP-1 cell line only at position 21; an internal 14 residue peptide (SEQ ID NO.:3) provided an additional amino acid sequence that corresponded to residues 35 to 48 of $LTC_4$ from KG-1 cells.

Nonetheless, the degeneracy of the nucleotides coding for the observed THP-1 sequence data is extremely high and did not provide oligonucleotide probes capable of hybridizing to clones carrying the sequence of interest using a λgt11 KG-1 cDNA library (unpublished data). We thus proceeded to expression cloning with the intent of using the available THP-1 protein sequence at the N-terminal amino acid residues for reference, but depending on enzymatic function for detection and definition of the cDNA and its amino acid sequence.

We have also demonstrated that FLAP inhibitor, MK-886, inhibits $LTC_4$ synthase activity from transfected COS cell lysates in a dose-related fashion with an $ID_{50}$ of about 3 $\mu$M. Since FLAP binds arachidonic acid for presentation to 5-lipoxygenase that is engaged in calcium-dependent membrane association (Mancini et al., *FEBS Lett.* 318:277, 1993) for synthesis of $LTA_4$, it seems plausible that the transmembrane domains of $LTC_4$ synthase homologous to FLAP will accept $LTA_4$ for conjugation with glutathione at/or in the membrane.

$LTA_4$ and reduced glutathione conjugate spontaneously in a basic microenvironment (see Radmark et al., *J. Biol.*

Chem., 12339, 1984). It may be that the putative binding of LTA$_4$ to LTC$_4$ synthase, a protein with a pI of 11.05, allows a favorable environment for the conjugation with bound or unbound glutathioine with only a modest catalytic boost. Thus, LTC$_4$ synthase may represent a member of the lipid-binding family rather than the classical glutathione S-transferase family. Irrespective of the catalytic mechanisms yet to be elucidated, it is likely that LTC$_4$ synthase represents a member of a novel gene family in which FLAP is also a member.

Example 2

Isolating a Homolog of LTC$_4$ Synthase

A portion of the human LTC$_4$ synthase gene is amplified from human eosinophil DNA using the polymerase chain reaction technique (Saiki et al., Science 230:1350, 1985) using Not1-Sal1 sites in the PCR primers. The 100 μl reaction contains 10 mM Tris-HCl pH 8.3, 50 mM KCl, 0.001% (w/v) Gelatin, 2 mM MgC$_{12}$, 200 μM dNTPs, 1.5 μM SEQ ID NO.:1, 1.5 μM primer sequence (e.g., SEQ ID NOs.:4 and 5), 2.5 units Taq Polymerase (Perkin Elmer Cetus), and 1.0 μg of human eosinophil DNA. The DNA Thermal-cycler (Perkin Elmer Cetus, Model N801) is programmed for the following incubations:

1. 94° C., 2 min. (initial denaturation)
2. 94° C., 1 min. (denaturation)
3. 50° C., 1 min. (annealing)
4. 72° C., 3 min. (elongation)
5. Steps 2–4 cycle about 35–50 times (amplification)
6. 4° C., soak (storage)

The DNA amplified in this reaction is electrophoresed on 5% polyacrylamide gels to verify band length. If the size is determined to be correct, the DNA is purified by phenol extraction, then digested with Not1 and Sal1 to remove the termini. The DNA is then ligated into the Not1/Sal1 site of vector pUC19 (New England Biolabs). The DNA is transformed into E. coli strain DH5-α made competent by the CaCl$_2$ procedure (Hanahan, J. Mol. Biol. 155:557, 1983). The human LTC$_4$ synthase is then sequenced by the chain-termination method (Sanger, Proc. Natl. Acad. Sci. USA 74:5463, 1977).

An alternate cloning procedure for genomic DNA or cDNA encoding human LTC$_4$ synthase includes generating oligonucleotides from the polymerase chain reactions described above and radioactively labeling them according to the procedure described in Sambrook et al., supra. These oligonucleotides are used to screen a λgt11 genomic library from a human cell line. Alternatively, a λgt11 cDNA library prepared from mRNA from the same human cell line is used. Construction of these libraries follows the procedure of Sambrook et al., supra. Alternatively, a commercially available library, available from Clontech (Palo Alto, Calif.), is used.

Hybridization conditions are as described by Cate et al. (Cell 45:165, 1986) except that the final wash in tetramethyl ammonium chloride is omitted. DNA inserts from positive plaques are subcloned directly into the plasmid vector pBluescript SKM13+ (Stratagene, Inc. San Diego, Calif.). Positive plasmid subclones are identified by colony hybridization, with the use of the same oligonucleotide hybridization probe. Minipreparations of plasmid DNA are prepared from positive colonies.

The nucleotide sequence immediately upstream from the oligonucleotide binding site is determined by double strand sequencing (Chen et al., DNA 4:165, 1985), using $^{32}$P end-labeled oligonucleotide as sequencing primer and non-radioactive nucleotides in the extension reactions. Subclones whose codon order upstream from the priming site match the known human amino acid sequence (SEQ. ID. NO.:2) are sequenced in their entirety by the diideoxy chain termination method, with either the Klenow fragment of Escherichia coli DNA polymerase I or modified bacteriophage T7 DNA polymerase (Sequenase; United States Biochemicals) in the extension reactions. Subclones are sequenced from their termini, from both directions from a set of restriction sites. Clones are obtained whose codon order is at least partially similar to the amino acid sequence of human LTC$_4$ synthase polypeptide. A full-length genomic or cDNA sequence for human LTC$_4$ synthase polypeptide is assembled from overlapping partial clones.

Example 3

Expression of Polypeptide

In addition to the protein expression system, described in Example 1, we provide the following method for transient expression of LTC$_4$ synthase cDNA in cultured cells, which is adapted from Bimir et al. (supra). COS-7 cells, or other cultured cells are used. Tissue culture medium, serum, and antibiotics are obtained from GIBCO (Gaithersburg, Md.).

The eukaryotic expression vector pEUK-C1 is obtained from Clontech (Palo Alto, Calif.). Plasmid pEUK-UT2 is constructed by inserting SEQ ID NO.:1 cDNA (blunt-ended with T4 DNA polymerase) into the Smal side of plasmid pEUK-C1. The orientation and correct insertion at the 5' end is confirmed by DNA sequencing. pEUK-UT2 (15 μg) is transfected into COS-7 cells using lipofectin. Briefly, COS-7 cells are seeded onto 35 mm tissue culture plates (Falcon, N.J.) in Dulbecco's modified Eagle's medium (DMEM) with 10% fetal bovine serum and 1% antimycotic (containing Fungizon-GIBCO) and transfected at a confluency of 80–95%. Immediately before transfection, cell monolayers are washed twice with OPTI-MEM I medium (GIBCO). For each 35 mm plate, 15 μg of plasmid and 15 μg of Lipofectin are mixed for 30 min in 0.5 ml of OPTI-MEM I medium and then added to the plate. After incubation for 24 h at 37° C. in a humidified atmosphere containing 5% CO$_2$, 1 ml of DMEM with 10% serum is added. LTC$_4$ synthase is measured 48 to 72 h post-transfection.

In control experiments, pEUK-C1 plasmid DNA without SEQ ID NO.:1 is transfected. The transfection efficiency is monitored after co-transfection with plasmid pCH110 (Clontech), containing a functional LacZ gene and a SV40 origin of replication. COS-7 cells produce the SV40 large tumor antigen which allows replication of plasmids (such as pCH110 and pEUK-C1) containing a SV40 origin. The product of the Lac Z gene, beta-galactosidase, is measured using X-Gal. Generally, between 15–25% of cells are transfected.

Example 4

Preparation of Constructions for Transfections and Microinjections

Methods for purification of DNA for microinjection are well known to those of ordinary skill in the art (see, for example, Hogan et al., Manipulating the Mouse Embryo, Cold Spring Harbor Laboratory, NY, 1986; and Palmer et al., Nature, 300:611, 1982).

Construction of Transgenic Animals: A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci USA* 82:4438, 1985). Embryos can be infected with viruses, especially retroviruses, modified to bear human $LTC_4$ synthase genes of the invention.

Pluripotent stem cells derived from the inner cell mass of the embryo and stabilized in culture can be manipulated in culture to incorporate human $LTC_4$ synthase genes of the invention. A transgenic animal can be produced from such cells through implantation into a blastocyst that is implanted into a foster mother and allowed to come to term.

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. $B6D2F_1$ males can be used for mating and vasectomized Swiss Webster studs can be used to stimulate pseudopregnancy. Vasectomized mice and rats can be obtained from the supplier.

Microinjection Procedures: The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine et al., *Experientia,* 47:897, 1991). Other procedures for introduction of DNA into tissues of animals are described in U.S. Pat. No. 4,945,050 (Sanford et al., Jul. 30, 1990).

Transgenic Mice: Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline (DPSS) with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per is gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats: The procedure for generating transgenic rats is similar to that of mice (see Hammer et al., *Cell* 63:1099, 1990). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPSS with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

INTRODUCTION OF DNA INTO ES CELLS: Methods for the culturing of ES cells and the subsequent production of transgenic animals by the introduction of DNA into ES cells using methods such as electroporation, calcium phospliate/DNA precipitation; and direct injection are well known to those of ordinary skill in the art (see, for example, *Teratocarcinomas and Embryonic Stem Cells, A Practical Approach*, Robertson, ed., IRL Press, 1987). Selection of the desired clone of thrombospondin-4-containing ES cells is accomplished through one of several means. Although embryonic stem cells are currently available for mice only, it is expected that similar methods and procedures as described and cited here will be effective for embryonic stem cells from different species as they become available.

In cases involving random gene integration, a clone containing the human $LTC_4$ synthase gene of the invention is co-transfected with a gene encoding neomycin resistance. Alternatively, the gene encoding neomycin resistance is physically linked to the human $LTC_4$ synthase gene. Transfection is carried out by any one of several methods well known to those of ordinary skill in the art (E.J. Robertson, supra). Calcium phosphate/DNA precipitation, direct injection, and electroporation are the preferred methods. Following DNA introduction, cells are fed with selection medium containing 10% fetal bovine serum in DMEM supplemented with G418 (between 200 and 500 μg/ml biological weight). Colonies of cells resistant to G418 are isolated using cloning rings and expanded. DNA is extracted from drug resistant clones and Southern blotting experiments using a transgene-specific DNA probe are used to identify those clones carrying the human $LTC_4$ synthase polypeptide sequences. In some experiments, PCR methods are used to identify the clones of interest.

DNA molecules introduced into ES cells can also be integrated into the chromosome through the process of homologous recombination (Copecchi, *Science,* 244:1288, 1989). Direct injection results in a high efficiency of integration. Desired clones are identified through PCR of DNA prepared from pools of injected ES cells. Positive cells within the pools are identified by PCR subsequent to cell cloning. DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Copecchi (supra) and Joyner et al. (*Nature*, 338:153, 1989), the disclosures of which are incorporated herein by reference.

EMBRYO RECOVERY AND ES CELL INJECTION: Naturally cycling or superovulated female mice mated with males are used to harvest embryos for the implantation of ES cells. It is desirable to use the C57BL165 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 μm.

TRANSFER OF EMBRYOS TO RECEPTIVE FEMALES: Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

IDENTIFICATION OF TRANSGENIC MICE AND RATS: Tail samples (1–2 cm) are removed from three week old animals. DNA is prepared and analyzed by Southern blot or PCR to detect transgenic founder ($F_0$) animals and their progeny ($F_1$ and $F_2$). In this way, animals that have become transgenic for the desired human $LTC_4$ synthase genes are identified. Because not every transgenic animal expresses the polypeptide, and not all of those that do will have the expression pattern anticipated by the experimenter, it is necessary to characterize each line of transgenic animals with regard to expression of the $LTC_4$ synthase in different tissues.

Production of Non-Rodent Transgenic Animals: Procedures for the production of non-rodent mammals and other animals have been discussed by others (see Houdebine et al., supra; Pursel et al., *Science* 244:1281, 1989; and Simms et al., *Bio/Technology* 6:179, 1988).

Identification of Other Transgenic Organisms: An organism is identified as a potential transgenic by taking a sample of the organism for DNA extraction and hybridization analysis with a probe complementary to the human $LTC_4$ synthase gene of interest. Alternatively, DNA extracted from the organism can be subjected to PCR analysis using PCR primers complementary to the human $LTC_4$ synthase gene of interest.

Example 5

Protocol for Inactivating the Human $LTC_4$ Synthase Gene

Mouse genomic clones are isolated by screening a genomic library from the D3 strain of mouse with a human $LTC_4$ synthase probe. Duplicate lifts are hybridized with a radiolabeled probe by established protocols (Sambrook, et al., supra). Plaques that correspond to positive signal on both lifts are isolated and purified by successive screening rounds at decreasing plaque density. The validity of the isolated clones is confirmed by nucleotide sequencing.

The genomic clones are used to prepare a gene targeting vector for the deletion of human $LTC_4$ synthase polypeptide in embryonic stem cells by homologous recombination. A neomycin resistance gene (neo) with its transcriptional and translational signals, is cloned into convenient sites that are near the 5' end of the gene. This will disrupt the coding sequence of human $LTC_4$ synthase polypeptide and allow for selection by the drug Geneticin (G418) by embryonic stem (ES) cells transfected with the vector. The Herpes simplex virus thymidine kinase (HSV-tk) gene is placed at the other end of the genomic DNA as a second selectable marker. Only stem cells with the neo gene will grow in the presence of this drug.

Random integration of this construct into the ES genome will occur via sequences at the ends of the construct. In these cell lines, the HSV-tk gene will be functional and the drug gancyclovir will therefore be cytotoxic to cells having an integrated sequence of the mutated human $LTC_4$ synthase coding sequence.

Homologous recombination will also take place between homologous DNA sequences of the ES human $LTC_4$ synthase genome and the targeting vector. This usually results in the excision of the HSV-tk gene because it is not homologous with the human $LTC_4$ synthase gene.

Thus, by growing the transfected ES cells in G418 and gancyclovir, the cell lines in which homologous recombination has occurred will be highly enriched. These cells will contain a disrupted coding sequence of human $LTC_4$ synthase. Individual clones are isolated and grown up to produce enough cells for frozen stocks and for preparation of DNA. Clones in which the human $LTC_4$ synthase gene has been successfully targeted are identified by Southern blot analysis. The final phase of the procedure is to inject targeted ES cells into blastocysts and to transfer the blastocysts into pseudopregnant females. The resulting chimeric animals are bred and the offspring are analyzed by Southern blotting to identify individuals that carry the mutated form of the gene in the germ line. These animals will be mated to determine the effect of human $LTC_4$ synthase polypeptide deficiency on murine development and physiology.

Example 6

Molecular Cloning and Analysis of Human $LTC_4$ Synthase Genomic Clone

Materials and Methods

CELL CULTURE: KG-1 cells, (American Type Culture Collection, Rockville, Md.) were cultured in RPMI-1640 medium (JRH Biosciences, Lenexa, Kans.), supplemented with 10% fetal calf serum (FCS) (Sigma, St. Louis, Mo.), 100 units/ml penicillin, and 100 μg/ml streptomycin (Sigma) at 37° C. under 5% $CO_2$. In vitro derived eosinophilic granulocytes were cultured from fetal cord blood mononuclear cells in RPMI-1640 with 10% FCS, 50 μM β-mercaptoethanol, 200 pM recombinant human (rh) interleukin-5 (IL-5) and 350 pM rhIL-3 (R & D Systems, Minneapolis, Minn.) on Matrigel™ (Fisher Scientific, Pittsburgh, Pa.) for 14 days (Boyce et al. *J. Exp. Med.* 182:49, 1995).

GENOMIC CLONING OF HUMAN $LTC_4$ SYNTHASE: A P1 genomic library was screened by Human Genome Systems (St. Louis, Mo.) with a polymerase chain reaction (PCR) product generated from oligonucleotides designed from the cDNA for human $LTC_4$ synthase. The sense oligonucleotide, 5'-CGTGGGCCTGAGACCAAG-3', and the antisense oligonucleotide, 5'-CGGTCACTAGAACT TTAATGATAGAG-3', corresponded to nucleotides 496–518 and 622–597, respectively, of the cDNA (SEQ ID NO.:1). A positive genomic P1 clone for $LTC_4$ synthase was identified and its plasmid DNA was digested with various restriction enzymes (BamHI, TaqI, SalI, HindIII, EcoRI, HaeIII, XbaI, XhoI, ApaI, SacI, EagI) (New England Biolabs, Beverly, Mass.). The reaction products were separated by electrophoresis in a 1% agarose gel, transferred to a nylon membrane (Millipore, Bedford, Mass.), and probed with a fluorescent labeled full-length cDNA for $LTC_4$ synthase using a chemiluminescent development method (Stratagene, La Jolla, Calif.). The blot was stripped and sequentially probed with $\gamma^{32}P$(3000 Ci/mmol, 10 mCi/ml, DuPont, Boston, Mass.) end-labeled oligonucleotides from the 5'(5'-AGCTCGCCTTCACACACAGCCCG-3', corresponding to nucleotides 11–33 of SEQ ID NO.:1) and 3'(5'-CGGTCACTAGAACTTTAATGATAGAG-3', corresponding to nucleotides 622–597 of SEQ ID NO.:1) untranslated regions of the $LTC_4$ synthase cDNA. DNA was subcloned into the pT7T3 Vector (Pharmacia, Uppsala, Sweden) and was sequenced by the method of Sanger et al. (Sanger et al., *Proc. Natl. Acad. Sci. USA* 74:5463, 1977), using dye-labeled dideoxy nucleotides as terminators (Smith et al., *Nature* 321:674, 1986), and an applied Biosystems 373A automated DNA sequencer in the Dana-Farber Cancer Institute Molecular Biology Core Facility.

SOUTHERN BLOT ANALYSIS OF TOTAL GENOMIC DNA: One 30 μg sample of DNA isolated form human peripheral blood leukocytes was digested with the restriction enzyme SacI, and another sample was digested with KpnI. Two 200-ng samples of P1 genomic DNA were treated in the same manner. The DNA preparations from both digests were resolved in a 0.75% agarose gel and transferred by capillary electrophoresis to a nylon membrane. The membrane was hybridized (Sanbrook et al., supra) with a $^{32}P$-labeled full-length cDNA for $LTC_4$ synthase and developed with Kodak XAR film (Rochester, N.Y.) with two intensifying screens for 5 days.

PRIMER EXTENSION ANALYSIS: Poly $A^+$ RNA was isolated directly from $1\times10^8$ KG-1 cells with oligo(dT) cellulose resin (Invitrogen, San Diego, Calif.) as described by the manufacturers. Poly $A^+$ RNA was also obtained from $5\times10^8$ in vitro-derived eosinophilic granulocytes cultured for 14 days with the use of TRI-reagent (Molecular Research, Inc., Cincinnati, Ohio) to extract 300 μg of total RNA and subsequent selection with oligo(dT) cellulose resin. A synthetic antisense oligonucleotide 5'-AGTAGAGGTACCTCGTCCTTCATG-3' (nucleotides 78–54 of the $LTC_4$ synthase cDNA (SEQ ID NO.:1)) was labeled with $\gamma^{32}P$ using T4 polynucleotide kinase (Promega, Madison, Wis.). A 10-pmol sample of the labeled primer was annealed to 8 μg of poly $A^+$ RNA from KG-1 cells or from in vitro derived eosinophilic granulocytes, with a primer extension kit (Promega, Madison, Wis.) in 16-μl reaction volumes and incubated at 70° C. for 10 min and then at 41° C. for 5 min. Reverse transcription with the addition of 1 unit of avian myeloblastosis virus reverse transcriptase was carried out at 41° C. for 30 min. The reaction products were precipitated by the addition of 2 μg glycogen, 7.5 μl 4M $NH_4OAc$, and 100 μl of 100% ethanol. The reaction products were resuspended in 4 μl of sample buffer, boiled for 10 min and resolved in a 6% acrylamide, 6.7 M urea gel at 60 watts for ~1 h. Additionally, for identification of the specific nucleotides at the transcription initiation sites, a genomic sequencing ladder was generated with the same primer as in the extension reaction to sequence the $LTC_4$ synthase genomic clone according to the dideoxy chain termination method of Sanger et al. (*Proc. Natl. Acad Sci. USA* 74:8463, 1977). These reaction products and $^{32}P$-labeled molecular weight standards were run in parallel lanes of the same gel. The gel was dried and exposed to Kodak XAR film with two intensifying screens for 5 days.

CHROMOSOMAL LOCALIZATION: A genomic DNA blot from 25 human-rodent somatic hybrid DNAs that had been digested with TaqI (Biosys, New Haven, Conn.) was probed with a $^{32}P$-labeled full-length cDNA for $LTC_4$ synthase and then exposed to Kodak XAR film for 2 weeks. A fluorescent in situ hybridization technique for the chromosomal localization of the $LTC_4$ synthase gene was performed by Human Genome Systems. Briefly, purified DNA of the $P_1$ clone from which the entire genomic sequence was obtained was labeled with digoxigenin dUTP by nick translation. Labeled probe was hybridized to normal metaphase chromosomes derived from phytohemagglutinin-stimulated peripheral blood lymphocytes, and specific hybridization signals were detected by incubating the hybridized slides with fluoresceinated antidigoxigenin antibodies followed by counter-staining with propidium iodide.

Results

CHARACTERIZATION OF GENOMIC CLONE FOR HUMAN $LTC_4$ SYNTHASE: a 5.5 kbp SadI digested fragment liberated from the P1 plasmid hybridized with the full-length cDNA for $LTC_4$ synthase and with the full-length cDNA for $LTC_4$ synthase and with oligonucleotide primers from the 5' end and the 3' end of the cDNA, indicating that the full-length gene was contained within this fragment. This DNA fragment was subcloned and sequenced. The entire nucleotide sequence (FIG. 3) of the 5 exons and 4 introns, which spanned 2.52 kbp, was sequenced in both directions. 1.35 kbp of the 5' flanking region and 0.56 kbp of the 3' flanking region sequence were also obtained in both directions (FIG. 3). The intronlexon junctions were determined by nucleotide sequence comparison with the cDNA, and obey the GT-AG rule (Breathinach et al. *Ann Rev. Bioch.* 50:349 1981). The exon sequence exhibits 100% identity to that of the cDNA (SEQ ID NO.:1). The size of the exons ranged from 71–257 bp and the introns from 84–1445 bp (Table 1).

TABLE I

Comparison of the intron and exon sizes of $LTC_4$ synthase and FLAP

|  | LTC4 Synthase (bp) | FLAP (bp) |
|---|---|---|
| Exon I | 154 | 144 |
| Exon II | 100 | 100 |
| Exon III | 71 | 71 |
| Exon IV | 82 | 82 |
| Exon V | 257 | 478 |
| Intron I | 1445 | $9.0\times10^3$ |
| Intron II | 102 | $8.4\times10^3$ |
| Intron III | 84 | $4.2\times10^3$ |
| Intron IV | 230 | $8.6\times10^3$ |

Figure 5:
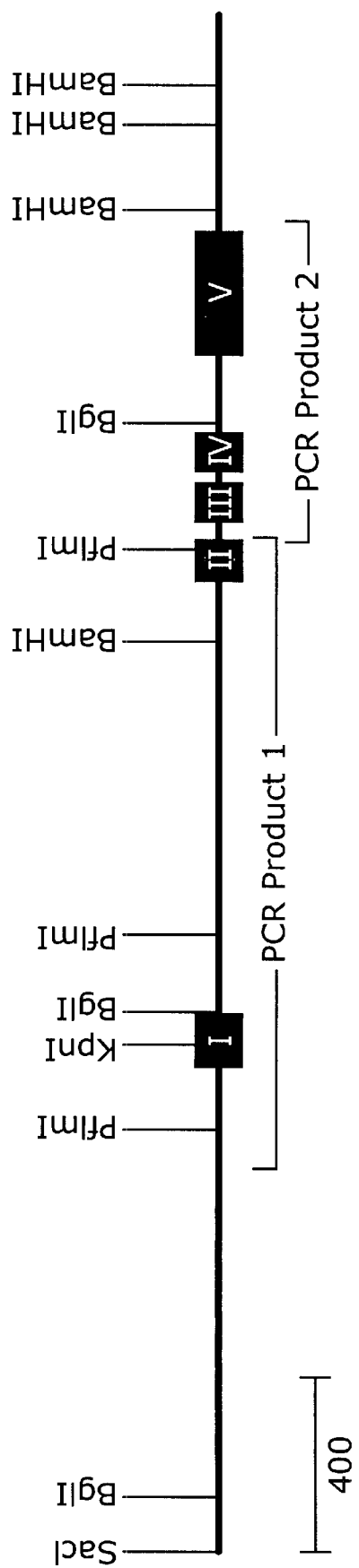
FIG. 5 presents a map of the gene for LTC$_4$ synthase obtained by overlapping PCR products. PCR product 1 extends from oligonucleotide number −530 to +1609, with nucleotide 1 corresponding to the ATG start site, and encompasses some of the 5' flanking region, the first exon, and most of the second exon. PCR product 2 corresponding to nucleotides 1573–2429, overlaps PCR product 1 in the second exon, and extends through exon 5.

To confirm the presence of the full-length gene, two overlapping PCRs were performed, using human genomic DNA as a template (FIG. 5). The expected PCR products of 2.1 and 0.86 kbp respectively, were obtained and spanned the complete length of the $LTC_4$ synthase gene (FIG. 5).

Figure 6:
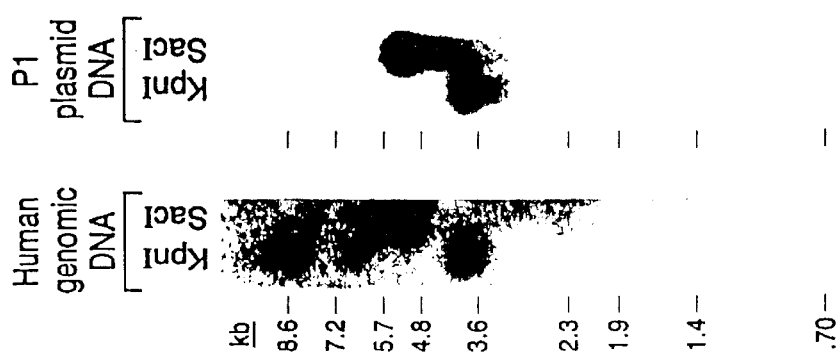
FIG. 6 represents an analysis of genomic DNA isolated from the P1 plasmid and from peripheral blood leukocytes of a normal donor. Two-hundred nanograms of P1 plasmid DNA from a clone known to contain the gene for LTC$_4$ synthase and 30 µg of genomic DNA from peripheral blood leukocytes were individually digested with the SacI and KpnI restriction enzymes, resolved in a 1% agarose gel, transferred to a nitrocellulose membrane, and probed with a $^{32}$P-labeled full-length cDNA for LTC$_4$ synthase.

A DNA blot was prepared from human genomic DNA and from P1 plasmid DNA, each of which was digested with KpnI and SacI, and probed with the full length cDNA for $LTC_4$ synthase (FIG. 6). The patterns of hybridization in the P1 and the human genomic DNA were identical.

Figure 7:
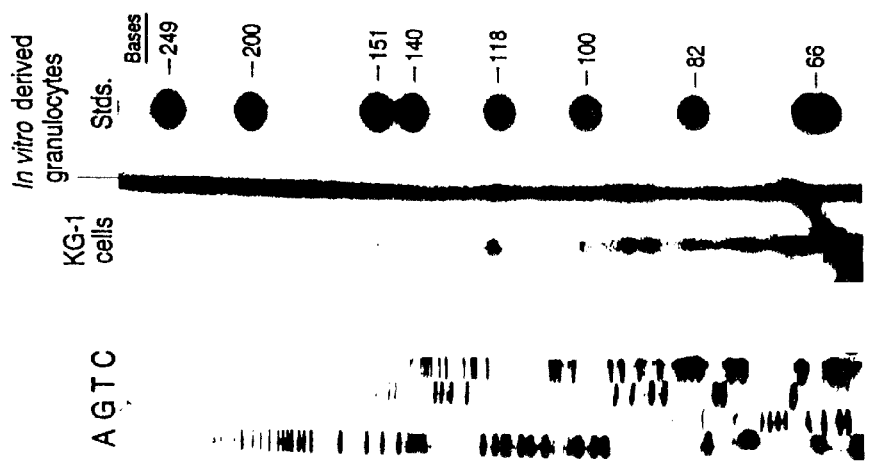
FIG. 7 is the transcription initiation site analysis for the human LTC$_4$ synthase gene. Samples of poly A$^+$ RNA isolated from KG-1 monocytic cells and from in vitro-derived granulocytes were extended by reverse transcription with a primer corresponding to nucleotides 78 to 54 of the LTC$_4$ synthase cDNA. A genomic sequencing ladder was performed in parallel and is shown on the left with the appropriate radiolabeled nucleotides. Molecular weight markers are shown on the right.

ANALYSIS OF TRANSCRIPTION START SITES: The transcription initiation sites were determined by primer extension of poly $A^+$ RNA derived from KG-1 cells and from in vitro-derived hybrid granulocytes, with comparison to parallel lanes containing the sequence of the $LTC_4$ synthase genomic clone and molecular weight markers, respectively (FIG. 7). Both cellular sources revealed three predominant transcription initiation start sites 66, 69, and 96 nucleotides upstream from the ATG translation start site.

CHROMOSOMAL LOCALIZATION OF THE GENE FOR HUMAN $LTC_4$ SYNTHASE: The cDNA for $LTC_4$ synthase hybridized to the genomic DNA from 8 of the 26 human-rodent somatic cell hybrids. The only chromosome common to these hybrids was chromosome 5.

Fluorescent in-situ hybridization with the P1 plasmid clone containing the gene for $LTC_4$ synthase was performed to confirm the chromosomal assignment and to localize the region on the chromosome. The fluorescent in-situ hybridization specifically labeled the long arm of a group B chromosome (chromosome 4 or 5). In a subsequent experiment, a probe associated with the cri-du-chat locus, previously mapped to 5q21 by Genome Systems, and the P1 clone for $LTC_4$ synthase were simultaneously hybridized to chromosome 5. In that experiment, 73 of a total of 80 cells in metaphase that were analyzed, exhibited specific labeling for the human $LTC_4$ synthase gene. Measurements of 10 specifically hybridized chromosomes demonstrated that the P1 cloned localized at a position 98% of the distance from the centromere to the telomere of chromosome arm 5q, an area that corresponds to band 5q35.

Example 7

Protocol for Detection of Polymorphisms in the Human $LTC_1$ Synthase Gene

Polymerase chain reaction-single stranded conformational polymorphism (Hayashi et al., *PCR Met. App.* 1:34, 1992) is a procedure based on the principle that single-stranded DNA molecules take on specific sequence-based secondary structures (conformers) under nondenaturing conditions and therefore molecules which differ by as little as a single based substitution migrate differently (Onta et al. *Proc. Natl. Acad. Sci. USA* 86:2766, 1989). The protocol for this procedure begins by designing and synthesizing a set of $LTC_4$-synthase specific primer pairs which span 150–250 base pairs within a defined area of interest within the gene. The sensitivity of the procedure is dependent on the size of the PCR product, with 97% of mutations detected in fragments of 155 bp, 76% in 175 bp fragments, and 70% in 212 bp fragments (Stelfield et al., *Genomics* 16:325, 1993). The promotor and enhancer elements within the 5' untranslated flanking region are preferably examined initially, followed by the exons and finally the introns. One of the primers is end-labelled with $^{32}P$ using $T_4$ kinase. Templates for PCR are provided for, for example, 55 separate PCR reactions using 250 ng of genomic DNA obtained from SV-40 immortalized peripheral blood leukocytes of 25 normal individuals, 25 asthma subjects, and 5 asthma subjects with aspirin induced symptoms as templates of the PCR. An aliquot of these PCR products is then analyzed by non-denaturing 6% acrylamide gels (AT Biochem) run for 40 watts in 1×TBE for 4–5 hours at 4° C., dried and visualized by autoradiography for band shifting which indicates the presence of a polymorphism.

Example 8

Identification of Transcriptional Regulatory Sites that Modulate $LTC_1$ Synthase Gene Expression To analyze the $LTC_4$ synthase promoter and identify regulatory sequences therein that modulate $LTC_4$ synthase gene expression, portions of the $LTC_4$ genomic clone (SEQ ID NO.:10) corresponding to sequences upstream (5') of the transcription start site (see FIG. 3; SEQ ID NO.:10 nucleotide 1351) are amplified by PCR and are ligated to the pCAT-enhancer vector (Promega), which contains the SV40 enhancer element downstream of the CAT gene to produce a fusion construct. This fusion construct is transfected into leukemic cells that express the $LTC_4$ synthase gene, such as HL-60, THP-1, and/or U937 cells. Preferably, the construct is introduced into the cells by electroporation. CAT expression within the cells is monitored using a CAT ELISA immunoassay kit (Boelringer Mamnheim, Catalog number 1363727).

Enhancer elements within the $LTC_4$ synthase promoter are identified by fusing variously sized 5' flanking region fragments to the pCAT-promoter vector (Promega), which contains the SV40 enhancer element upstream of the CAT gene. The $LTC_4$ synthase promoter. fragments are amplified by PCR and are introduced into the pCAT-promoter vector so that they are downstream of the CAT gene. As above, the fusion construct is introduced into cells that express the $LTC_4$ synthase gene, and CAT expression is monitored by CAT ELISA.

$LTC_4$ synthase regulatory sequences and enhancers are identified by comparing CAT expression in cells transfected with constructs including truncated (or mutated) fragments with i) expression in cells transfected with constructs including the entire $LTC_4$ synthase upstream region; and with ii) expression in cells transfected with constructs that lack any $LTC_4$ synthase promoter sequences; and/or with cells transfected with the basic promoterless, enhancerless pCAT vector (Promega).

Example 9

Mutational Analysis of the Human $LTC_4$ Synthase Protein

Materials and Methods

REAGENTS: COS-7 cells (American Type Culture Collection, Rockville, Md.); Nu serum plus (Collaborative Research, New Bedford, Mass.); Taq polymerase and dNTP (Pharmacia Biotech, Uppsala, Sweden); MK-886 and FLAP cDNA (Dr. J. Evans, Merck Frosst, Pointe Claire-Dorval, Quebec, Canada); dimethylsulfoxide (DMSO), chloroquine, DEAE-dextran (MW>500,000), bovine serum albumin, GSH, bis-tris propane, fetal calf serum (Sigma Chemicals, St. Louis, Mo.) and acetonitrile and methanol (Burdick & Jackson, Muskegon, Mich.) were obtained from the suppliers. $LTA_4$-methyl ester ($LTA_4$-ME) (Dr. J. Rokach, Florida Institute of Technology, Melbourne, Fla.) was synthesized as described (Lam et al., *Tetrahedron Lett.*, 22:2759, 1996).

COS-7 cells were cultured in RPMI-1640 medium supplemented with 10% heat-inactivated fetal calf serum and 15 μg/ml gentamycin at 37° C. under a humidified atmosphere of 5% $CO_2$ and 95% air.

SITE-DIRECTED MUTAGENESIS: Polymerase chain reaction (PCR) mutagenesis was carried out to generate the appropriate mutated cDNAs. Primer I corresponded to nucleotides 5'-1 to 18-3' of $LTC_4$ Synthase cDNA. Primer II, a 3' primer, corresponded to nucleotides 3-597 to 622-5'. Two primary PCR fragments were produced by using primer I plus the inverse mutagenic primer (3' primer) and primer II plus the forward mutagenic primer (5' primer) for 30 cycles. The two primary PCR fragments were mixed, then denatured at 97° C. for 2 min, annealed at 55° C. for 2 min, and extended at 72° C. for 4 min for one cycle. The secondary PCR products with the specific mutations were obtained after 30 additional cycles of PCR with primers I and II.

To obtain hybrid A, a chimeric molecule of $LTC_4$ synthase and FLAP, 30-base mutagenic oligo nucleotides were used in which the first 15 nucleotides corresponded to the $LTC_4$ synthase sequence and the second 15 nucleotides to the FLAP sequence. The first primary PCR fragment was generated with Primer I and the reverse mutagenic oligonucleotide with $LTC_4$ synthase cDNA as template, and the second primary PCR fragment was obtained with the forward mutagenic oligonucleotide and Primer III (a 3' oligonucleotide corresponding to nucleotides 739–710 of FLAP cDNA). To obtain hybrid B and hybrid C, 6 and 12 PCR reactions with appropriate oligonucleotides, respectively, were carried out to generate the primary products.

The mutated cDNAs were ligated into the pCR3 expression vector (Invitrogen, San Diego, Calif.). The constructed plasmids bearing the desired mutations were used to transform the *E. coli* strain Top 10F' by the calcium chloride procedure (Sambrook et al., *Molecular Cloning. A Laboratory Manual*, 2nd Ed, Cold Spring Harbor Laboratory, Cold Spring Harbor, N.Y., 1989) and were sequenced to confirm the desired base substitutions and to ensure that no other mutations were introduced into the nucleotide sequence during PCR.

Plasmids were prepared with a Nucleobond isolation kit (Nest, Southboro, Mass.) or a QIAprep spin column (Qiagen, Chatsworth, Calif.) and were sequenced as described as Sanger et al. (Smith et al., *Nature*, 321:674, 1986) using dye-labeled dideoxy nucleotides as terminators. The samples were analyzed on an Applied Biosystems model 373A automated DNA sequencer (Smith et al., *Nature*, 321:674, 1986).

TRANSFECTION AND FUNCTIONAL ANALYSIS OF THE EXPRESSED PROTEINS: COS-7 cells were transfected with either wild-type $LTC_4$ synthase cDNA or the mutated $LTC_4$ synthase cDNA by DEAE-dextran transfection (Lam et al., *Proc. Natl. Acad. Sci. USA.*, 91:7663, 1994). Three days after transfection, the cells were harvested by treatment with trypsin and suspended in microsomal buffer (50 mM HEPES buffer pH 7.9 containing 2 mM EDTA and 10 mM β-mercaptoethanol) at a concentration of $5 \times 10^6$ cells/ml. The cells were lysed by sonication with a Branson microtip sonicator (Danbury, Conn.) at a setting of 7. Cell lysates were centrifuged at 100,000×g for 60 min at 4° C., and the pellets (microsomes) were resuspended in microsomal buffer and were solubilized by the addition of 0.4% Triton X-102, 0.4% sodium deoxycholate (DOC), and 10% glycerol and stirring at 4° C. for 45 min.

The function of each mutant enzyme as well as the wild-type enzyme was first screened by the incubation of 1–10 µl of solubilized COS cell microsomes with 10 mM GSH and 20 µM $LTA_4$-ME in 200 µl 50 mM HEPES buffer containing 10 mM $MgCl_2$, pH 7.6. The reactions were carried out at room temperature for 10 min and stopped by the addition of 3 vol methanol containing 200 ng prostaglandin $B_2$ ($PGB_2$) as an internal standard. $LTC_4$-ME levels in the samples were determined with high performance liquid chromatography (HPLC). When a mutated construct did not provide enzyme function, the expression of the mutated protein was confirmed by SDS-PAGE immunoblot analysis with rabbit anti-$LTC_4$synthase antibody as described (Penrose et al., *Am. J. Respir. Crit. Care Med.*, 152:283, 1995).

Reverse phase (RP)-HPLC was carried out with a model 126 dual pump system and model 167 scanning UV detector (Beckman Instruments) controlled by an Gateway 2000 P4D66 computer equipped with Beckman System Gold software. Samples were applied to a 5-µm 4.6×250-mm C18 Ultrasphere reverse phase column (Beckman Instruments) equilibrated with a solvent of methanol/acetonitrile/water/acetic acid (10:15:100:0.2, v/v), pH 6.0 (solvent A). Immediately after the sample was injected, the column was eluted at a flow rate of 1 ml/min with a programmed concave gradient (System Cold curve 6) to 20% solvent A and 80% solvent B (pure methanol) over 0.2 min with continuation isocratically for 5.8 min. Beginning at 6 min, solvent B was increased linearly to 100% over 0.2 min and was maintained at this level for 7 min more. The ultraviolet absorbance at 280 nm and the ultraviolet spectra were recorded simultaneously. The retention times for $PGB_2$ and $LTC_4$-ME were 7.4 and 8.9 min, respectively. $LTC_4$-ME was quantitated by calculating the ratio of the peak area to the area of the internal standard $PGB_2$.

The study the effect of pH on enzymatic conjugation by wild-type and mutant enzyme, 1-µl or 5-µl (Y93F) samples of solubilized COS cell microsomes were incubated with 10 µM $LTA_4$-ME and 10 mM GSH in bis-Tris propane buffer containing 10 mM $MgCl_2$ at various pH levels. The reactions were carried out at room temperature for 2 min and were stopped by the addition of 3 vol of methanol and 10 µl of acetic acid. Product generation was quantitated by RP-HPLC as described above.

PURIFICATION AND KINETIC ANALYSIS OF SELECTED EXPRESSED PROTEINS: Recombinant $LTC_4$ synthases were purified by S-hexyl GSH agarose affinity chromatography (Lam et al., *Eur. J. Biochem.*, 238:606, 1996). Solubilized microsomes were loaded onto a 2.5-cm× 1.5-cm open bed of S-hexyl GSH resin equilibrated with 50 mM HEPES, 1 mM EDTA, 5 mM β-mercaptoethanol, 0.1% Triton X-102, 10% glycerol, pH 7.6 (Buffer A) at 4° C. The column was washed sequentially with 5 volumes each of buffer A/0.3 M NaCl/20 mM GSH/0.1% DOC, buffer A/2.5 mM S-hexyl GSH/2.5 mM S-octyl GSH/0.1% DOC, and buffer A/0.1% DOC; and the enzyme was eluted with 5 fractions of 1 volume each of 15 mM probenecid in buffer A containing 0.1% DOC. The enzyme was purified nearly to homogeneity as determined by the presence in silver stained SDS-PAGE gels of a predominant 18-kDa protein band with a minor 34-kDa band; only the 18-kDa band interacted with anti-$LTC_4$ synthase antibody on immunoblot analysis. After sequential concentration and dilution with a Microsep 10K centrifugal concentrator (Filtron Technology Corp., Northborough, Mass.) to remove probenecid, the protein concentration was estimated by staining a SDS-PAGE gel of the purified enzyme and a standard amount of lysozyme resolved in the same gel with Coomassie blue dye and comparing their intensities.

To examine the enzyme kinetics of recombinant wild-type or mutant $LTC_4$ synthase, 3–100 ng portions of purified enzyme were incubated in 200 µl of HEPES buffer, pH 7.6, containing 10 mM $MgC'_2$ with either 20 µM $LTA_4$-ME and various concentration of GSH or with 10 mM GSH and various concentrations of $LTA_4$-ME for 2 min at room temperature. The reactions were terminated by the addition of 3 vol of methanol containing 200 ng $PGB_2$. Samples were then analyzed for $LTC_4$-ME by RP-HPLC.

Results

POINT MUTATIONS OF CYSTEINES AND ASPARAGINE: To determine the possible involvement of the two cysteine residues in the dimer formation required for function, we mutated C56 to S56 and C82 to V82 in separate constructs and within the same construct. None of the mutations affected conjugation function of the transfected COS cell microsomes, indicating that neither cysteine residue is involved in dimer formation or in enzyme catalysis. The mutation of the single consensus N-glycosylation site at N55 to A did not alter the electrophorectic mobility in SDS-PAGE, suggesting that this residue is not glycosylated in $LTC_4$ synthase. The mutation N55A did, however, increase the Km of GSH for the enzyme, suggesting that this residue participates in the GSH binding site.

POINT MUTATIONS OF CHARGED RESIDUES: We directed our initial point mutation studies to charged amino acid residues. FIG. 8 depicts the mutations that we made, and compares them with the FLAP protein sequence. A dashed line indicates amino acid identity. The three hydrophobic domains are boxed and the putative FLAP inhibitor binding domain in underlined. Amino acid residues subject to point mutations are printed in bold italics. Residues R51 and Y93, which effect the catalytic function of $LTC_4$ synthase, are in the largest print. Amino acid residue numbers are on the right.

The mutation of E45Q, E47Q, E58Q, and R48S did not attenuate the conjugation function of the transfected COS cell microsomes as compared to wild-type construct in the same assay. However, the mutation of Arg 51 to isoleucine or threonine abolished the functional activity of the enzyme. Of importance, activity was not diminished in the microsomes by point mutation of Arg 51 to lysine or histidine, both of which have the ability to function as basic side chains to donate a $H^+$ ion. The active and inactive R51 mutants were comparably positive for protein by immunoblot analysis of the microsomes.

To confirm the immunoblot analysis of the microsomal preparation, and to assess one parameter of protein folding, we examined the ability of the R51T mutant protein to bind a S-hexyl GSH agarose column. R51T bound to S-hexyl GSH and could be eluted from the column with probenecid in the same protocol as the wild-type enzyme. Nonetheless, purified R51T was not able to catalyze the conjugation reaction even at a protein concentration 30-fold higher than that of the wild-type enzyme (data not shown).

POINT MUTATIONS OF THE TYROSINE RESIDUES: Because a tyrosine residue is known to catalyze the conjugation of the GSH with xenobiotics in cytosolic GST S-transferases (Wang et al., *J. Biol. Chem.*, 267:19866, 1992; and Johnson et al., *J. Biol. Chem.*, 268:11508, 1993), the role of such residues was examined by point mutations of $LTC_4$ synthase. Mutations of Y59F, Y93F, and Y97F each increased the $K_m$ of GSH by 5–15 fold in the microsomal assay (Table 2). Only the mutation of Y93F was associated with a reduction in function under standard assay conditions. None of the tyrosine mutants with an elevated $K_m$ for GSH exhibited a change in the $K_m$ for $LTA_4$-ME, thereby revealing substrate specificity.

TABLE 2

Kinetic parameters of wild-type and mutant $LTC_4$ Synthase

| | COS CELL MICROSOME | | | PURIFIED RECOMBINANT ENZYME | | |
|---|---|---|---|---|---|---|
| | $K_m$ | | | $K_m$ | | Vmax |
| Enzyme Type | $LTA_4$-ME (µM) | GSH (mM) | Function (% of WT) | $LTA_4$-ME (µM) | GSH (mM) | $LTC_4$-ME (µmol/min/mg) |
| WT | 6–20 | 0.5–2.0 | 100 | 7.4 | 1.4 | 51.3 |
| R51T | N.D. | N.D. | 0 | N.D. | N.D. | Inactive |
| R51H | 6.4 | 3.8 | 100 | 6.3 | 1.5 | 20.0 |
| Y93F | 20.0 | 10.0 | 5 | 5.4 | 9.9 | 1.4 |
| C82V | 10.9 | 2.0 | 100 | 6.3 | 0.9 | 37.7 |
| A52S | 4.5 | 30.0 | 80 | N.D. | N.D. | N.D. |
| Y59F | 19.0 | 15.5 | 100 | N.D. | N.D. | N.D. |
| Y109I | 20.0 | 1.6 | 100 | N.D. | N.D. | N.D. |
| Y97F | 16.5 | 16.5 | 100 | N.D. | N.D. | N.D. |
| N55A | 7.7 | 10.7 | 85 | N.D. | N.D. | N.D. |
| V49F | 10.0 | 9.2 | 100 | N.D. | N.D. | N.D. |
| R51K | 9.4 | 2.3 | 100 | N.D. | N.D. | N.D. |
| V69T | 19.0 | 2.0 | 100 | N.D. | N.D. | N.D. |
| L62T | 6.7 | 2.5 | 100 | N.D. | N.D. | N.D. |
| R51I/WT | 6.5 | 3.2 | 90 | N.D. | N.D. | N.D. |
| Hybrid A | 5.6 | N.D. | 60 | N.D. | N.D. | N.D. |
| Hybrid C | 9.5 | N.D. | 20 | N.D. | N.D. | N.D. |

Figure 10:
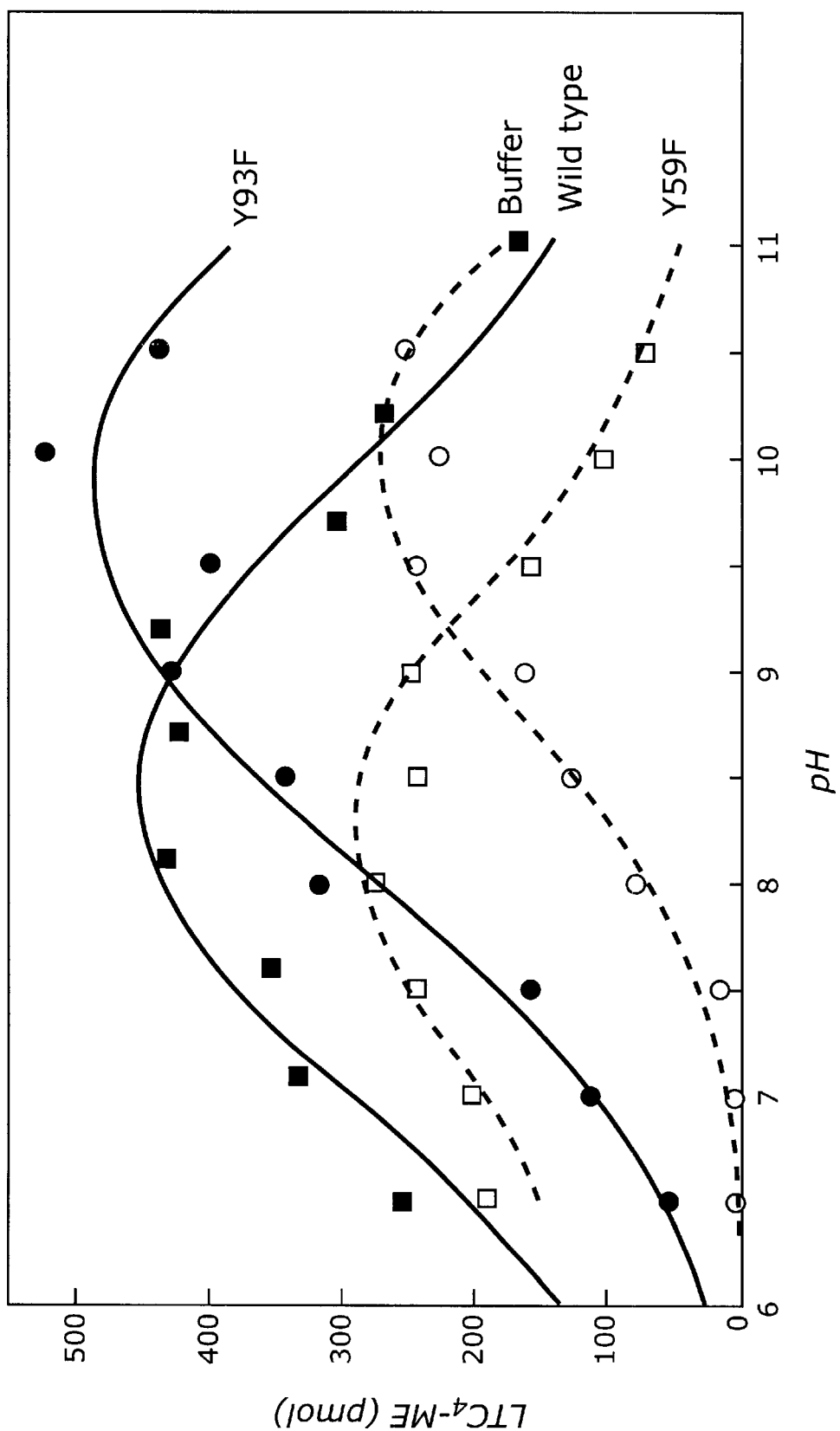
FIG. 10 shows the effect of pH on the conjugation of LTA$_4$-ME with GSH. Reactions were carried out in the presence of the solubilized microsome from COS cells transfected with wild-type (1 µl, solid square), Y59F (1 µl, open square) or Y93F (5 µl, solid circle) LTC$_4$ synthase, and in the absence of added enzyme (open circle). A representative experiment is shown.
Figure 13:
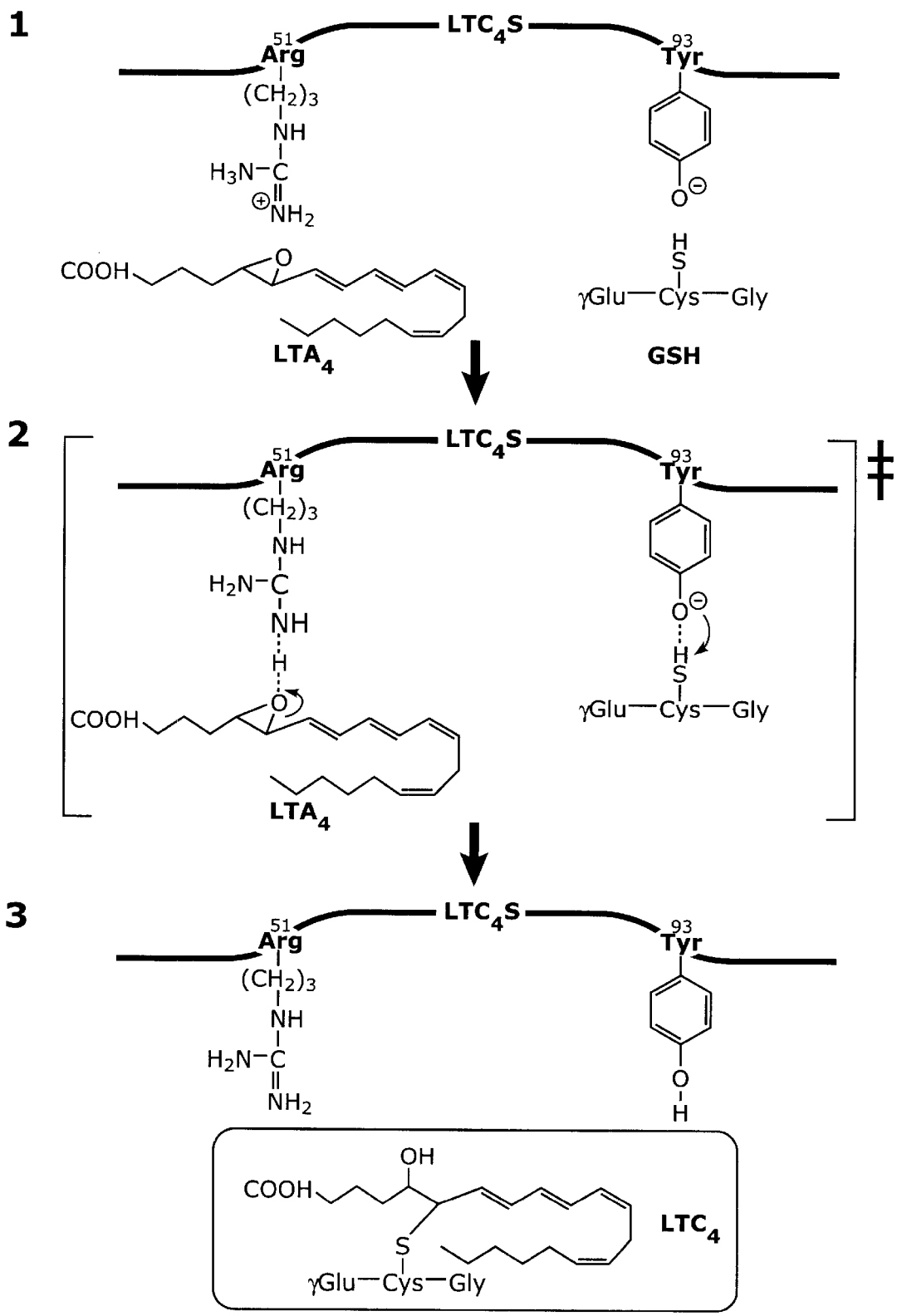
FIG. 13 depicts a proposed transition state for the LTC$_4$ synthase mechanism, with Arg 51 as an acid catalyst for the epoxide ring opening and Tyr 93 as a base catalyst for thiolate formation on glutathione. The mechanism may either be stepwise (e.g., prior protonation of epoxide) or concerted.
Figure 14:
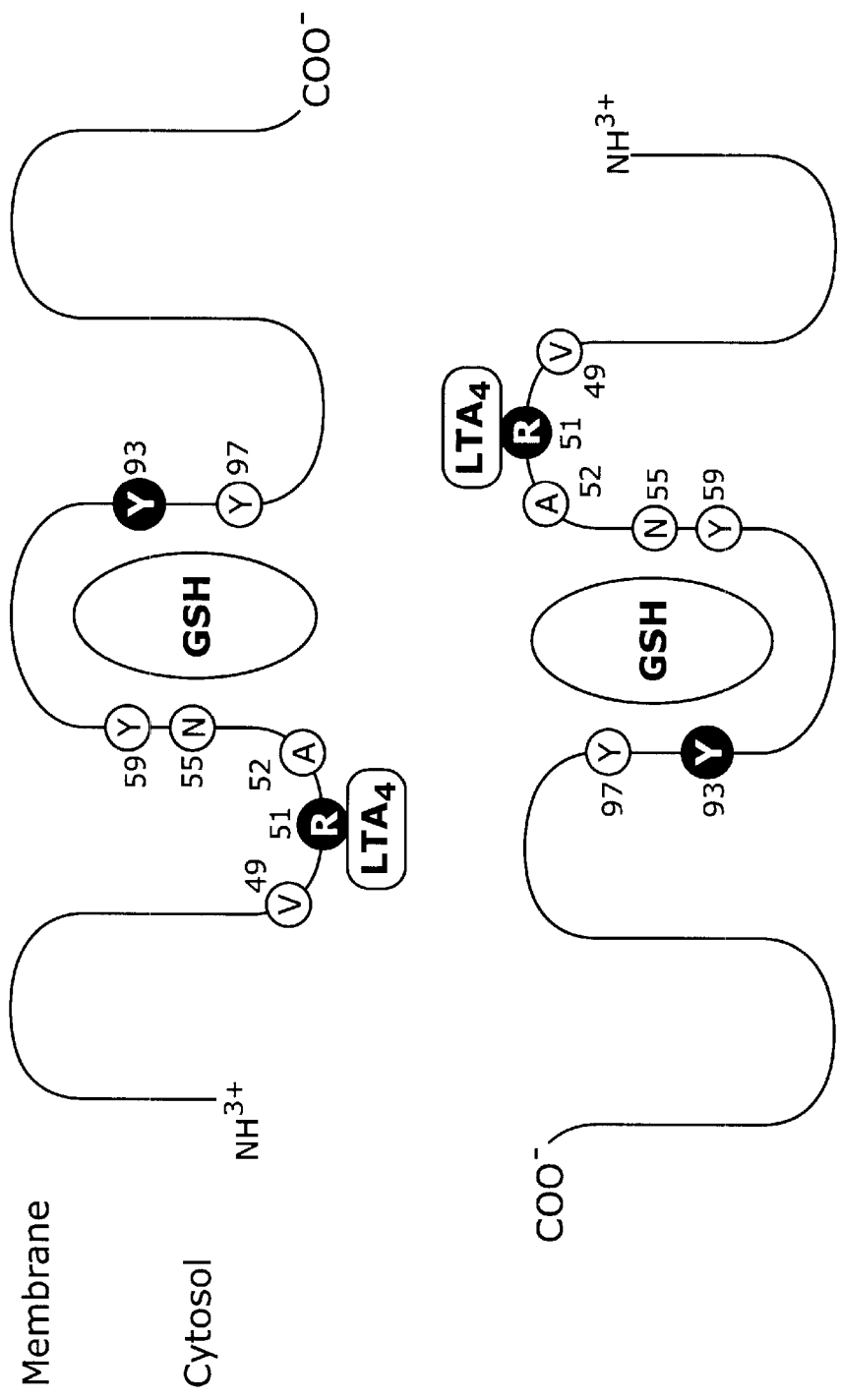
FIG. 14 shows a proposed orientation of LTC$_4$ synthase in a fluid membrane.

Kinetic analysis of the isolated recombinant Y93F established a greater than 90% reduction in $V_{max}$ (Table 2) and confirmed the increase in $K_m$ for GSH. The catalytic efficiency ($V_{max}/K_m$) of Y93F (0.14) is 1/260th of that of the wild-type enzyme (36.6). The loss in function with the Y93F mutant prompted an examination of the pH dependency of the residual enzyme (FIG. 10) as an indication that Y93 was involved in thiolate anion formation. A shift in the optimum to a higher pH was observed in the microsomal assay with 5-fold more Y93F as compared to Y59F or the wild-type construct. Furthermore, the pH-dependent conjugation curve of Y93F resembled that of the non-enzymatic reaction.

ADDITIONAL POINT MUTATIONS OF THE HYDROPHILIC LOOPS: The carboxyl terminus of the first hydrophilic loop is implicated in the binding of drugs, termed FLAP inhibitors, that interfere with the cellular presentation of released arachidonic acid to 5-lipoxygenase (Abramovitz et al., *Eur. J. Biochem.*, 215:105, 1993; and Vickers et al., *Mol. Pharmacol.*, 42:94, 1992). The cellular and subcellular conjugation function of $LTC_4$ synthase is inhibited by relatively high concentrations of a FLAP inhibitor. 8 of 11 amino acid residues in the carboxyl terminus of the first hydrophilic loop of LTC$_4$ synthase are identical to those of FLAP. Thirteen point mutations within the carboxyl terminus of this loop and the nearby second hydrophobic domain, namely L39F, E45Q, F46Y, E47Q, R48S, Y50F, Q53N, V54Q, F60Y, L62T, T66V, V69S, H75Q and E76Q (FIG. 8), did not affect the function of the microsomal mutant enzyme from transfected COS cells. A single point mutation at the amino terminus of the first hydrophilic loop, Q25K, and point mutations within the second hydrophilic loop, R92S, R99S, S100V, R104S, Y109I and S111V, did not affect the function of the microsomal enzyme. The A52S mutant of the carboxyl terminus of the first hydrophilic loop did exhibit an increase in $K_m$ for GSH (Table 2).

DELETION MUTATIONS: Neither the deletion of the charged amino acids K2 and D3 at the amino terminus nor the deletion of the 14 amino acids at the carboxyl terminus altered the function of the microsomal recombinant enzyme expressed by the COS cells (data not shown). However, the deletion of the third hydrophobic domain with the carboxyl terminus did eliminate function even though protein was present by immunoblot analysis of the COS cell transfectant (data not shown).

SUBSTITUTION OF THE SECOND OR THIRD HYDROPHOBIC DOMAIN OF FLAP FOR COMPARABLE REGIONS OF LTC$_4$ SYNTHASE: Because the elimination of LTC$_4$ synthase function with deletion of the third hydrophobic domain could reflect a conformational effect, the hydrophobicity provided by that region was restored by substitution of the comparable FLAP domain with 33 amino acid differences and 7 extra amino acids added at carboxyl terminus. This substitution to create a hybrid LTC$_4$S/FLAP protein (hybrid A, FIG. 11A) provided COS cell microsomes with enzyme activity. The $K_m$ value for LTA$_4$-ME is comparable to wild-type enzyme. A hybrid created by the substitution of the second hydrophobic domain of FLAP with 16 amino acid differences for that of LTC$_4$ synthase (hybrid B, FIG. 11B) did not function. However, substitution for the residues 66–81 (hybrid C, FIG. 11C) within this domain with residues 70–85 of FLAP containing 10 amino acid differences plus a mutation P78L provided active recombinant hybrid protein with the expected $K_m$ value for LTA$_4$-ME.

Figures 9, 12:
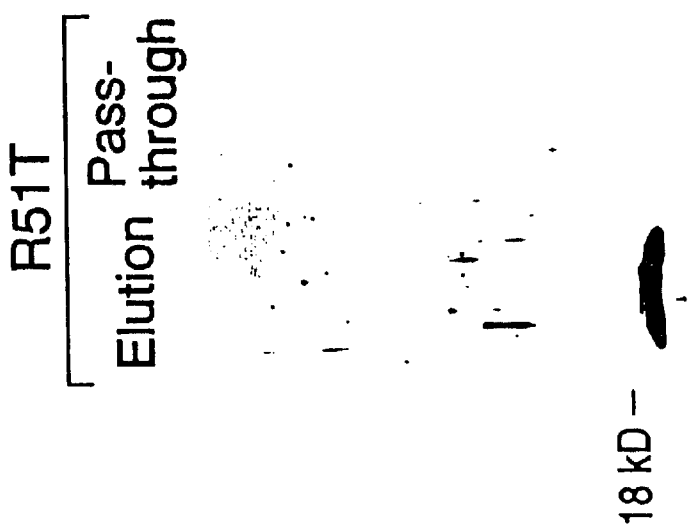
FIG. 9 presents SDS-PAGE immunoblot analysis of pass-through and probe read eluted fractions, respectively, of the S-hexyl GSH agarose chromatography of an inactive mutant enzyme R51T.
FIG. 12 shows SDS-PAGE/immunoblot analysis of the wild-type enzyme (WT), R51I/wild-type pseudo-heterodimer (R51I/WT), and wild-type/wild-type pseudo-homodimer (WT/WT) after gel filtration chromatography. Fractions from gel filtration of these recombinant enzymes that correspond to a 36 kDa functional protein were electrophoresed in SDS-PAGE followed by imunoblotting.

EFFECT OF A PSEUDO-DIMER LTC$_4$ SYNTHASE ON THE CONJUGATION FUNCTION OF THE ENZYME: A covalent pseudo-homodimer of LTC$_4$ synthase was created by connecting two LTC$_4$ synthase cDNAs with 36 nucleotides that encode a 12-amino-acid bridge containing 6 histidine residues and a factor Xa recognition sequence. When this construct was transfected into COS-7 cells, the expressed protein migrated as a dimer both in gel filtration chromatography and in SDS-PAGE (FIG. 12). The expressed microsomal protein (WT/WT) is fully active in the microsomal conjugation of LTA$_4$-ME with GSH. Furthermore, the recombinant pseudo-heterodimer of R51I LTC$_4$ synthase monomer (R51I/WT) and wild-type monomer also retained enzymatic function. Kinetic studies with solubilized microsomes gave $K_m$ values for LTA$_4$-ME and GSH of 6.5 $\mu$M and 3.2 mM respectively, for the pseudo-heterodimer; these values are similar to those for the wild-type enzyme (Table 2).

EQUIVALENTS

It should be understood that the preceding is merely a detailed description of certain preferred embodiments of the present invention. It therefore should be apparent to those skilled in the art that various modifications and equivalents can be made without departing from the spirit or scope of the invention.

What is claimed is:

1. An isolated human LTC$_4$ synthase genomic clone consisting of SEQ ID NO.:10.

2. A unique fragment of LTC$_4$ synthase genomic clone selected from the group consisting of:
 a fragment of intron 1, consisting of at least a portion of SEQ ID NO.:10 nucleotides 1505–2949;
 a fragment of intron 2, consisting of at least a portion of SEQ ID NO.:10 nucleotides 3050–3151;
 a fragment of intron 3, consisting of at least a portion of SEQ ID NO.:10 nucleotides 3223–3306; and
 a fragment of intron 4, consisting of at least a portion of SEQ ID NO.:10 nucleotides 3389–3618.

3. A unique fragment of human LCT4 synthase genomic clone consisting of at least a portion of nucleotides 1–1359 of SEQ ID NO.:10 upstream of the LTC$_4$ start site.

4. An oligonucleotide primer specific for human LCT4 synthase genomic clone selected from the group consisting of:
 a fragment of intron 1, consisting of at least a portion of SEQ ID NO.:10 nucleotides 1505–2949;
 a fragment of intron 2, consisting of at least a portion of SEQ ID NO.:10 nucleotides 3050–3151;
 a fragment of intron 3, consisting of at least a portion of SEQ ID NO.:10 nucleotides 3223–3306; and
 a fragment of intron 4, consisting of at least a portion of SEQ ID NO.:10 nucleotides 3389–3618.

5. A hybridization probe specific for human LCT4 synthase genomic clone selected from the group consisting of:
 a fragment of intron 1, consisting of at least a portion of SEQ ID NO.:10 nucleotides 1505–2949;
 a fragment of intron 2, consisting of at least a portion of SEQ ID NO.:10 nucleotides 3050–3151;
 a fragment of intron 3, consisting of at least a portion of SEQ ID NO.:10 nucleotides 3223–3306; and
 a fragment of intron 4, consisting of at least a portion of SEQ ID NO.:10 nucleotides 3389–3618.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 622 base pairs
      (B) TYPE: nucleic acid
      (C) STRANDEDNESS: both
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: human LTC4 synthase cDNA (xi) SEQUENCE DESCRIPTION: SEQ ID NO: 1:

```
AGCGTTCCCC AGCTCGCCTT CACACACAGC CCGTGCCACC ACACCGACGG TACCATGAAG      60

GACGAGGTAG CTCTACTGGC TGCTGTCACC CTCCTGGGAG TCCTGCTGCA AGCCTACTTC     120

TCCCTGCAGG TGATCTCGGC GCGCAGGGCC TTCCGCGTGT CGCCGCCGCT CACCACCGGC     180

CCACCCGAGT TCGAGCGCGT CTACCGAGCC CAGGTGAACT GCAGCGAGTA CTTCCCGCTG     240
```

```
TTCCTCGCCA CGCTCTGGGT CGCCGGCATC TTCTTTCATG AAGGGGCGGC GGCCCTGTGC        300

GGCCTGGTCT ACCTGTTCGC GCGCCTCCGC TACTTCCAGG GCTACGCGCG CTCCGCGCAG        360

CTCAGGCTGG CACCGCTGTA CGCGAGCGCG CGCGCCCTCT GGCTGCTGGT GGCGCTGGCT        420

GCGCTCGGCC TGCTCGCCCA CTTCCTCCCG GCCGCGCTGC GCGCCGCGCT CCTCGGACGG        480

CTCCGGACGC TGCTGCCGTG GGCCTGAGAC CAAGGCCCCC GGGCCGACGG AGCCGGGAAA        540

GAAGAGCCGG AGCCTCCAGC TGCCCCGGGG AGGGGCGCTC GCTTCCGCAT CCTAGTCTCT        600

ATCATTAAAG TTCTAGTGAC CG                                                 622
```

(2) INFORMATION FOR SEQ ID NO: 2:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vii) IMMEDIATE SOURCE:
        (B) CLONE: deduced human LTC4 synthase protein (xi) SEQUENCE DESCRIPTION: SEQ ID NO: 2:

```
Met Lys Asp Glu Val Ala Leu Leu Ala Ala Leu Leu Gly Val Leu Le
1               5                   10                  15

Gln Ala Tyr Phe Ser Leu Gln Val Ile Ser Ala Arg Arg Phe Arg Va
            20                  25                  30

Ser Pro Pro Leu Thr Thr Gly Pro Pro Glu Phe Glu Arg Val Tyr Ar
        35                  40                  45

Ala Gln Val Asn Cys Ser Glu Tyr Phe Pro Leu Phe Leu Ala Thr Le
    50                  55                  60

Trp Val Ala Gly Ile Phe Phe His Glu Gly Ala Ala Ala Leu Cys Gl
65                  70                  75                  80

Leu Val Tyr Leu Phe Ala Arg Leu Arg Tyr Phe Gln Gly Tyr Ala Ar
                85                  90                  95

Ser Ala Gln Leu Arg Leu Ala Pro Leu Tyr Ala Ser Ala Arg Ala Le
            100                 105                 110

Trp Leu Leu Val Ala Leu Ala Ala Leu Gly Leu Leu Ala His Phe Le
        115                 120                 125

Pro Ala Ala Leu Arg Ala Ala Leu Leu Gly Arg Leu Arg Thr Leu Le
    130                 135                 140

Pro Trp Ala
145
```

(2) INFORMATION FOR SEQ ID NO: 3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO -continued

```
        (v) FRAGMENT TYPE: internal (vii) IMMEDIATE SOURCE:
            (B) CLONE: LTC4 synthase tryptic fragment (xi) SEQUENCE DESCRIPTION: SEQ ID NO: 3:

Val Ser Pro Pro Leu Thr Thr Gly Pro Pro Glu Phe Glu Arg
1               5                   10

(2) INFORMATION FOR SEQ ID NO: 4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: Primer used in PCR amplification of LTC4
                synthase gene (xi) SEQUENCE DESCRIPTION: SEQ ID NO: 4:

AGCGTTCCCC AGCTCGCCTT C                                           21

(2) INFORMATION FOR SEQ ID NO: 5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: Primer used in PCR amplification of LTC4
                synthase gene (xi) SEQUENCE DESCRIPTION: SEQ ID NO: 5:

CGGTCACTAG AACTTTAATG ATAGAG                                      26

(2) INFORMATION FOR SEQ ID NO: 6:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
            (B) CLONE: human LTC4 synthase loop residues 25 to 58

(xi) SEQUENCE DESCRIPTION: SEQ ID NO: 6:
```

```
Gln Val Ile Ser Ala Arg Arg Ala Phe Arg Val Ser Pro Pro Leu Th
1               5                   10                  15

Thr Gly Pro Pro Glu Phe Glu Arg
            20
```

(2) INFORMATION FOR SEQ ID NO: 7:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: human LTC4 synthase loop residues 90 to 113

(xi) SEQUENCE DESCRIPTION: SEQ ID NO: 7:

```
Arg Leu Arg Tyr Phe Gln Gly Tyr Ala Arg Ser Ala Gln Leu Arg Le
1               5                   10                  15

Ala Pro Leu Tyr Ala Ser Ala Arg
            20
```

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: human LTC4 synthase loop residues 136 to 150

(xi) SEQUENCE DESCRIPTION: SEQ ID NO: 8:

```
Arg Ala Ala Leu Leu Gly Arg Leu Arg Thr Leu Leu Pro Trp Ala
1               5                   10                  15
```

(2) INFORMATION FOR SEQ ID NO: 9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vii) IMMEDIATE SOURCE:
        (A) LIBRARY: N-terminal 22 amino acids of purified human
            LTC4 synthase (xi) SEQUENCE DESCRIPTION: SEQ ID NO: 9:

Met Lys Asp Glu Val Ala Leu Leu Ala Ala Val Thr Leu Leu Gly Va
1               5                   10                  15

Leu Leu Gln Ala Tyr Phe
            20

(2) INFORMATION FOR SEQ ID NO: 10:

(i) SEQUENCE CHARACTERISTICS:
        (A) LENGTH: 4465 base pairs
        (B) TYPE: nucleic acid
        (C) STRANDEDNESS: both
        (D) TOPOLOGY: not relevant (ii) MOLECULE TYPE: DNA (genomic)

(vii) IMMEDIATE SOURCE:
        (B) CLONE: human LTC4 synthase genomic clone (xi) SEQUENCE DESCRIPTION: SEQ ID NO: 10:

```
GAGCTCACAG AGCCCCCAGC TGGGGCATAT CTGGTTTCCG GGGGCAGGGG CGATACCCAG     60
AGGAGGAAGA AGGGATTCTG AGAGAGCCCA ACAGGCTCCG AGCCTCAGGC TGGAGCTGAG    120
CTTGGGGCAG CAAGGAAGGA CCAGGTGCGA GGGCAGAACC ATGCGGCCCG ACCCCTGCAG    180
CACGGCCTGT GGCCTCCCCC AGCTCCTGCC CGTGCTTCTG GGTCAGTCTG ACTTTGCCA     240
CTTCTGACCA AAAGCCACCG CAAACCCACT CAAGCCAAAA GAGGAAGTGA CCGTTAGGCC    300
CAACTGGGAA GGCTGGCGGC CAGGGCACT CCAGGCAGGG CGAGGGGGC GGCCGGGGC      360
GCTCCAGGCG GGGCGAGGGA GACACCCAGA ACTCCAGGCA GGAGTCCTCG GGTGCCACCT    420
TTCCTCTCCA CCTGGCCCTG CGTGGGCTCT GTCCTCAGGG TGGCCCGCCG TAGTCCCCCT    480
CCCCACTCTG AGTTTCCTGT CCCAAAGTCC TAAGGAAGTT TCCAGAACTA CATCTCACCA    540
TCTTGAGTCA GCCTTGGCTC AGTGTCCATC TCACAGGCCT GGAAGGGGCA GGAGTCAGCA    600
CTGTCCAGAC CACAGGGCCT GAGTGTGGGG AGGGCAGCCG TCTAGGAAGG TGGTGGAGGG    660
TTGTTACCTT GAGGCAAGAG GGCTGCGGGG CAGAAAGACA CAGCAGGTGA CTGTTGTGGG    720
AGGCCCAAGA GAGGCCTGGG AGAGGGATGG CCCACAAGGG CTGACCCTCC CGCCACCCAG    780
GGGGCCTTGG ACAGGTTTCC TCCTGGCAGG GTGGCCCTTG TGCATGGAAC CCCTACAACG    840
ACTAAGGCTG GCAGGCATGA GGTTTCCTGA AGGAGAAAGA GCTTGTGGGG CCCAGTGTGG    900
CTGGGGGGGC GCTGGGACTC CATTCTGAAG CCAAAGGCAC TGGGAAGGGC TTCCGCAGAG    960
GAGGGTTTGG CAGGGGTTGC CAGGAACAGC CTGGATGGGG ACAGGGAACA GATAAGGTGG   1020
GTGGAGGAGT TAGCCGGGAG CCTGGGGCTG GCTCCAGCAT GATGTGGGGG TCTGCAAGGC   1080
CCTGGAGAAA GTGGGGTGGT GCAGCAGGGG GCACACCCAC AGCTGGAGCT GACCCAGATG   1140
GACAGCTTGG GCTCTGCCAC GCGGGACTAG GCAAGGAAGG GGCACGAACA AGCAGGAAGT   1200
GGTGAGGCGG TCTCCAGCTA GCTGCTCTCC CCTGCCCAGA CTTTGGTTTC CTCCCTGCTG   1260
GCTTGGCCTG GCTCCCTGGC TCTGTGTGGT ATGGTCACAC CCCCGTGCAC CCCCTCCACT   1320
GAGATGGGGC GGGGAGAGCA CCGAGGCTGC TCTTCCTCTC CTGGGCCGTC CTCTGAGCAG   1380
CAGACGGGGC TAAGCGTTCC CCAGCTCGCC TTCACACACA GCCCGTGCCA CCACACCGAC   1440
GGTACCATGA AGGACGAGGT AGCTCTACTG GCTGCTGTCA CCCTCCTGGG AGTCCTGCTG   1500
CAAGGTGGGC TGGTTCCTAT CTAGGAAGAG GGTGGGCCTT AGATCCCTAC AGCTTGCCCT   1560
CTGCCCCCTA GGCCCAGGTG GAGGGCAGAG GTGGGGACTC CAGCCCAGGC CCAAGCTGGA   1620
```

-continued

```
AGAGGGTGGG GACTTTCAGG GAACTGGGGG GCACCTGGCT GTGAGAGCTG TAGGACTTGG      1680

GGGTGGCAAG GGTGCCAGGA CAAATGGTAG GATAGCCATG GGCTTGGGGA AGCTGATCTC      1740

TGCTCTTTCC AGCTGTCCCC TCTCTGGGCG TCCCAGCAAG CGGCCCCCAT TCCCTGGCTC      1800

TGCTTCAAAG GCACCTCCAT ACTGGGACCA CGTGGAGCAG GGTAGAGGTG GGACTCCTTC      1860

CTCCAGCCCC CTAAAAAGAG CCTGCTTAAT GCCTTTCTCA GACTGGCCCT AAAGGACACA      1920

TTCCTTGGCC AGATATCCTT GCCACCTAAG AGACACCACT ACTCCACAGT GTGTGGGCTA      1980

GGATAAGGCA CAGCCTGGGG AGGGGCTCT GAAGGGGCTG AACAGACAGG CCAGCCTGAC       2040

CTCCAGCTGC TCCTGCACTG AGCTGGATGG CCACCCTGTG ACACCCATCT GCAGAGGGCC      2100

CAGAACCAAA GGTGCCAGGG CTGCAGGACT CAGGGGAGA TGGTCCGACG GGAGGTCTGG       2160

GGAGGGAGCG CACAGCCAGC ACTGGTCTGT GTGTGGTCTG GCCTGGCCTC ACCTGACCAA      2220

GAGAAGGGCT CCTGCCCACA GAGAAACTTT AGGGCCAGCC CACCCTCTGC AACTACCCCA      2280

GCCCTGGGGT CCTGGGGTTA GGCTAGGAGA GTCCCAGCTG CAACCTCCTG GGAGCAGGAG      2340

AGAAGGTGTC TGTCAGATTT AGGCCTGGGA CCGGAATGCA GGAACAGAGA AACTGAGGTT      2400

TGGAGGCACA GGGACGCAGG CTTTAGTGAT CCCGGCCTGA GGCAGGGTCA GAGGGCCCTG      2460

CTGGTGGGCG CTGGTAGGTG GGTGACCAGG GACTGTTAGC TACAGGGAGT GTGCTTCCTT      2520

GCACCTGGGA GGATGCAGCC AGCTCTGCCC TCAGACTCCC GAGGCACTTC CTGGCCAGGG      2580

ACCTGAAAGC TGCATTTGCC TGTGTTTTGA GAGTGAAATG ATTCAGAAAC AAGGACTCAA      2640

GTGGTCTCTC TCGCGGAGCA GGTGTCCCTG TGCCTGAATC ACTCACCCTC CCCCATACAC      2700

TCACAGGTTG GGACAGGGCC TCTCTGCGCC CCAGGCTTCA GCCCTGCCCT CCTCGCTGAA      2760

TGTCAGGGAC ACAGGGCAGG CCAGGGATGG GTGAGACGAG AGGTCTCCTC GGGCGGGGAG      2820

GGGGCGGGGT TCCGCCTTAG GGAGGAGAGG ACACGGCCAA GTGAAGGGCC AGATTGCAGG     2880

ATCCCTCCCA CTCCCATCTC TGGGGCTTCG GGTGTCCAGA CCTGACTCCC GCTCCCCCTC     2940

CTCCCCCAGC CTACTTCTCC CTGCAGGTGA TCTCGGCGCG CAGGGCCTTC CGCGTGTCGC     3000

CGCCGCTCAC CACCGGCCCA CCCGAGTTCG AGCGCGTCTA CCGAGCCCAG TGAGGCGCGG     3060

CGGGAGGGCG CGGGGCGGGG AGCGAGCCCC AGGCGGGTCC GGGTCGCAGG ACCATCCCGG     3120

CCGGCGCGCT CATCCCACCC GCCCACCGCA GGGTGAACTG CAGCGAGTAC TTCCCGCTGT     3180

TCCTCGCCAC GCTCTGGGTC GCCGGCATCT TCTTTCATGA AGGTCGGGGT GTGGGGCAGG     3240

GGCGCACGCG CTGGACCCCC GGGACCCGCG CAGGGCGCTC ACCAGGCCCG TGCGTACCTC     3300

TCGCAGGGGC GGCGGCCCTG TGCGGCCTGG TCTACCTGTT CGCGCGCCTC CGCTACTTCC     3360

AGGGCTACGC GCGCTCCGCG CAGCTCAGGT GAGGGCCGGG CGGGGAGCGG GGCGGGGCCG     3420

GGGAAAGATC GCGGGCGGGC GGGGCTCCTG GGGAGCGGGA CCGAAGCTGG GGGCGGGCGA     3480

CGGGCCGGAG CCCAGCGCCT TTGGGGATTC GGTGGGCGAG CCCTGGCGGC GGCCAGAGGA     3540

AGTCCCCGTG GGGCCAGGGT TGCGGCGGGG AAGAAGCGGG CCTCCTCGCG CCACCTCCCC     3600

GCTGACCGCC GCCCGCAGGC TGGCACCGCT GTACGCGAGC GCGCGCGCCC TCTGGCTGCT     3660

GGTGGCGCTG GCTGCGCTCG GCCTGCTCGC CCACTTCCTC CCGGCCGCGC TGCGCGCCGC     3720

GCTCCTCGGA CGGCTCCGGA CGCTGCTGCC GTGGGCCTGA GACCAAGGCC CCCGGGCCGA     3780

CGGAGCCGGG AAAGAAGAGC CGGAGCCTCC AGCTGCCCCG GGAGGGGCG CTCGCTTCCG      3840

CATCCTAGTC TCTATCATTA AAGTTCTAGT GACCGAGACC CGGGCTGCGT TCTCTGGGTC     3900

CGCGGGGGTG GCGCACCGCG GGCTACGGAG CCTGGAGGGG CCCAGCCCGA GTCCGGGCAG     3960

CCCGGGGCGG GCTTCCTAGT GGCGGCGTGA GAGTGGCTGC GAAGGAACGA GCCCTCCCCC     4020
```

```
TGGGGCGGGA CTGGATCCGG TCTTCACCTC CTACCCCACT CCCTACTCAG CCTCGGGGTC    4080

ACAAGGCCGC CCAGTCCTGC CGGGGTTCAC CCTCCTAGCG CTCAGCGGTC TCCTCACCGG    4140

TCCCCCTCCT CAGGGGCCTT CCCTCGACTC TCAGCCGCCG CAGTCCCTCG TCCCCTGGCC    4200

TTCACAGCTG ACACTAGATA GAGCCTGTGG CTCTCTCCCC AGGTGAGGGC AGGGGTTTTT    4260

CTTTTGGTCA GCACTGGATC CCCCTCGTTA ACTGTAGGTG TTCAGGGCAG CCCTCCGAGG    4320

TCCGCAGAGC TGCGGGCACC ATGGGAACGA AGTGAGTCAG TGACAGGCGG TCTCAAGGAA    4380

ATGTCCAGAA GCCTTGGGGA TCCAGGGGAG GCCCACAGAA ACAAAGAAGT GACTTTTAGC    4440

CAAGTATGCA GGAGAAACGG AGGAG                                         4465
```